US011643676B2

(12) United States Patent
Petillo et al.

(10) Patent No.: US 11,643,676 B2
(45) Date of Patent: May 9, 2023

(54) IN VITRO GLYCOSYLATION OF PROTEINS AND ENZYMES

(71) Applicant: Design-Zyme LLC, Lawrence, KS (US)

(72) Inventors: Peter Albert Petillo, Lawrence, KS (US); Dwight O'Dell Deay, III, Lawrence, KS (US); Michael Gregory Branden, Lawrence, KS (US)

(73) Assignee: Design-Zyme LLC, Lawrence, KS (US)

( * ) Notice: Subject to any disclaimer, the term of this patent is extended or adjusted under 35 U.S.C. 154(b) by 216 days.

(21) Appl. No.: 17/301,590

(22) Filed: Apr. 8, 2021

(65) Prior Publication Data

US 2021/0230661 A1    Jul. 29, 2021

Related U.S. Application Data

(62) Division of application No. 16/224,795, filed on Dec. 19, 2018, now Pat. No. 11,021,730.

(60) Provisional application No. 62/607,655, filed on Dec. 19, 2017.

(51) Int. Cl.
| | | |
|---|---|---|
| *C12Q 1/00* | (2006.01) | |
| *C07K 1/00* | (2006.01) | |
| *C07K 1/107* | (2006.01) | |
| *C12N 9/02* | (2006.01) | |
| *C12N 9/04* | (2006.01) | |
| *C12P 21/00* | (2006.01) | |
| *C12N 9/06* | (2006.01) | |

(52) U.S. Cl.
CPC .............. *C12Q 1/005* (2013.01); *C07K 1/006* (2013.01); *C07K 1/1077* (2013.01); *C12N 9/0004* (2013.01); *C12N 9/0006* (2013.01); *C12P 21/005* (2013.01)

(58) Field of Classification Search
None
See application file for complete search history.

(56) References Cited

U.S. PATENT DOCUMENTS 5,691,154 A    11/1997 Callstrom

OTHER PUBLICATIONS

Umekawa et al. (Efficient transfer of sialo-oligosaccharide onto proteins by combined use of a glycosynthase-like mutant of Mucor hiemalis endoglycosidase and synthetic sialo-complex-type sugar oxazoline, Biochimica et Biophysics Acts 1800 (2010) 1203-1209).*
Zhou, M.; Diwu, Z.; Panchuk-Voloshina, N.; Haugland, R. P., A Stable Nonfluorescent Derivative of Resorufin for the Fluorometric Determination of Trace Hydrogen Peroxide: Applications in Detecting the Activity of Phagocyte NADPH Oxidase and Other Oxidases. Analytical Biochemistry 1997, 253 (2), 162-168.
Solá, R. J.; Griebenow, K., Effects of glycosylation on the stability of protein pharmaceuticals. Journal of pharmaceutical sciences 2009, 98 (4), 1223-1245.
Kägi, J. H. R.; Vallee, B. L., The Role of Zinc in Alcohol Dehydrogenase: V. The Effect of Metal-Binding Agents on the Structure of the Yeast Alcohol Dehydrogenase Molecule. Journal of Biological Chemistry 1960, 235 (11), 3188-3192.
Dalziel, M.; Crispin, M.; Scanlan, C. N.; Zitzmann, N.; Dwek, R. A., Emerging principles for the therapeutic exploitation of glycosylation. Science (New York, N.Y.) 2014, 343 (6166), 1235681.
Wilson, R.; Turner, A. P. F., Glucose oxidase: an ideal enzyme. Biosensors and Bioelectronics 1992, 7 (3), 165-185.
Bankar, S. B.; Bule, M. V.; Singhal, R. S.; Ananthanarayan, L., Glucose oxidase—An overview. Biotechnology Advances 2009, 27 (4), 489-501.
Rich, J. R.; Withers, S. G., Emerging methods for the production of homogeneous human glycoproteins. Nature Chemical Biology 2008, 5, 206.
Li, C.; Wang, L.-X., Chemoenzymatic Methods for the Synthesis of Glycoproteins. Chemical Reviews 2018, 118 (17), 8359-8413.
Schmaltz, R. M.; Hanson, S. R.; Wong, C.-H., Enzymes in the Synthesis of Glycoconjugates. Chemical Reviews 2011, 111 (7), 4259-4307.
Zeng, Y.; Wang, J.; Li, B.; Hauser, S.; Li, H.; Wang, L. X., Glycopeptide synthesis through endo-glycosidase-catalyzed oligosaccharide transfer of sugar oxazolines: probing substrate structural requirement. Chemistry (Weinheim an der Bergstrasse, Germany) 2006, 12 (12), 3355-64.
Wang, N.; Seko, A.; Daikoku, S.; Kanie, O.; Takeda, Y.; Ito, Y., Non-enzymatic reaction of glycosyl oxazoline with peptides. Carbohydrate research 2016, 436, 31-35.
Fujita, M.; Shoda, S.; Haneda, K.; Inazu, T.; Takegawa, K.; Yamamoto, K., A novel disaccharide substrate having 1,2-oxazoline moiety for detection of transglycosylating activity of endoglycosidases. Biochimica et biophysica acta 2001, 1528 (1), 9-14.

(Continued)

*Primary Examiner* — Suzanne M Noakes
*Assistant Examiner* — Jae W Lee

(57) ABSTRACT

The present invention is broadly concerned with new in vitro glycosylation methods that provide rational approaches for producing glycosylated proteins, and the use of glycosylated proteins. In more detail, the present invention comprises methods of glycosylating a starting protein having an amino sidechain with a nucleophilic moiety, comprising the step of reacting the protein with a carbohydrate having an oxazoline moiety on the reducing end thereof, to covalently bond the amino sidechain of the starting protein with the oxazoline moiety, wherein the glycosylated protein substantially retains the structure and function of the starting protein. Target proteins include oxidase, oxidoreductase and dehydrogenase enzymes. The glycosylated proteins advantageously have molecular weights of at least about 7500 Daltons. In a further embodiment, the present invention concerns the use of glycosylated proteins, fabricated by the methods disclosed herein, in the assembly of amperometric biosensors.

15 Claims, 11 Drawing Sheets

(56) References Cited

OTHER PUBLICATIONS

Dutta, D.; Mandal, C.; Mandal, C., Unusual glycosylation of proteins: Beyond the universal sequon and other amino acids. Biochimica et biophysica acta. General subjects 2017, 1861 (12), 3096-3108.

Le Pape, A.; Muh, J. P.; Bailey, A. J., Characterization of N-glycosylated type I collagen in streptozotocin-induced diabetes. The Biochemical journal 1981, 197 (2), 405-412.

Robins, S. P.; Bailey, A. J., Age-related changes in collagen: the identification of reducible lysine-carbohydrate condensation products. Biochemical and biophysical research communications 1972, 48 (1), 76-84.

Wang, Y.; Xu, A.; Knight, C.; Xu, L. Y.; Cooper, G. J. S., Hydroxylation and Glycosylation of the Four Conserved Lysine Residues in the Collagenous Domain of Adiponectin: Potential Role in the Modulation of Its Insulin-Sensitizing Activity. Journal of Biological Chemistry 2002, 277 (22), 19521-19529.

Yamauchi, M.; Sricholpech, M., Lysine post-translational modifications of collagen. Essays in biochemistry 2012, 52, 113-133.

Krafczyk, R.; Macošek, J.; Jagtap, P. K. A.; Gast, D.; Wunder, S.; Mitra, P.; Jha, A. K.; Rohr, J.; Hoffmann-Roder, A.; Jung, K.; Hennig, J.; Lassak, J., Structural Basis for EarP-Mediated Arginine Glycosylation of Translation Elongation Factor EF-P. mBio 2017, 8 (5), e01412-17.

Maekawa, H.; Yamazumi, K.; Muramatsu, S.; Kaneko, M.; Hirata, H.; Takahashi, N.; de Bosch, N. B.; Carvajal, Z.; Djeda, A.; Arocha-Pinango, C. L.; et al., An A alpha Ser-434 to N-glycosylated Asn substitution in a dysfibrinogen, fibrinogen Caracas II, characterized by impaired fibrin gel formation. The Journal of biological chemistry 1991, 266 (18), 11575-81.

Park, J. B.; Kim, Y. H.; Yoo, Y.; Kim, J.; Jun, S.-H.; Cho, J. W.; El Qaidi, S.; Walpole, S.; Monaco, S.; García-García, A.A.; Wu, M.; Hays, M. P.; Hurtado-Guerrero, R.; Angulo, J.; Hardwidge, P. R.; Shin, J.-S.; Cho, H.-S., Structural basis for arginine glycosylation of host substrates by bacterial effector proteins. Nature Communications 2018, 9 (1), 4283.

Noguchi, M.; Fujieda, T.; Huang, W. C.; Ishihara, M.; Kobayashi, A.; Shoda, S.-i., A Practical One-Step Synthesis of 1,2-Oxazoline Derivatives from Unprotected Sugars and Its Application to Chemoenzymatic β-N-Acetylglucosaminidation of Disialo-oligosaccharide. Helvetica Chimica Acta 2012, 95 (10), 1928-1936.

Noguchi, M.; Tanaka, T.; Gyakushi, H.; Kobayashi, A.; Shoda, S.-i., Efficient Synthesis of Sugar Oxazolines from Unprotected N-Acetyl-2-amino Sugars by Using Chloroformamidinium Reagent in Water. The Journal of organic chemistry 2009, 74 (5), 2210-2212.

Huang, W.; Yang, Q.; Umekawa, M.; Yamamoto, K.; Wang, L.-X., Arthrobacter endo-beta-N-acetylglucosaminidase shows transglycosylation activity on complex-type N-glycan oxazolines: one-pot conversion of ribonuclease B to sialylated ribonuclease C. Chembiochem : a European journal of chemical biology 2010, 11 (10), 1350-1355.

Ochiai, H.; Huang, W.; Wang, L.-X., Endo-beta-N-acetylglucosaminidase-catalyzed polymerization of beta-Glcp-(1->4) GlcpNAc oxazoline: a revisit to enzymatic transglycosylation. Carbohydrate research 2009, 344 (5), 592-598.

Rising, T. W. D. F.; Heidecke, C. D.; Moir, J. W. B.; Ling, Z.; Fairbanks, A. J., Endohexosaminidase-Catalysed Glycosylation with Oxazoline Donors: Fine Tuning of Catalytic Efficiency and Reversibility. Chemistry—A European Journal 2008, 14 (21), 6444-6464.

Suda, M.; Sumiyoshi, W.; Kinoshita, T.; Ohno, S., Reaction of sugar oxazolines with primary amines. Tetrahedron Letters 2016, 57 (49), 5446-5448.

Yeung, B. K. S.; Chong, P. Y. C.; Petillo, P. A., Synthesis of glycosaminoglycans. J. Carbohydr. Chem. 2002, 21, 799-865.

Roth, M.; Papakonstantinou, E.; Karakiulakis, G., Chapter 9—Biological Function of Glycosaminoglycans. In Carbohydrate Chemistry, Biology and Medical Applications, Garg, H. G.; Cowman, M. K.; Hales, C. A., Eds. Elsevier Oxford, 2008; pp. 209-226.

Yamada, S.; Sugahara, K.; Özbek, S., Evolution of glycosaminoglycans. Communicative & Integrative Biology 2011, 4 (2), 150-158.

Cho, Y.-W.; Jang, J.; Park, C. R.; Ko, S.-W., Preparation and Solubility in Acid and Water of Partially Deacetylated Chitins. Biomacromolecules 2000, 1 (4), 609-614.

Cheung, R. C.; Ng, T. B.; Wong, J. H.; Chan, W. Y., Chitosan: An Update on Potential Biomedical and Pharmaceutical Applications. Marine drugs 2015, 13 (8), 5156-86.

Orviský, E.; Kéry, V.; Stančiková, M., Specific high performance liquid chromatographic determination of the molecular weight and concentration of hyaluronic acid in complex mixtures by labelled hyaluronate binding proteins. Biomedical Chromatography 1991, 5 (6), 251-255.

Motohashi, N.; Mori, I., Molecular weight determination of hyaluronic acid and its separation from mouse skin extract by high-performance gel permeation chromatography using a precision differential refractometer. Journal of Chromatography A 1984, 299, 508-512.

Yeung, B.; Marecak, D., Molecular weight determination of hyaluronic acid by gel filtration chromatography coupled to matrix-assisted laser desorption ionization mass spectrometry. Journal of Chromatography A 1999, 852 (2), 573-581.

Lomino, J.V.; Naegeil, A.; Orwenyo, J.; Amin, M.N.; Aebi, M.; Wang, L.-X., A two-step enzymatic glycosylation of polypeptides with complex N-glycans, Bioorganic & Medicinal Chemistry, 2013, 21, pp. 2262-2270.

Eschenfeldt, W. H.; Lucy, S.; Millard, C. S.; Joachimiak, A.; Mark, I. D., A family of LIC vectors for high-throughput cloning and purification of proteins. Methods in molecular biology (Clifton, N.J.) 2009, 498, 105-15.

Huynh, K.; Partch, C. L., Analysis of Protein Stability and Ligand Interactions by Thermal Shift Assay. In Current Protocols in Protein Science, John Wiley & Sons, Inc.: 2015; pp. 28.9.1-28.9.14.

Zonneveld, B. J.; van der Zanden, A. L., The red ade mutants of Kluyveromyces lactis and their classification by complementation with cloned ADE1 or ADE2 genes from *Saccharomyces cerevisiae*. Yeast 1995, 11 (9), 823-7.

Ahmad, M.; Hirz, M.; Pichler, H.; Schwab, H., Protein expression in Pichia pastoris: recent achievements and perspectives for heterologous protein production. Applied Microbiology and Biotechnology 2014, 98 (12), 5301-5317.

Gorris, H. H.; Walt, D. R., Mechanistic aspects of horseradish peroxidase elucidated through single-molecule studies. J Am Chem Soc 2009, 131 (17), 6277-82.

Inouye, Y.; Onodera, K.; Kitaoka, S.; Kirii, T., A Simplified Preparation of N-Acetyl-D-glucosamine. Bulletin of the Institute for Chemical Research, Kyoto University 1955, 33 (6), 270-271.

Bradford, M. M., A rapid and sensitive method for the quantitation of microgram quantities of protein utilizing the principle of protein-dye binding. Analytical Biochemistry 1976, 72 (1), 248-254.

Osset, M.; Pinol, M.; Fallon, M. J.; de Llorens, R.; Cuchillo, C. M., Interference of the carbohydrate moiety in coomassie brilliant blue R-250 protein staining. Electrophoresis 1989, 10 (4), 271-3.

Møller, H. J.; Poulsen, J. H., Staining of Glycoproteins/Proteoglycans on SDS-Gels. In The Protein Protocols Handbook, Walker, J. M., Ed. Humana Press: Totowa, NJ, 2009; pp. 569-574.

See, Y. P.; Olley, P. M.; Jackowski, G., The effects of high salt concentrations in the samples on molecular weight determination in sodium dodecyl sulfate polyacrylamide gel electrophoresis. Electrophoresis 1985, 6 (8), 382-387.

Search Report and Written Opinion dated May 1, 2019 in related PCT/US18/66407 filed on Dec. 19, 2018.

\* cited by examiner

IN VITRO GLYCOSYLATION OF PROTEINS AND ENZYMES

RELATED APPLICATIONS

The present application is a divisional of U.S. patent application Ser. No. 16/224,795, filed Dec. 19, 2018, entitled IN VITRO GLYCOSYLATION OF ENZYMES AND PROTEIN THERAPEUTICS, which claims the benefit of U.S. Provisional Patent Application Ser. No. 62/607,655, filed Dec. 19, 2017, entitled IN VITRO GLYCOSYLATION OF ENZYMES AND PROTEIN THERAPEUTICS. These applications are incorporated by reference herein.

STATEMENT REGARDING FEDERALLY SPONSORED RESEARCH

This invention was made with Government support under Contract HR0011-16-C-0124 awarded by DARPA. The Government has certain rights in the invention.

BACKGROUND OF INVENTION

Field of Invention

The present invention relates to new in vitro glycosylation methods that provide rational approaches for generating glycosylated proteins, and the use thereof.

Description of the Prior Art

Glycosylation is the process by which a carbohydrate is covalently attached to a target protein, such as an enzyme.[1-2] The attachment of carbohydrate moieties to proteins is a post-translational modification (PTM) that provides greater proteomic diversity to proteins. Glycosylation is critical for a wide range of biological processes, including cell attachment to the extracellular matrix and protein-ligand interactions in the cell. In the normal course of in vivo protein glycosylation, proteins are generally N-glycosylated on asparagine, or O-glycosylated on serine or threonine residues.

The glycosylation of proteins serves various functions.[2-3] For instance, it is known that some proteins and protein classes do not fold correctly in the absence of glycosylation. In other instances, proteins are not stable in the absence of oligosaccharides linked at the amide nitrogen of certain asparagine residues).[4] In addition, it is well established that some enzymes, such as glucose oxidase, display better stability and enzymatic parameters when glycosylated than in the absence of glycosylation.[5-6]

The importance of N-linked glycosylation is becoming increasingly evident in the field of pharmaceuticals.[2, 4-7] In recent years, a considerable emphasis has been placed on the development and deployment of in vitro glycosylation methods to alter and enhance the glycoforms on proteins, and in particular, antibodies.[8] A number of strategies have been reported.[9] One approach that has emerged is a multi-step process that involves production of an N-linked glycosylated protein, removal of the glycan moieties except for the terminal N-acetylglucosamine residues attached to asparagines, and subsequent enzymatic attachment of a new glycoform to alter the immune response of the target protein. This method of glycan remodeling requires (1) that the carbohydrate to be activated has an N-acetyl moiety at the 2-position of the reducing end of the carbohydrate to be conjugated, (2) that the target glycosylation sites have a GlcNAc residue already present on the protein, and (3) the carbohydrate to be conjugated be a substrate for endoglycosidase-catalyzed transglycosylation.[9-11] These requirements limit the modification of proteins utilizing this method. Recently, carbohydrate oxazolines have been used as activated glycosyl donor substrates for endoglycosidase-catalyzed transglycosylation.[12] In addition to the previously mentioned requirements, the naturally occurring hydrolytic activity of endoglycosidases towards the oxazolines limits the efficiency of this approach.[7-9, 11]

The in vivo N-glycosylation of lysine residues, i.e. attachment of a glycan to the terminal nitrogen of a lysine sidechain, in full-length proteins is rare.[13] Reports of $N^\epsilon$-glycosylation of lysine with glucose are largely associated with modifications of collagen in aged or diabetic tissue.[14-15] The in vivo attachment of other glycans to lysine remains undescribed. O-glycosylation of hydroxylysine has been reported and is also commonly associated with collagen formation.[16-17] In this instance, the lysine sidechain is post-translationally modified by hydroxylation, which provides the site for glycan attachment. While in vivo glycosylation of arginines and histidines have been reported, no corresponding selective in vitro glycosylation methodology has been reported.[13, 18-20]

Other references of interest include those where smaller molecular weight amino acid chains are glycosylated by the oxazoline approach.[11-12, 21-26] Much, if not most, of the existing art teaches away from direct lysine glycosylation by carbohydrate oxazolines in favor of methods in which the carbohydrate oxazoline is used as a substrate for an endo-ρ-N-acetylglucosaminidase to synthesize aspartate N-linked glycoproteins.[11-12, 21-26] Direct lysine glycosylation by carbohydrate oxazolines are often referred to as "by-products".[23]

SUMMARY OF THE INVENTION

The present invention is broadly concerned with new in vitro glycosylation methods that provide rational approaches for producing glycosylated proteins, and the use of glycosylated proteins. In more detail, the present invention comprises methods of glycosylating a starting protein having an amino sidechain with a nucleophilic moiety, comprising the step of reacting the protein with a carbohydrate having an oxazoline moiety on the reducing end thereof, in a compatible aqueous medium, to covalently bond the amino sidechain of the starting protein with the oxazoline moiety, wherein the glycosylated protein substantially retains the structure and function of the starting protein.

In another embodiment, the invention is concerned with glycosylated proteins comprising a starting protein having an amino sidechain with a nucleophilic moiety glycosylated with a carbohydrate having an oxazoline moiety on the reducing end thereof, wherein the oxazoline moiety is covalently bound with the nucleophilic moiety. The glycosylated proteins advantageously have molecular weights of at least about 7500 Daltons, and substantially retain the structure and function of the starting protein.

In a further embodiment, the present invention concerns the use of glycosylated proteins, fabricated by the methods disclosed herein, in the assembly of amperometric biosensors. The amperometric biosensors comprise a counter electrode, a reference electrode, one or more optional rejection layers, and a working electrode that comprises a sensing element, which comprises a support having a surface; and a layer on the surface, wherein the layer comprises an amino sidechain glycosylated enzyme, wherein the enzyme is predominantly in its active form.

Figure 18:
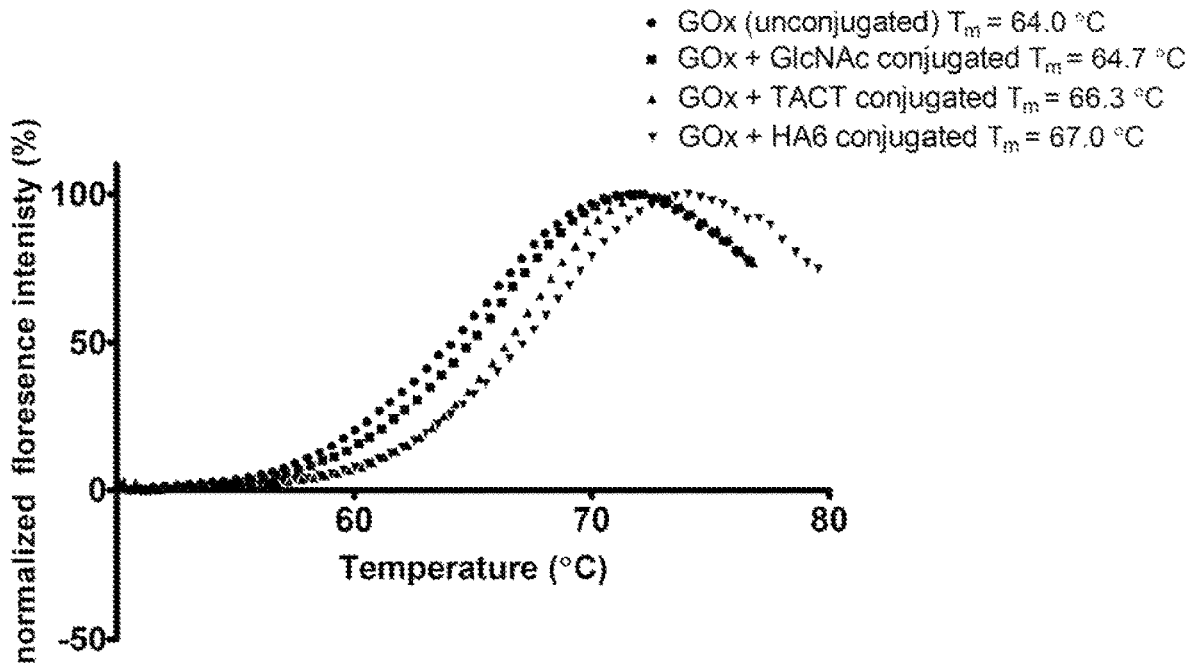
Figure 19:
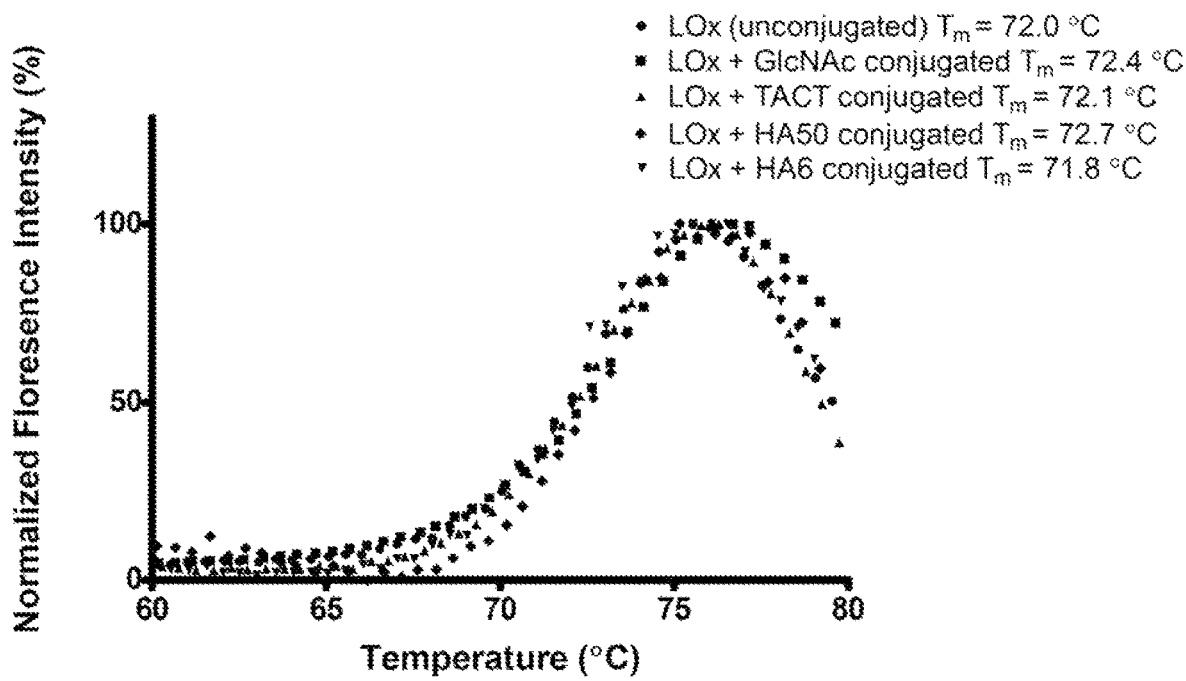
Figure 20:
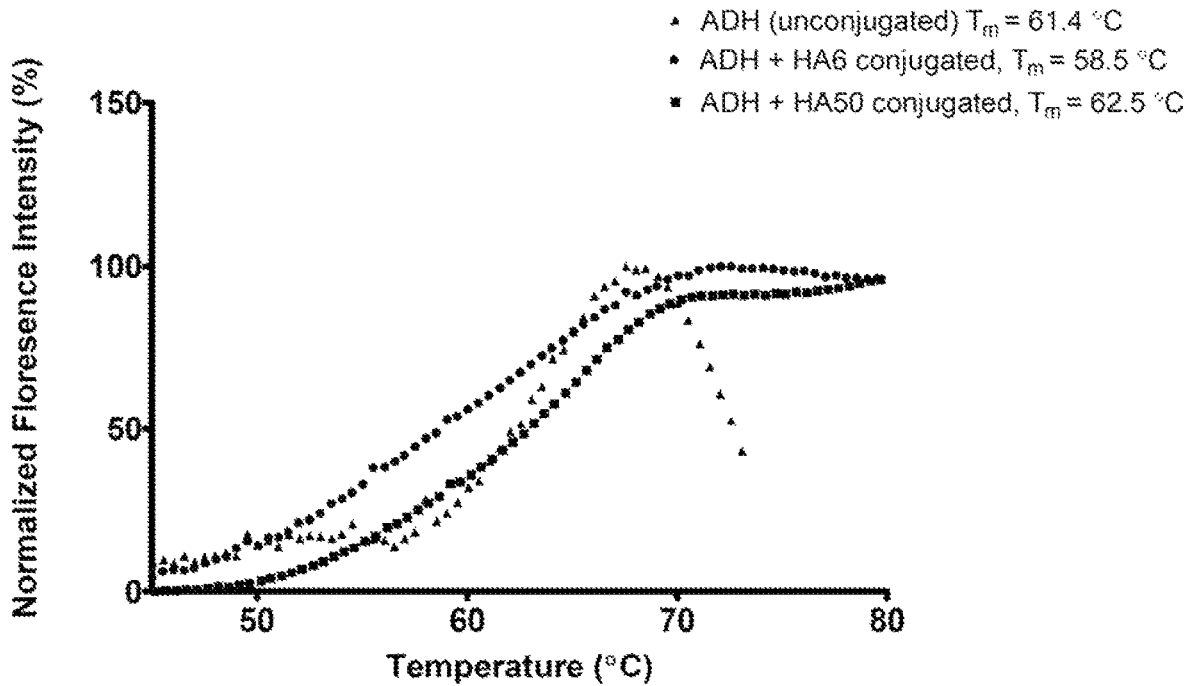
Figure 21:
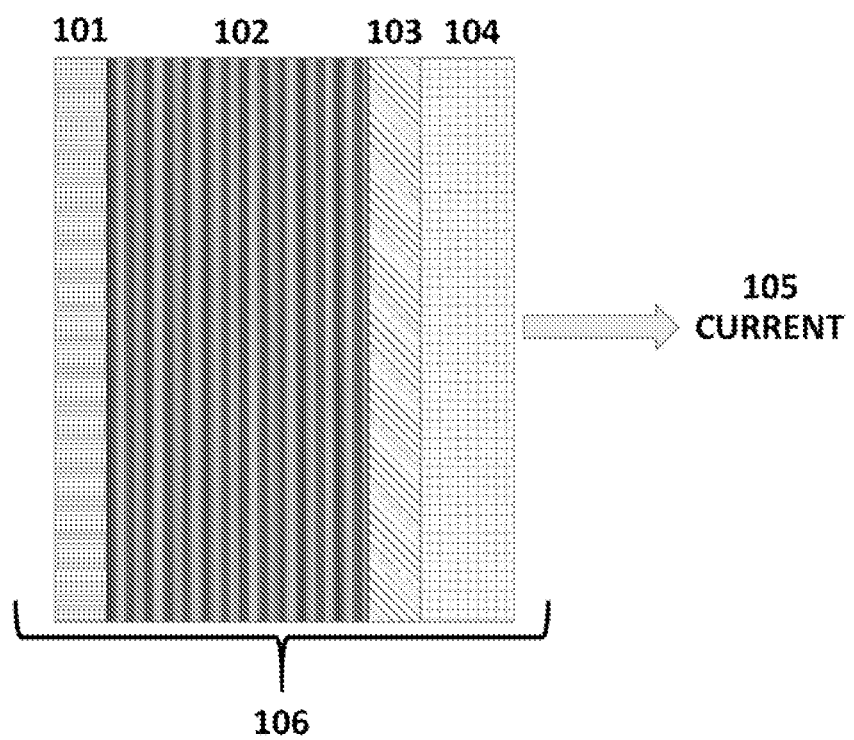

(column 4), and GOx conjugated with HA50 (column 5) after 96 hours of incubation at 42 C;

FIG. 18 is a representative fluorescence thermal shift assay (FTSA) comparison of wild-type native glucose oxidase (GOx, circles, Tm=72.0 C), GOx conjugated with GlcNAc (squares, Tm=72.4 C), GOx conjugated with TACT (up-triangles, Tm=72.1 C), and GOx conjugated with HA6 (down-triangles, Tm=71.8 C);

FIG. 19 is a representative fluorescence thermal shift assay (FTSA) comparison of wild-type native L-lactate oxidase (LOx, circles, Tm=72.0 C), LOx conjugated with GlcNAc (squares, Tm=72.4 C), LOx conjugated with TACT (up-triangles, Tm=72.1 C), LOx conjugated with HA6 (down-triangles, Tm=71.8 C), and LOx conjugated with HA50 (diamonds, Tm=72.7 C);

FIG. 20 is a representative fluorescence thermal shift assay (FTSA) comparison of wild-type native alcohol dehydrogenase (ADH, triangles, Tm=61.4 C), ADH conjugated with HA6 (triangles, Tm=58.5 C), and ADH conjugated with HA50 (triangles, Tm=62.5 C);

FIG. 21 is a schematic drawing of the working electrode of a prototypical amperometric biosensor.

DETAILED DESCRIPTION OF THE PREFERRED EMBODIMENTS

The present invention provides methods of modifying a protein, the methods comprise in vitro glycosylation methods that provide a rational approach for generating glycosylated versions of proteins. This invention allows for the custom control of the carbohydrate moieties placed on the protein including those that may be stabilizing. In certain embodiments, the protein is an enzyme. In general, glycosylated enzymes may be more stable than their unglycosylated counterparts.

In one aspect of this invention, the target protein is unglycosylated. The new glycosylation method does not require the use of either eukaryotic expression platforms or the presence of existing N-linked glycosylation sites in the target protein. In a unique aspect of this invention, the target protein may already be N-glycosylated or O-glycosylated in the traditional sense, thereby providing a hyper-glycosylated protein product. This method of in vitro glycoprotein manufacturing may provide a more direct, robust, and scalable method than those currently employed, such as enzymatic modification of existing glycans or genetic manipulation of the cellular glycosylation machinery. Existing approaches may suffer from poor scalability and a high degree of difficulty. These problems are absent in the present invention.

This invention describes a new method for glycosylating proteins that does not require the presence of a sequeon or glycosyltransfer consensus glycosylation amino acid recognition sequence.[1, 3, 13] In one embodiment, this invention uses the $N^\varepsilon$-amino group of the lysine sidechain as a nucleophile to covalently bond to a carbohydrate oxazoline to form one or more amidine moieties (Schemes 1 and 2). The method is mild, and allows for the transfer of multiple glycans to a target protein. A protein may contain one or more lysine residues that are available to undergo modification by glycosylation.

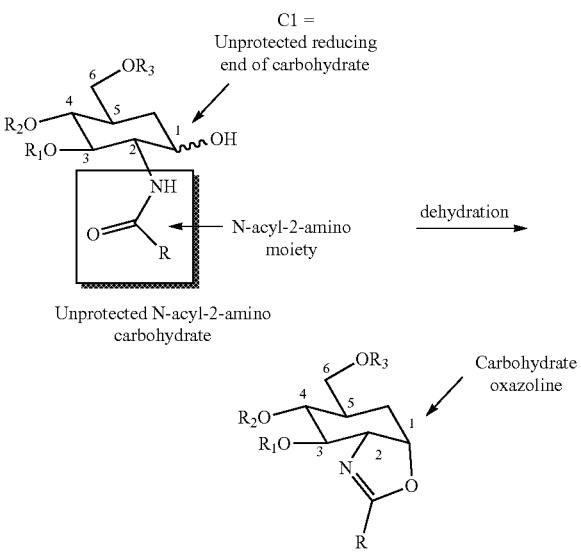

Scheme 1 shows the numbering of the parent N-acyl-2-amino carbohydrate depicting the free reducing end at C1 (i.e. a hemiacetylic hydroxyl). The dehydration of the N-acyl-2-amino moiety and the C1 hydroxyl forms the carbohydrate oxazoline in aqueous media. Dehydration can be accomplished in basic media using published methods.[12, 21-22] Bases such as triethylamine and solid $Na_3PO_4$ may be used to promote dehydration. All carbohydrate manipulations may take place in aqueous solution, including buffered aqueous solutions, in the absence of any protecting group chemistries. In one embodiment, this first reaction of forming a carbohydrate oxazoline takes place over about 24 hours. In a preferred embodiment, this first reaction of forming a carbohydrate oxazoline takes place from about one to six hours.

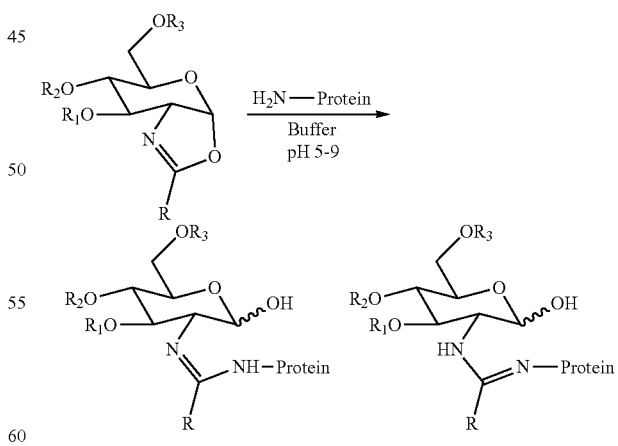

In one embodiment, a non-obvious neutralization step of the oxazoline modified glycan with bicine (or any suitable acid or buffer within a preferred pH range) prior to coupling to the target protein (e.g. an enzyme), is required. Most proteins, and in particular enzymes, are not generally tolerant of pH values much higher than pH of about 8.5, at which point structural unfolding, and covalent modifications begin to occur. Since formation of the oxazoline requires significant quantities (7.5 molar excess) of base, said base must be either removed by filtration and/or neutralized with a concentrated buffer solution to prevent exposing the oxazoline or the target protein to a pH above 8.5 when the two species are combined. In a preferred embodiment, the pH of the oxazoline containing solution is adjusted to maintain optimal enzyme catalytic function. The preferred pH range for the reaction of the oxazoline with a protein target, such as an enzyme, is pH 5 to pH 9. A more preferred pH range is pH 6.5 to pH 8.5. The most preferred range is pH 7.0 to pH 8.0. Reactions are driven to completion by the action of Le Chatliere's Principle regardless of the pH.

Prototypical reaction of the parent N-acyl-2-amino carbohydrate oxazoline with a nucleophilic amino sidechain moiety on a protein yields the carbohydrate modified protein through the two tautomeric bonding schemes as depicted in Scheme 2. These tautomers may be in equilibrium with each other and other structures related to these two canonical structures." In one embodiment, the amino acids that contain a nucleophilic amino sidechain moiety are selected from the group consisting of lysine, arginine and histidine. In a preferred embodiment, the amino acid that contains a nucleophilic amino sidechain moiety is lysine. In one embodiment, this second reaction takes place from about 2 hours to about 96 hours. In another embodiment, the temperature of this second reaction is from about 0° C. to about 37° C. In a preferred embodiment, the temperature of this second reaction is from about 4° C. to about 25° C.

In another embodiment, the invention includes the steps of first reacting a carbohydrate having an N-acyl-2-amino group on the reducing end thereof with a dehydrating agent to form an oxazoline moiety on the reducing end of a carbohydrate, and then reacting said oxazoline carbohydrate with a starting protein. In a preferred embodiment, the method of claim 13, including the step of carrying out said first reaction for a period from about 1-6 hours, and carrying out said protein/oxazoline carbohydrate reaction for a period of from about 2 hours to 96 hours.

There is no stereochemical requirement at C2, C3, C4, C5 and C6 of the carbohydrate, and the N-acyl moiety may be either equatorially or axially disposed and still result in formation of an oxazoline. The R moiety on the acyl group is defined herein.

Thus, in one embodiment of this invention, carbohydrates with an N-acylglucosamine saccharide at the reducing end can covalently bond with a target protein (Scheme 2). In another embodiment of this invention, carbohydrates with an N-acylmannosamine saccharide at the reducing end can covalently bond with a target protein (Scheme 2). In another embodiment of this invention, carbohydrates with an N-acylgalactosamine saccharide at the reducing end can covalently bond with a target protein (Scheme 2). In another embodiment of the invention, the R group is not limited to methyl (Scheme 2).

One of ordinary skill in the art will recognize that the C3, C4 and C6 hydroxyl moieties on the parent N-acyl-2-amino carbohydrate may be further substituted with other carbohydrates to form disaccharide structures, and that free C2, C3, C4 and C6 hydroxyls within disaccharide structures may be further substituted to form larger oligosaccharides. The scope of $R_1$, $R_2$ and $R_3$ is defined herein. $R_1$, $R_2$ and $R_3$ are independently selected from the group consisting of H and saccharides.

The carbohydrate or saccharide according to the present invention is not limited by its source or origin, and encompasses those obtained from natural origins including those from human and other mammalian sources, those produced by genetically engineered animal cells, plant cells, microorganisms, and other cells, those enzymatically manufactured, those manufactured by fermentation processes, those artificially synthesized by chemical processes and others. The carbohydrate or saccharide may encompass monosaccharides, disaccharides, oligosaccharides, and polysaccharides, so long as the reducing end saccharide moiety is unprotected on C1 (i.e. contains a hemiacetalic hydroxyl) and contains an N-acyl-2-amino moiety. Examples of N-acyl-2-amino monosaccharides include, but are not limited to, N-acetylglucosamine, N-acylglucosamine, N-acetylgalactosamine, N-acylgalactosamine, N-acetylmannosamine, N-acylmannosamine, N-acetyllallosamine, N-acylallosamine, (2S,3S,4R,5R,6R)-5-acetamido-3,4,6-trihydroxytetrahydro-2H-pyran-2-carboxylic acid, (2S,3R,4R,5R,6R)-5-acetamido-3,4,6-trihydroxytetrahydro-2H-pyran-2-carboxylic acid, (2S,3S,4S,5R,6R)-5-acetamido-3,4,6-trihydroxytetrahydro-2H-pyran-2-carboxylic acid, (2R,3S,4R,5R,6R)-5-acetamido-3,4,6-trihydroxytetrahydro-2H-pyran-2-carboxylic acid, (2S,3S,4R,5R,6R)-5-acyl-3,4,6-trihydroxytetrahydro-2H-pyran-2-carboxylic acid, (2S,3R,4R,5R,6R)-5-acyl-3,4,6-trihydroxytetrahydro-2H-pyran-2-carboxylic acid, (2S,3S,4S,5R,6R)-5-acyl-3,4,6-trihydroxytetrahydro-2H-pyran-2-carboxylic acid, (2R,3S,4R,5R,6R)-5-acyl-3,4,6-trihydroxytetrahydro-2H-pyran-2-carboxylic acid, (2S,3S,4R,5R,6R)-5-(2-(carboxymethoxy)acetamido)-3,4,6-trihydroxytetrahydro-2H-pyran-2-carboxylic acid, 2-(2-oxo-2-(((2R,3R,4R,5S,6R)-2,4,5-trihydroxy-6-(hydroxymethyl)tetrahydro-2H-pyran-3-yl)amino)ethoxy)acetic acid, (2S,3R,4R,5R,6R)-5-(2-(carboxymethoxy)acetamido)-3,4,6-trihydroxytetrahydro-2H-pyran-2-carboxylic acid, 2-(2-oxo-2-(((2R,3R,4R,5S,6R)-2,4,5-trihydroxy-6-(hydroxymethyl)tetrahydro-2H-pyran-3-yl)amino)ethoxy)acetic acid, (2S,3S,4S,5R,6R)-5-(2-(carboxymethoxy)acetamido)-3,4,6-trihydroxytetrahydro-2H-pyran-2-carboxylic acid, 2-(2-oxo-2-(((2R,3R,4R,5S,6R)-2,4,5-trihydroxy-6-(hydroxymethyl)tetrahydro-2H-pyran-3-yl)amino)ethoxy)acetic acid, (2R,3S,4R,5R,6R)-5-(2-(carboxymethoxy)acetamido)-3,4,6-trihydroxytetrahydro-2H-pyran-2-carboxylic acid, 2-(2-oxo-2-(((2R,3R,4R,5S,6R)-2,4,5-trihydroxy-6-(hydroxymethyl)tetrahydro-2H-pyran-3-yl)amino)ethoxy)acetic acid, and derivatives and modified derivatives thereof. In a preferred embodiment, the monosaccharide has a molecular weight of at least about 200 Daltons to about 500 Daltons.

Examples of disaccharides include, but are not limited to, N-acetyllactosamine, N-acylactosamine, N,N'-diacetyl chitobiose, N,N'-diacyl chitobiose, hyaluronic acid disaccharide, keratin disaccharide, keratin sulfate disaccharide, chondroitin disaccharide, chondroitin sulfate disaccharide, dermatan disaccharide, dermatan sulfate disaccharide, heparin disaccharide, and derivatives thereof so long as the reducing end of the disaccharide is unprotected on C1 and contains an N-acyl-2-amino moiety. The disaccharides of the present invention may further include those disaccharides that are isolated or synthesized wherein any C3, C4 or C6 free hydroxyl of an N-acyl-2-amino monosaccharide is further substituted with a single monosaccharide (at $R_1$, $R_2$ or $R_3$ in Schemes 1 and 2). Such monosaccharides include, but are not limited to, N-acyl 2-amino monosaccharides, glucose, galactose, allose, mannose, idose, fructose, fucose, xylose, arabinose, glucuronic acid, iduronic acid, neuraminic acid, sialic acid, and derivatives and modified derivatives thereof.

The oligosaccharides of the current invention encompass those molecules composed of three or more monosaccharide units linked together at any free hydroxyl in the ordinary sense, either in a linear or branched manner, and are usually composed of 3 to 30 monosaccharide units, but in some instances may contain thousands of monosaccharide units. In particular, the oligosaccharides of the present invention may further include those oligosaccharides that are isolated or synthesized wherein any C3, C4 or C6 free hydroxyl of an N-acyl-2-amino monosaccharide is substituted with a single monosaccharide (depicted as $R_1$, $R_2$ and $R_3$ in FIGS. 1 and 2), and any other C2, C3, C4 or C6 free hydroxyl may be further substituted with one or more monosaccharides. Examples of the oligosaccharide include those discovered in a wide range of organisms such as animals, plants (including seaweeds), insects, microorganisms, and others, and include, but are not limited to, homooligomers of N-acetylglucosamine, chitin, partially deacetylated chitin, and other N-acyl-2-amino monosaccharides, heterooligomers composed of two or more different monosaccharides independently selected from the groups consisting of glucose, galactose, mannose, glucosamine, fructose, N-acyl-2-amino monosaccharides, iduronic acid, neuraminic acid, and sialic acid so long as the reducing end unit is unprotected (i.e. contains a hemiacetalic hydroxyl) and contains an N-acyl-2-amino moiety. Other representative oligosaccharides include hyaluronic acid, keratin, keratin sulfate, chondroitin, chondroitin sulfate, dermatan, dermatan sulfate, heparin, N-acetyllactosamine oligosaccharide, N-acetylchitotriose, N-acetylchitotetraose, and N-acetylchitopentose, chitin, including partially deacetylated chitin, native N-glycan cores, high-mannose N-glycans, hybrid N-glycans, complex N-glycans, and derivatives thereof.

Examples of native N-glycan cores include, but are not limited to, Man3 and Man3F. Examples of high-mannose N-glycans include, but are not limited to, Man-5, Man-6, Man-7, Man-8, and Man-9. Examples of hydride N-glycans include, but are not limited, those carbohydrates wherein the GlcNAc terminates one branch of the N-glycan core, and a mannose terminates another branch of the N-glycan core. Examples of complex N-glycans include, but are not limited to, GO-N, GO, GOF-N, GOF, GOFB, G1, G1F, G2, G2F, G2FB, G1S1($\alpha$2,3), G1S1($\alpha$2,6), G1FS1($\alpha$2,3), G1FS1($\alpha$2,6), G2S1($\alpha$2,3), G2S1($\alpha$2,6), G2FS1($\alpha$2,3), G2FS1($\alpha$2,6), G2S2($\alpha$2,3), G2S2($\alpha$2,6), G2FS2($\alpha$2,3), G2FS2($\alpha$2,6), G2F with 2-$\alpha$-Gal, A3, G3, G3S3($\alpha$2,6), A4, G4, Lewis A, Lewis B, Lewis X, Lewis Y, sialyl Lewis A, and sialyl Lewis X. The nomenclature used to describe the N-glycans would be known to one skilled in the art. With the exception of the Lewis antigens, all native N-glycan cores, high-mannose N-glycans, hybrid N-glycans, and complex N-glycans contain a $Man_3GlcNAc_2$ core, which may be optionally fucosylated or xylosylated.

The term "modified carbohydrate" (or "modified derivative thereof") used herein may refer to those modified through any process of isolation, separation and purification from naturally-occurring sources and origins, those that have been enzymatically modified, those that have been chemically modified, those that have been modified by biochemical means, including microorganisms, wherein such modifications may comprise those known in the field of glycoscience, for example, hydrolysis, oxidation, reduction, esterification, acylation, amination, etherification, nitration, dehydration, glycosylation, phosphorylation, and sulfation.

The applicable C1-hemiacetal hydroxyl and N-acyl-2-amino-bearing carbohydrate used as the starting material in implementing the present invention include carbohydrate molecules having an N-acylamino group at position 2 on the reducing end side. Preferred carbohydrates have an acetamido group at position 2 on the reducing end side of a monosaccharide, including, for example, N-acetylglucosamine, N-acetylgalactosamine, and N-acetylmannosamine, and oligosaccharides in which the reducing end is selected from N-acetylglucosamine, N-acetylgalactosamine, and other N-acyl-2-amino monosaccharides. In case of disaccharides and oligosaccharides, preferred examples of the carbohydrate include N-acetylactosamine, N,N'-diacetylchitobiose, hyaluronic acid disaccharide, other glycosaminoglycan disaccharides. Preferred oligosaccharides include hyaluronic acid, keratin, keratin sulfate, chondroitin, chondroitin sulfate, dermatan, dermatan sulfate, heparin, poly-N-acetyllactosamine, N-acetylchitotriose, N-acetylchitotetraose, and N-acetylchitopentose, chitin, including partially deacetylated chitin, high-mannose N-glycans, hybrid N-glycans, and complex N-glycans. In a more preferred embodiment, the linear oligosaccharide is hyaluronic acid.

Linear oligosaccharides such as chitin, including partially deacetylated chitin, hyaluronic acid, keratin, keratin sulfate, chondroitin, chondroitin sulfate, dermatan, dermatan sulfate, and heparin can achieve molecular weights as much as 5,000,000 Daltons. Preferred sizes of these oligosaccharides include, but are not limited to, those with molecular weights of at least about 500 Daltons, at least about 1,000 Daltons, at least about 1,500 Daltons, at least about 3,500 Daltons, at least about 5,000 Daltons, at least about 10,000 Daltons, at least about 20,000 Daltons, at least about 25,000 Daltons, at least about 33,000 Daltons, at least about 50,000 Daltons, and at least about 100,000 Daltons. In another embodiment, preferred sizes of these oligosaccharides include, but are not limited to, those molecular weights that are less than about 6,000 Daltons, and less than about 50,000 Daltons.

Branched oligosaccharides such as high-mannose N-glycans, hybrid N-glycans, and complex N-glycans have molecular weights that are typically under 10,000 Daltons. Preferred sizes of these oligosaccharides include, but are not limited to, those with molecular weights of from about 500 Daltons to about 10,000 Daltons. A more preferred size of these oligosaccharides is from about 800 Daltons to about 5,000 Daltons. A most preferred size of these oligosaccharides is from about 800 Daltons to about 4500 Daltons.

Each R is individually and independently C1-C6 alkyl, branched C3-C8 alkyl, —$(CH_2)_m$—CN, —$(CH_2)_m$OR6, —$(CH_2)_m$—$CO_2H$, —$(CH_2)_m$—$CO_2R6$, —$(CH_2)_m$—NR6(R7), —$(CH_2)_m$—S(O)$_n$—C1-C6 alkyl, —$(CH_2)_m$—C(O)NR6(R7), —$(CH_2)_m$—$CO_2$—C4-C6 heterocyclyl, —$(CH_2)_m$—C4-C6 heterocyclyl, —$(CH_2)_m$—$CO_2$—C4-C6 heteroaryl, or —$(CH_2)_m$—C4-C6-heteroaryl, wherein each alkyl may optionally contain an ether linkage and, wherein each alkyl is optionally substituted with one or two C1-C6 alkyl;

each R6 and R7 is individually and independently H, C1-C6 alkyl, or branched C3-C8 alkyl;

each m is individually and independently 1, 2, 3, 4, or 5;

each n is individually and independently 0, 1, or 2;

Structural, chemical and stereochemical definitions are broadly taken from IUPAC recommendations, and more specifically from Glossary of Terms used in Physical Organic Chemistry (IUPAC Recommendations 1994) as summarized by Müller, P. Pure Appl. Chem. 1994, 66, pp. 1077-1184 and Basic Terminology of Stereochemistry (IUPAC Recommendations 1996) as summarized by Moss, G. P. Pure Appl. Chem. 1996, 68, pp. 2193-2222.

For convenience, certain terms employed in the specification, examples and claims are collected here. Unless defined otherwise, all technical and Scientific terms used in this dis closure have the same meanings as commonly understood by one of ordinary skill in the art to which this disclosure belongs. The initial definition provided for a group or term provided in this disclosure applies to that group or term throughout the present disclosure in The term "alkyl" as used herein refers to a straight chain alkyl, wherein alkyl chain length is indicated by a range of numbers. In exemplary embodiments, "alkyl" refers to an alkyl chain as defined above containing 1, 2, 3, 4, 5, or 6 carbons (i.e., C1-C6 alkyl). Examples of an alkyl group include, but are not limited to, methyl, ethyl, propyl, butyl, pentyl, and hexyl.

The term "branched alkyl" as used herein refers to an alkyl chain wherein a branching point in the chain exists, and the total number of carbons in the chain is indicated by a range of numbers. In exemplary embodiments, "branched alkyl" refers to an alkyl chain as defined above containing 3, 4, 5, 6, 7, or 8 carbons (i.e., branched C3-C8 alkyl). Examples of a branched alkyl group include, but are not limited to, iso-propyl, iso-butyl, secondary-butyl, and tertiary-butyl.

The term "heterocycle" or "heterocyclyl" as used herein refers to a cyclic hydrocarbon, wherein at least one of the ring atoms is an O, N, or S, wherein the number of ring atoms is indicated by a range of numbers. Heterocyclyl moieties as defined herein have C or N bonding sites. For example, in some embodiments, a ring N atom from the heterocyclyl is the bonding atom of the heterocylic moiety. In exemplary embodiments, "heterocyclyl" refers to a cyclic hydrocarbon as described above containing 4, 5, or 6 ring atoms (i.e., C4-C6 heterocyclyl). Examples of a heterocycle group include, but are not limited to, aziridine, oxirane, thirane, azetidine, oxetane, thietane, pyrrolidine, tetrahydrofuran, pyran, thiopyran, thiomorpholine, thiomorpholine S-oxide, thiomorpholine S-dioxide, oxazoline, tetrahydrothiophene, piperidine, tetrahydropyran, thiane, imidazolidine, oxazolidine, thiazolidine, dioxolane, dithiolane, piperazine, oxazine, dithiane, and dioxane.

The term "heteroaryl" as used herein refers to a cyclic hydrocarbon, where at least one of the ring atoms is an O, N, or S, the ring is characterized by delocalized at electrons (aromaticity) shared among the ring members, and wherein the number of ring atoms is indicated by a range of numbers. Heteroaryl moieties as defined herein have C or N bonding hands. For example, in some embodiments, a ring N atom from the heteroaryl is the bonding atom of the heteroaryl moiety. In exemplary embodiments, "heteroaryl" refers to a cyclic hydrocarbon as described above containing 5 or 6 ring atoms (i.e., C5-C6 heteroaryl). Examples of a heteroaryl group include, but are not limited to, pyrrole, furan, thiene, oxazole, thiazole, isoxazole, isothiazole, imidazole, pyrazole, oxadiazole, thiadiazole, triazole, tetrazole, pyridine, pyrimidine, pyrazine, pyridazine, and triazine. The term "substituted in connection with a moiety as used herein refers to a further substituent which is attached to the moiety at any acceptable location on the moiety. Unless otherwise indicated, moieties can bond through a carbon, nitrogen, oxygen, sulfur, or any other acceptable atom.

The term "substituted" in connection with a moiety as used herein refers to a further substituent which is attached to the moiety at any acceptable location on the moiety. Unless otherwise indicated, moieties can bond through a carbon, nitro gen, oxygen, sulfur, or any other acceptable atom.

The term "tautomer" as used herein refers to compounds produced by the phenomenon where in a proton of one atom of a molecule shifts to another atom. See March, Advanced Organic Chemistry: Reactions, Mechanisms and Structures, 4th Ed., John Wiley & Sons, pp. 69-74 (1992). Tautomerism is defined as isomerism of the general form:

where the isomers (called tautomers) are readily interconvertible; the atoms connecting the groups X, Y and Z are typically any of C, H, O, or S, and G is a group which becomes an electrofuge or nucleofuge during isomerization. The most common case, when the electrofuge is $H^+$, is also known as "prototropy". Tautomers are defined as isomers that arise from tautomerism, independent of whether the isomers are isolable.

The present invention is suitable for the modification of proteins, and may find application in a variety of situations. More specifically, this invention is suitable for the modification of enzymes. Preferred enzyme classes are oxidase proteins, oxidoreductase proteins, dehydrogenase proteins, and combinations thereof.

Within the classification of oxidase proteins, the preferred targets are those used in human health monitoring applications. Oxidase enzymes that may benefit from glycosylation using this invention include, but are not limited to, malate oxidases, EC 1.1.3.3, hexose oxidases, EC 1.1.3.5, aryl-alcohol oxidases, EC 1.1.3.7, L-gluconolactone oxidases, EC 1.1.3.8, pyranose oxidases, EC 1.1.3.10, L-sorbose oxidases, EC 1.1.3.11, pyridoxine 4-oxidases, EC 1.1.3.12, (S)-2-hydroxy-acid oxidases, EC 1.1.3.15, ecdysone oxidases, EC 1.1.3.16, secondary-alcohol oxidases, EC 1.1.3.18, 4-hydroxymandelate oxidases, EC 1.1.3.19, long-chain-alcohol oxidases, EC 1.1.3.20, thiamine oxidases, EC 1.1.3.23, hydroxyphytanate oxidases, EC 1.1.3.27., N-acyl-hexosamine oxidases, EC 1.1.3.29, polyvinyl-alcohol oxidases, EC 1.1.3.30, D-Arabinono-1,4-lactone oxidases, EC 1.1.3.37, vanillyl-alcohol oxidases, EC 1.1.3.38, D-mannitol oxidases, EC 1.1.3.40, alditol oxidases, EC 1.1.3.41, choline dehydrogenase, EC 1.1.99.1, gluconate 2-dehydrogenase EC 1.1.99.3, glucooligosaccharide oxidases, EC 1.1.99.B3, alcohol dehydrogenase, EC 1.1.99.8, cellobiose dehydrogenase, EC 1.1.99.18, aldehyde oxidases, EC 1.2.3.1, glyoxylate oxidases, EC 1.2.3.5, indole-3-acetaldehyde oxidases, aryl-aldehyde oxidases, EC 1.2.3.9, retinal oxidases, EC 1.2.3.11, abscisic-aldehyde oxidases, EC 1.2.3.14, aldehyde ferredoxin oxidoreductase, EC 1.2.7.5, indolepyruvate ferredoxin oxidoreductase, EC 1.2.7.8, aldehyde dehydrogenase, EC 1.2.99.7, dihydroorotate oxidases, EC 1.3.3.1, acyl-CoA oxidases, EC 1.3.3.6, dihydrouracil oxidases, EC 1.3.3.7, tetrahydroberberine oxidases, EC 1.3.3.8, tryptophan alpha, beta-oxidases, EC 1.3.3.10, L-galactonolactone oxidases, EC 1.3.3.12, acyl-CoA dehydrogenase, EC 1.3.99.3, Isoquinoline-1-oxidoreductase, EC 1.3.99.16, quinaldate 4-oxidoreductase, EC 1.3.99.18, D-aspartate oxidases, EC 1.4.3.1, L-amino-acid oxidases, EC 1.4.3.2, monoamine oxidases, EC 1.4.3.4, pyridoxal 5'-phosphate synthase, EC 1.4.3.5, D-glutamate oxidases, EC 1.4.3.7, ethanolamine oxidases, EC 1.4.3.8; putrescine oxidases, EC 1.4.3.10, cyclohexylamine oxidases, EC 1.4.3.12, protein-lysine 6-oxidases, EC 1.4.3.13, D-glutamate(D-aspartate) oxidases, EC 1.4.3.15, L-lysine 6-oxidases, EC 1.4.3.20, primary-amine oxidases, EC 1.4.3.21, 7-chloro-L-tryptophan oxidases, EC 1.4.3.23, N-methyl-L-amino-acid oxidases, EC 1.5.3.2, non-specific polyamine oxidases, EC 1.5.3.B2, N8-acetylspermidine oxidases (propane-1,3-diamine-forming), EC 1.5.3.B3, N6-methyl-lysine oxidases, EC 1.5.3.4, polyamine oxidases (propane-1,3-diamine-forming), EC 1.5.3.B4, N1-acetylpolyamine oxidases, EC 1.5.3.B5, spermine oxidases, EC 1.5.3.B6, pipecolate oxidases, EC 1.5.3.7, dimethylglycine oxidases, EC 1.5.3.10, polyamine oxidases, EC 1.5.3.11, Dihydrobenzophenanthridine oxidases, EC 1.5.3.12, NAD(P)H oxidases, EC 1.6.3.1, urate oxidases, EC 1.7.3.3; 3-aci-nitropropanoate oxidases, sulfite oxidases, EC 1.8.3.1, methanethiol oxidases, EC 1.8.3.4; phenylcysteine oxidases, EC 1.8.3.5, L-ascorbate oxidases, EC 1.10.3.3, 3-hydroxyanthranilate oxidases, EC 1.10.3.5, rifamycin-B oxidases, EC 1.10.3.6, superoxide dismutase, EC 1.15.1.1, reticuline oxidases, EC 1.21.3.3, lactate oxidases, L-EC 1.1.3.15, D-amino acid oxidases, EC 1.4.3.3, (S)-6-hydroxynicotine oxidases, EC 1.5.3.5, (R)-6-hydroxynicotine oxidases, EC 1.5.3.6, alcohol oxidases, EC 1.1.3.13, pyruvate oxidases, EC 1.2.3.3, glucose oxidases, EC 1.1.3.4), L-glutamate oxidases, EC 1.4.3.11, acyl coenzyme A oxidases, EC 1.3.3.6, choline oxidases, EC 1.1.3.17, glutathione sulfhydryl oxidases, EC 1.8.3.3, glycerolphosphate oxidases, EC 1.1.3.21, sarcosine oxidases, EC 1.5.3.1, xanthine oxidases, EC 1.1.3.22, oxalate oxidases, EC 1.2.3.4, co-factor(s)=$Mn^{2+}$; cholesterol oxidases, EC 1.1.3.6, gamma-glutamyl-putrescine oxidases, EC undefined, obtained from *Escherichia coli* K12, capable of oxidizing GABA; GABA oxidases, EC undefined, obtained from: *Penicillium* sp. KAIT-M-117, histamine oxidases (diamine oxidases), EC 1.4.3.22, nucleoside oxidases, EC 1.1.3.39, L-lysine oxidases, EC 1.4.3.14, L-aspartate oxidases, EC 1.4.3.16, glycine oxidases, EC 1.4.3.19, galactose oxidases, EC 1.1.3.9, laccases (EC 1.1.3.4), tyrosinases (1.14.18.1), sulfite oxidases, tyramine oxidases, and NADH oxidases (1.11.1.1).

Preferred members of the oxidase class of enzymes include, but are not limited to, lactate oxidases (EC 1.1.3.15), D-amino acid oxidases (EC 1.4.3.3), (S)-6-hydroxynicotine oxidases (EC 1.5.3.5), (R)-6-hydroxynicotine oxidases (EC 1.5.3.6), alcohol oxidases (EC 1.1.3.13), pyruvate oxidases (EC 1.2.3.3), glucose oxidases (EC 1.1.3.4), glutamate oxidases (EC 1.4.3.11), acyl coenzyme A oxidases (EC 1.3.3.6), choline oxidases (EC 1.1.3.17), glutathione sulfhydryl oxidases (EC 1.8.3.3), glycerolphosphate oxidases (EC 1.1.3.21), sarcosine oxidases (EC 1.5.3.1), xanthine oxidases (EC 1.1.3.22), oxalate oxidases (EC 1.2.3.4), cholesterol oxidases (EC 1.1.3.6), gamma alpha-butyric acid (GABA) oxidases (EC undefined), histamine oxidases (diamine oxidases, EC 1.4.3.22), nucleoside oxidases (EC 1.1.3.39), L-lysine oxidases (EC 1.4.3.14), L-aspartate oxidases (EC 1.4.3.16), glycine oxidases (EC 1.4.3.19), NADH oxidases (EC 1.11.1.1) and galactose oxidases (EC 1.1.3.9).

Most preferred members of the oxidase class of enzymes include, but are not limited to, lactate oxidases (EC 1.1.3.15), alcohol oxidases (EC 1.1.3.13), glucose oxidases (EC 1.1.3.4), glutamate oxidases (EC 1.4.3.11), choline oxidases (EC 1.1.3.17), sarcosine oxidases (EC 1.5.3.1), xanthine oxidases (EC 1.1.3.22), oxalate oxidases (EC 1.2.3.4), cholesterol oxidases (EC 1.1.3.6), histamine oxidases (diamine oxidases, EC 1.4.3.22), glycine oxidases (EC 1.4.3.19), NADH oxidases (EC 1.11.1.1) and galactose oxidases (EC 1.1.3.9).

Dehydrogenase enzymes may benefit from glycosylation using this invention. Within the classification of dehydrogenase proteins, the preferred targets are those used human health monitoring applications include, but are not limited to, alcohol dehydrogenases (EC 1.1.1.1), glucose hydrogenases (EC 1.1.1.47, L-lactate dehydrogenases (1.1.1.27), D-lactate dehydrogenases (1.1.1.28), cortisol dehydrogenases (1.1.1.146), glutamate dehydrogenases (1.4.1.2), fructose dehydrogenases (EC 1.1.99.11), glycerol 3-phosphate dehydrogenases (1.1.1.8), formaldehyde dehydrogenases (EC 1.1.1.284 and EC 1.2.1.46), aldehyde dehydrogenases (EC 1.2.1.5), alanine dehydrogenases (EC 1.4.1.1), formate dehydrogenases (EC 1.2.1.2), galactose hydrogenases(EC 1.1.1.48), glycerol dehydrogenases (EC 1.1.1.6), glucose-6-phosphate dehydrogenases (EC 1.1.1.49), 3-hydroxybutyrate dehydrogenases (EC 1.1.1.30), 3-alpha-hydroxysteroide dehydrogenases (EC 1.1.1.50), isocitrate dehydrogenases (EC 1.1.1.42), inositol dehydrogenases (EC 1.1.18), L-leucine dehydrogenases (EC 1.4.1.9), L-malate dehydrogenases (EC 1.1.1.37), and sorbitol dehydrogenases (EC 1.1.1.14).

Preferred members of the dehydrogenase class of enzymes include, but are not limited to, alcohol dehydrogenases (EC 1.1.1.1), glucose hydrogenases (EC 1.1.1.47, L-lactate dehydrogenases (1.1.1.27), cortisol dehydrogenases (1.1.1.146), glutamate dehydrogenases (1.4.1.2), galactose hydrogenases(EC 1.1.1.48), glycerol dehydrogenases (EC 1.1.1.6), glucose-6-phosphate dehydrogenases (EC 1.1.1.49), 3-hydroxybutyrate dehydrogenases (EC 1.1.1.30), L-malate dehydrogenases (EC 1.1.1.37), and sorbitol dehydrogenases (EC 1.1.1.14).

Most preferred members of the dehydrogenase class of enzymes include, but are not limited to, alcohol dehydrogenases (EC 1.1.1.1), glucose hydrogenases (EC 1.1.1.47, L-lactate dehydrogenases (1.1.1.27), cortisol dehydrogenases (1.1.1.146), galactose hydrogenases(EC 1.1.1.48), glycerol dehydrogenases (EC 1.1.1.6), glucose-6-phosphate dehydrogenases (EC 1.1.1.49), 3-hydroxybutyrate dehydrogenases (EC 1.1.1.30), L-malate dehydrogenases (EC 1.1.1.37), and sorbitol dehydrogenases (EC 1.1.1.14).

The present invention is also suitable for use with enzymes that are modified with fusion partners to aid in expression, stabilization, and/or solubility. Fusion partners to the oxidase, oxidoreductase and dehydrogenase proteins include, but are not limited to, green fluorescent protein (GFP), glutathione S-transferase (GST), maltose-binding protein (MBP), iGg binding domain of Protein G (GB1), Protein A (PA), thioredcoxin (TRX), cyclomaltodextrin glucanotransferase (CMDGT), small ubiquitin-like modifier (SUMO), galactose binding protein (GBP), cellulose binding domain (CBD), calmodulin binding peptide (CBP), bacterial transcription termination/anti termination protein (NusA), growth differentiating factor-8 (GDF8), and ubiquitin (Ub). One skilled in the art will recognize that said fusion proteins may be N-terminal or C-terminal to the catalytic domains of the oxidase, oxidoreductase and dehydrogenase proteins, and may include an optional linker between the two protein domains.

In another embodiment, the attachment of a N-acyl-2-amino carbohydrate oxazoline with a nucleophilic amino sidechain moiety on a protein yields the carbohydrate modified protein with an alternative glycosylation pattern to existing, natural glycosylation patterns. This altered glycosylation pattern has the potential of conferring new properties to the target protein, such as enhanced stability of an enzyme. In addition, the ability to add oligosaccharides to proteins that are naturally glycosylated, such as glucose oxidase, offers the possibility to hyper-glycosylate said proteins. This is especially important for the stabilization of enzymes, most especially oxidase, oxidoreductase, and dehydrogenase enzymes, that may be useful in human health monitoring applications. Another embodiment of this invention allows for the modification a protein without the removal of native glycans, said native glycans that are known to be stabilizing to a protein.

Existing N-linked glycosylation involves the use of asparagine side chains as the attachment point for the glycan moiety. In one embodiment of this invention, sidechains that are traditionally non-glycosylated such as lysine, arginine, and histidine are glycosylated. Since this strategy is orthogonal to natural glycosylation methods, proteins, such as glucose oxidase that are natively glycosylated, can be further glycosylated to produce a hyper-glycosylated entity that may have beneficial characteristics including stabilization and controlled immunogenicity. Many important proteins are naturally glycosylated, and cannot be further glycosylated on other sites within the properly folded protein structure using natural and prior art methods. This invention provides a rational method to further glycosylate said proteins, thereby stabilizing glycoproteins, such as glucose oxidase, without compromising the structure and function, i.e. catalytic ability, of the protein.

One skilled in the art will recognize that protein structure is the three-dimensional arrangement of atoms in one or more amino acid-chain molecules. To be able to perform biological functions, proteins fold into one or more specific spatial conformations driven by a number of non-covalent interactions including hydrogen bonding, ionic interactions, Van der Waals forces, and hydrophobic packing, thereby forming an ensemble. A protein may undergo reversible structural changes in performing its function, which for an enzyme includes catalytic action on a substrate or substrates to produce a product or products. A protein will not function without the correct structure. For example, an enzyme is in its substantially active form when it is able to catalyze a physical or physiochemical process, and the results of this process are observable. An enzyme is unable to perform catalysis when the structure is altered such that the enzyme is no longer able to facilitate one or more steps of the catalytic process, and is therefore deemed inactive. Activity and function depend on the proper specific spatial conformations being occupied, and observed activity is a direct indication of proper structure. Thus, modifications of a protein, including enzymes, that do not substantially alter function by definition do not substantially alter specific spatial conformations. Changes to function without changes to protein structure are mutually exclusive. The stability and therefore activity of a glycosylated or hyper-glycosylated protein relative to the starting protein can be improved, as reflected by improved longevity of the modified protein's activity. This can be quantified by kinetic and biophysical studies, including accelerated enzymatic stability studies at elevated temperatures herein. In one embodiment, the stabilized enzyme retains at least about 25% more activity compared to the starting enzyme in accelerated stability studies. In a preferred embodiment, the stabilized enzyme retains at least about 33% more activity compared to the starting enzyme in accelerated stability studies. In a more preferred embodiment, the stabilized enzyme retains at least about 50% more activity compared to the starting enzyme in accelerated stability studies. In a most preferred embodiment, the stabilized enzyme retains at least about 75% more activity compared to the starting enzyme in accelerated stability studies.

In another embodiment, the present invention is a glycosylated protein comprising a starting protein having an amino sidechain with a nucleophilic moiety glycosylated with a carbohydrate having an oxazoline moiety on the reducing end thereof, said oxazoline moiety covalently bound with said nucleophilic moiety, said glycosylated protein having a molecular weight of at least about 7500 Daltons, said glycosylated protein substantially retaining the structure and function of said starting protein. More specifically, the present glycosylated protein is a glycosylated enzyme. Preferred enzyme classes are oxidase proteins, oxidoreductase proteins, dehydrogenase proteins, and combinations thereof defined herein.

In a further embodiment, the glycosylated protein utilizes the amino sidechain of the starting protein that is selected from the group comprising the sidechains of lysine, histidine, and arginine. In a preferred embodiment, the amino acid side chain is that of lysine.

In a further embodiment, the glycosylated protein is formed using a carbohydrate of molecular weight of at least about 200 Daltons. In another embodiment, the glycosylated protein is formed using a carbohydrate of molecular weight of at least about 10000 Daltons. In another embodiment, the glycosylated protein is formed using a carbohydrate of molecular weight of at least about 25000 Daltons. In another embodiment, the glycosylated protein is formed using carbohydrate that is selected from group consisting of monosaccharides, disaccharides, linear oligosaccharides, and branched oligosaccharides as described herein.

In another embodiment, the glycosylated protein is formed using linear oligosaccharides such as chitin, including partially deacetylated chitin, hyaluronic acid, keratin, keratin sulfate, chondroitin, chondroitin sulfate, dermatan, dermatan sulfate, and heparin, which can achieve molecular weights as much as 5,000,000 Daltons. Preferred sizes of these oligosaccharides include, but are not limited to, those with molecular weights of at least about 500 Daltons, at least about 1,000 Daltons, at least about 1,500 Daltons, at least about 3,500 Daltons, at least about 5,000 Daltons, at least about 10,000 Daltons, at least about 20,000 Daltons, at least about 25,000 Daltons, at least about 33,000 Daltons, at least about 50,000 Daltons, and at least about 100,000 Daltons. In another embodiment, preferred sizes of these oligosaccharides include, but are not limited to, those molecular weights that are less than about 6,000 Daltons, and less than about 50,000 Daltons.

In another embodiment, the glycosylated protein is formed using branched oligosaccharides such as high-mannose N-glycans, hybrid N-glycans, and complex N-glycans that have molecular weights under 10,000 Daltons. Preferred sizes of these oligosaccharides include, but are not limited to, those with molecular weights of from about 500 Daltons to about 10,000 Daltons. A more preferred size of these oligosaccharides is from about 800 Daltons to about 5,000 Daltons. A most preferred size of these oligosaccharides is from about 800 Daltons to about 4500 Daltons.

Oligosaccharides are available in a range of molecular weights. Linear oligosaccharides based on repeating monosaccharide or disaccharide subunits, such as hyaluronic acid and the other glycosaminoglycans,[27-29] may be obtained as discreet sized species or a distribution of sizes about an average molecular weight. Other linear oligosaccharides include chitin, and partially deacetylated chitin.[30-31] The latter refers to chitin that has been processed to remove some or most of the N-acetyl moieties that modify the glucosamine core. The degree of deacetylation refers to the percentage of N-acetyl moieties removed, with up to 95% removal possible to retain the parent chitin identity. Removal of at least 49% of the acetyl groups within the polymer molecule is required for solubility in water. A range of molecular weights of the parent chitin and the partially deacetylated chitins are possible.

The molecular weight of a linear oligosaccharide may be obtained from a variety of direct and indirect physical characterization methods. These include, but are not limited to, high performance liquid chromatography (HPLC), gel permeation chromatography (GPC), mass spectroscopy (MS) including matrix assisted laser desorption ionization mass spectroscopy (MALDI-MS), ultracentrifuge sedimentation, viscosity, osmotic pressure, and dynamic light scattering (DLS), all of which may be affected by the number, size, or shape of molecules in a matrix, a suspension, or in a solution.[32-35] The molecular weight of high-mannose N-glycans, hybrid N-glycans, and complex N-glycans may be determined in similar manner.

For distributions of different sized oligosaccharides, weight-average molecular weight (Mw) and molecular weight distributions may be determined from ultracentrifuge sedimentation, diffusion, and light scattering. Number-average molecular weight (Mn) and molecular weight distributions may be determined from osmotic pressure and intrinsic viscosity determinations. Optical properties are best reflected in the weight-average molecular weight, while strength properties are best reflected in number-average molecular weight. Mn is the number of monomer molecules divided by the total number of molecules times the monomer mole weight. Mw is the area under the weight distribution curve that is divided into two equal parts. Mn<=Mw.

Weight-average molecular weight, is calculated by the equation $$M_w = \{Sum[(W_i)(MW)_i]\}/\{Sum\ W_i\},$$

where $W_i$ is the weight fraction of each size fraction and $(MW)_i$ is the mean molecular weight of the size fraction. The "weight-average" molecular weight is particularly significant in the analysis of properties such as viscosity, where the weight of the molecules is important. Number-average molecular weight is calculated by the equation $$M_n = \{Sum[(W_i)(MW)_i]\}/\{Sum\ X_i\},$$

where the value $X_i$ is the number of molecules in each size fraction.

In another embodiment, the glycosylated protein has one or both of the tautomeric forms

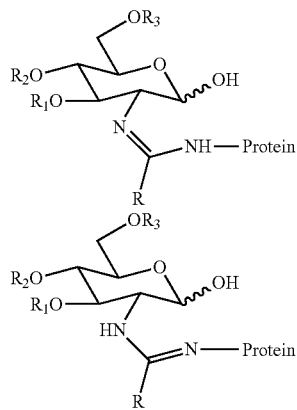

wherein each of $R_1$, $R_2$, and $R_3$ is individually and independently selected from the group consisting of H and saccharides defined herein, and wherein R is selected from the group consisting of C1-C6 alkyl, branched C3-C8 alkyl, —(CH$_2$)$_m$—CN, —(CH$_2$)$_m$OR6, —(CH$_2$)$_m$—CO$_2$H, —(CH$_2$)$_m$—CO$_2$R6, —(CH$_2$)$_m$—NR6(R7), —(CH$_2$)$_m$—S(O)$_n$—C1-C6 alkyl, —(CH$_2$)$_m$—C(O)NR6(R7), —(CH$_2$)$_m$—CO$_2$—C4-C6 heterocyclyl, —(CH$_2$)$_m$—C4-C6 heterocyclyl, —(CH$_2$)$_m$—CO$_2$—C4-C6 heteroaryl, or —(CH$_2$)$_m$—C4-C6-heteroaryl, wherein each alkyl may optionally contain an ether linkage and, wherein each alkyl is optionally substituted with one or two C1-C6 alkyl groups, each R6 and R7 is individually and independently H, C1-C6 alkyl, or branched C3-C8 alkyl, each m is individually and independently 1, 2, 3, 4, or 5, each n is individually and independently 0, 1, or 2.

In a preferred embodiment, the glycosylated protein is selected from the group consisting of glucose oxidases modified with hyaluronic acid, glucose oxidases modified with chitin, glucose oxidases modified with partially deacetylated chitin, glucose oxidases modified with high-mannose N-glycans, glucose oxidases modified with keratin, glucose oxidases modified with keratin sulfate, glucose oxidases modified with chondroitin, glucose oxidases modified with chondroitin sulfate, glucose oxidases modified with dermatan, glucose oxidases modified with dermatan sulfate, glucose oxidases modified with heparin, glucose oxidases modified with hybrid N-glycans, glucose oxidases modified with complex N-glycans, lactate oxidases modified with hyaluronic acid, lactate oxidases modified with chitin, lactate oxidases modified with partially deacetylated chitin, lactate oxidases modified with high-mannose N-glycans, lactate oxidases modified with keratin, lactate oxidases modified with keratin sulfate, lactate oxidases modified with chondroitin, lactate oxidases modified with chondroitin sulfate, lactate oxidases modified with dermatan, lactate oxidases modified with dermatan sulfate, lactate oxidases modified with heparin, lactate oxidases modified with hybrid N-glycans, lactate oxidases modified with complex N-glycans, alcohol oxidases modified with hyaluronic acid, alcohol oxidases modified with chitin, alcohol oxidases modified with partially deacetylated chitin, alcohol oxidases modified with high-mannose N-glycans, alcohol oxidases modified with keratin, alcohol oxidases modified with keratin sulfate, alcohol oxidases modified with chondroitin, alcohol oxidases modified with chondroitin sulfate, alcohol oxidases modified with dermatan, alcohol oxidases modified with dermatan sulfate, alcohol oxidases modified with heparin, alcohol oxidases modified with hybrid N-glycans, alcohol oxidases modified with complex N-glycans, glutamate oxidases modified with hyaluronic acid, glutamate oxidases modified with chitin, glutamate oxidases modified with partially deacetylated chitin, glutamate oxidases modified with high-mannose N-glycans, glutamate oxidases modified with keratin, glutamate oxidases modified with keratin sulfate, glutamate oxidases modified with chondroitin, glutamate oxidases modified with chondroitin sulfate, glutamate oxidases modified with dermatan, glutamate oxidases modified with dermatan sulfate, glutamate oxidases modified with heparin, glutamate oxidases modified with hybrid N-glycans, glutamate oxidases modified with complex N-glycans, choline oxidases modified with hyaluronic acid, choline oxidases modified with chitin, choline oxidases modified with partially deacetylated chitin, choline oxidases modified with high-mannose N-glycans, choline oxidases modified with keratin, choline oxidases modified with keratin sulfate, choline oxidases modified with chondroitin, choline oxidases modified with chondroitin sulfate, choline oxidases modified with dermatan, choline oxidases modified with dermatan sulfate, choline oxidases modified with heparin, choline oxidases modified with hybrid N-glycans, choline oxidases modified with complex N-glycans, sarcosine oxidases modified with hyaluronic acid, sarcosine oxidases modified with chitin, sarcosine oxidases modified with partially deacetylated chitin, sarcosine oxidases modified with high-mannose N-glycans, sarcosine oxidases modified with keratin, sarcosine oxidases modified with keratin sulfate, sarcosine oxidases modified with chondroitin, sarcosine oxidases modified with chondroitin sulfate, sarcosine oxidases modified with dermatan, sarcosine oxidases modified with dermatan sulfate, sarcosine oxidases modified with heparin, sarcosine oxidases modified with hybrid N-glycans, sarcosine oxidases modified with complex N-glycans, xanthine oxidases modified with hyaluronic acid, xanthine oxidases modified with chitin, xanthine oxidases modified with partially deacetylated chitin, xanthine oxidases modified with high-mannose N-glycans, xanthine oxidases modified with keratin, xanthine oxidases modified with keratin sulfate, xanthine oxidases modified with chondroitin, xanthine oxidases modified with chondroitin sulfate, xanthine oxidases modified with dermatan, xanthine oxidases modified with dermatan sulfate, xanthine oxidases modified with heparin, xanthine oxidases modified with hybrid N-glycans, xanthine oxidases modified with complex N-glycans, oxalate oxidases modified with hyaluronic acid, oxalate oxidases modified with chitin, oxalate oxidases modified with partially deacetylated chitin, oxalate oxidases modified with high-mannose N-glycans, oxalate oxidases modified with keratin, oxalate oxidases modified with keratin sulfate, oxalate oxidases modified with chondroitin, oxalate oxidases modified with chondroitin sulfate, oxalate oxidases modified with dermatan, oxalate oxidases modified with dermatan sulfate, oxalate oxidases modified with heparin, oxalate oxidases modified with hybrid N-glycans, oxalate oxidases modified with complex N-glycans, cholesterol oxidases modified with hyaluronic acid, cholesterol oxidases modified with chitin, cholesterol oxidases modified with partially deacetylated chitin, cholesterol oxidases modified with high-mannose N-glycans, cholesterol oxidases modified with keratin, cholesterol oxidases modified with keratin sulfate, cholesterol oxidases modified with chondroitin, cholesterol oxidases modified with chondroitin sulfate, cholesterol oxidases modified with dermatan, cholesterol oxidases modified with dermatan sulfate, cholesterol oxidases modified with heparin, cholesterol oxidases modified with hybrid N-glycans, cholesterol oxidases modified with complex N-glycans, histamine oxidases modified with hyaluronic acid, histamine oxidases modified with chitin, histamine oxidases modified with partially deacetylated chitin, histamine oxidases modified with high-mannose N-glycans, histamine oxidases modified with keratin, histamine oxidases modified with keratin sulfate, histamine oxidases modified with chondroitin, histamine oxidases modified with chondroitin sulfate, histamine oxidases modified with dermatan, histamine oxidases modified with dermatan sulfate, histamine oxidases modified with heparin, histamine oxidases modified with hybrid N-glycans, histamine oxidases modified with complex N-glycans, glycine oxidases modified with hyaluronic acid, glycine oxidases modified with chitin, glycine oxidases modified with partially deacetylated chitin, glycine oxidases modified with high-mannose N-glycans, glycine oxidases modified with keratin, glycine oxidases modified with keratin sulfate, glycine oxidases modified with chondroitin, glycine oxidases modified with chondroitin sulfate, glycine oxidases modified with dermatan, glycine oxidases modified with dermatan sulfate, glycine oxidases modified with heparin, glycine oxidases modified with hybrid N-glycans, glycine oxidases modified with complex N-glycans, NADH oxidases modified with hyaluronic acid, NADH oxidases modified with chitin, NADH oxidases modified with partially deacetylated chitin, NADH oxidases modified with high-mannose N-glycans, NADH oxidases modified with keratin, NADH oxidases modified with keratin sulfate, NADH oxidases modified with chondroitin, NADH oxidases modified with chondroitin sulfate, NADH oxidases modified with dermatan, NADH oxidases modified with dermatan sulfate, NADH oxidases modified with heparin, NADH oxidases modified with hybrid N-glycans, NADH oxidases modified with complex N-glycans, galactose oxidases modified with hyaluronic acid, galactose oxidases modified with chitin, galactose oxidases modified with partially deacetylated chitin, galactose oxidases modified with high-mannose N-glycans, galactose oxidases modified with keratin, galactose oxidases modified with keratin sulfate, galactose oxidases modified with chondroitin, galactose oxidases modified with chondroitin sulfate, galactose oxidases modified with dermatan, galactose oxidases modified with dermatan sulfate, galactose oxidases modified with heparin, galactose oxidases modified with hybrid N-glycans, galactose oxidases modified with complex N-glycans, alcohol dehydrogenases modified with hyaluronic acid, alcohol dehydrogenases modified with chitin, alcohol dehydrogenases modified with partially deacetylated chitin, alcohol dehydrogenases modified with high-mannose N-glycans, alcohol dehydrogenases modified with keratin, alcohol dehydrogenases modified with keratin sulfate, alcohol dehydrogenases modified with chondroitin, alcohol dehydrogenases modified with chondroitin sulfate, alcohol dehydrogenases modified with dermatan, alcohol dehydrogenases modified with dermatan sulfate, alcohol dehydrogenases modified with heparin, alcohol dehydrogenases modified with hybrid N-glycans, alcohol dehydrogenases modified with complex N-glycans, glucose dehydrogenases modified with hyaluronic acid, glucose dehydrogenases modified with chitin, glucose dehydrogenases modified with partially deacetylated chitin, glucose dehydrogenases modified with high-mannose N-glycans, glucose dehydrogenases modified with keratin, glucose dehydrogenases modified with keratin sulfate, glucose dehydrogenases modified with chondroitin, glucose dehydrogenases modified with chondroitin sulfate, glucose dehydrogenases modified with dermatan, glucose dehydrogenases modified with dermatan sulfate, glucose dehydrogenases modified with heparin, glucose dehydrogenases modified with hybrid N-glycans, glucose dehydrogenases modified with complex N-glycans, L-lactate dehydrogenases modified with hyaluronic acid, L-lactate dehydrogenases modified with chitin, L-lactate dehydrogenases modified with partially deacetylated chitin, L-lactate dehydrogenases modified with high-mannose N-glycans, L-lactate dehydrogenases modified with keratin, L-lactate dehydrogenases modified with keratin sulfate, L-lactate dehydrogenases modified with chondroitin, L-lactate dehydrogenases modified with chondroitin sulfate, L-lactate dehydrogenases modified with dermatan, L-lactate dehydrogenases modified with dermatan sulfate, L-lactate dehydrogenases modified with heparin, L-lactate dehydrogenases modified with hybrid N-glycans, L-lactate dehydrogenases modified with complex N-glycans, cortisol dehydrogenases modified with hyaluronic acid, cortisol dehydrogenases modified with chitin, cortisol dehydrogenases modified with partially deacetylated chitin, cortisol dehydrogenases modified with high-mannose N-glycans, cortisol dehydrogenases modified with keratin, cortisol dehydrogenases modified with keratin sulfate, cortisol dehydrogenases modified with chondroitin, cortisol dehydrogenases modified with chondroitin sulfate, cortisol dehydrogenases modified with dermatan, cortisol dehydrogenases modified with dermatan sulfate, cortisol dehydrogenases modified with heparin, cortisol dehydrogenases modified with hybrid N-glycans, cortisol dehydrogenases modified with complex N-glycans, galactose dehydrogenases modified with hyaluronic acid, galactose dehydrogenases modified with chitin, galactose dehydrogenases modified with partially deacetylated chitin, galactose dehydrogenases modified with high-mannose N-glycans, galactose dehydrogenases modified with keratin, galactose dehydrogenases modified with keratin sulfate, galactose dehydrogenases modified with chondroitin, galactose dehydrogenases modified with chondroitin sulfate, galactose dehydrogenases modified with dermatan, galactose dehydrogenases modified with dermatan sulfate, galactose dehydrogenases modified with heparin, galactose dehydrogenases modified with hybrid N-glycans, galactose dehydrogenases modified with complex N-glycans, glycerol dehydrogenases modified with hyaluronic acid, glycerol dehydrogenases modified with chitin, glycerol dehydrogenases modified with partially deacetylated chitin, glycerol dehydrogenases modified with high-mannose N-glycans, glycerol dehydrogenases modified with keratin, glycerol dehydrogenases modified with keratin sulfate, glycerol dehydrogenases modified with chondroitin, glycerol dehydrogenases modified with chondroitin sulfate, glycerol dehydrogenases modified with dermatan, glycerol dehydrogenases modified with dermatan sulfate, glycerol dehydrogenases modified with heparin, glycerol dehydrogenases modified with hybrid N-glycans, glycerol dehydrogenases modified with complex N-glycans, glucose-6-phosphate dehydrogenases modified with hyaluronic acid, glucose-6-phosphate dehydrogenases modified with chitin, glucose-6-phosphate dehydrogenases modified with partially deacetylated chitin, glucose-6-phosphate dehydrogenases modified with high-mannose N-glycans, glucose-6-phosphate dehydrogenases modified with keratin, glucose-6-phosphate dehydrogenases modified with keratin sulfate, glucose-6-phosphate dehydrogenases modified with chondroitin, glucose-6-phosphate dehydrogenases modified with chondroitin sulfate, glucose-6-phosphate dehydrogenases modified with dermatan, glucose-6-phosphate dehydrogenases modified with dermatan sulfate, glucose-6-phosphate dehydrogenases modified with heparin, glucose-6-phosphate dehydrogenases modified with hybrid N-glycans, glucose-6-phosphate dehydrogenases modified with complex N-glycans, 3-hydroxybutyrate dehydrogenases modified with hyaluronic acid, 3-hydroxybutyrate dehydrogenases modified with chitin, 3-hydroxybutyrate dehydrogenases modified with partially deacetylated chitin, 3-hydroxybutyrate dehydrogenases modified with high-mannose N-glycans, 3-hydroxybutyrate dehydrogenases modified with keratin, 3-hydroxybutyrate dehydrogenases modified with keratin sulfate, 3-hydroxybutyrate dehydrogenases modified with chondroitin, 3-hydroxybutyrate dehydrogenases modified with chondroitin sulfate, 3-hydroxybutyrate dehydrogenases modified with dermatan, 3-hydroxybutyrate dehydrogenases modified with dermatan sulfate, 3-hydroxybutyrate dehydrogenases modified with heparin, 3-hydroxybutyrate dehydrogenases modified with hybrid N-glycans, 3-hydroxybutyrate dehydrogenases modified with complex N-glycans, L-malate dehydrogenases modified with hyaluronic acid, L-malate dehydrogenases modified with chitin, L-malate dehydrogenases modified with partially deacetylated chitin, L-malate dehydrogenases modified with high-mannose N-glycans, L-malate dehydrogenases modified with keratin, L-malate dehydrogenases modified with keratin sulfate, L-malate dehydrogenases modified with chondroitin, L-malate dehydrogenases modified with chondroitin sulfate, L-malate dehydrogenases modified with dermatan, L-malate dehydrogenases modified with dermatan sulfate, L-malate dehydrogenases modified with heparin, L-malate dehydrogenases modified with hybrid N-glycans, L-malate dehydrogenases modified with complex N-glycans, sorbitol dehydrogenases modified with hyaluronic acid, sorbitol dehydrogenases modified with chitin, sorbitol dehydrogenases modified with partially deacetylated chitin, sorbitol dehydrogenases modified with high-mannose N-glycans, sorbitol dehydrogenases modified with keratin, sorbitol dehydrogenases modified with keratin sulfate, sorbitol dehydrogenases modified with chondroitin, sorbitol dehydrogenases modified with chondroitin sulfate, sorbitol dehydrogenases modified with dermatan, sorbitol dehydrogenases modified with dermatan sulfate, sorbitol dehydrogenases modified with heparin, sorbitol dehydrogenases modified with hybrid N-glycans, and sorbitol dehydrogenases modified with complex N-glycans, and fusion proteins thereof.

In a more preferred embodiment, the glycosylated protein is selected from the group consisting of glucose oxidases modified with hyaluronic acid, glucose oxidases modified with partially deacetylated chitin, glucose oxidases modified with complex N-glycans, lactate oxidases modified with hyaluronic acid, lactate oxidases modified with partially deacetylated chitin, lactate oxidases modified with complex N-glycans, alcohol oxidases modified with hyaluronic acid, alcohol oxidases modified with partially deacetylated chitin, alcohol oxidases modified with complex N-glycans, glutamate oxidases modified with hyaluronic acid, glutamate oxidases modified with partially deacetylated chitin, glutamate oxidases modified with complex N-glycans, choline oxidases modified with hyaluronic acid, choline oxidases modified with partially deacetylated chitin, choline oxidases modified with complex N-glycans, sarcosine oxidases modified with hyaluronic acid, sarcosine oxidases modified with partially deacetylated chitin, sarcosine oxidases modified with complex N-glycans, xanthine oxidases modified with hyaluronic acid, xanthine oxidases modified with partially deacetylated chitin, xanthine oxidases modified with complex N-glycans, cholesterol oxidases modified with hyaluronic acid, cholesterol oxidases modified with partially deacetylated chitin, cholesterol oxidases modified with complex N-glycans, histamine oxidases modified with hyaluronic acid, histamine oxidases modified with partially deacetylated chitin, histamine oxidases modified with complex N-glycans, NADH oxidases modified with hyaluronic acid, NADH oxidases modified with partially deacetylated chitin, NADH oxidases modified with complex N-glycans, alcohol dehydrogenases modified with hyaluronic acid, alcohol dehydrogenases modified with partially deacetylated chitin, alcohol dehydrogenases modified with complex N-glycans, glucose dehydrogenases modified with hyaluronic acid, glucose dehydrogenases modified with partially deacetylated chitin, glucose dehydrogenases modified with complex N-glycans, L-lactate dehydrogenases modified with hyaluronic acid, L-lactate dehydrogenases modified with partially deacetylated chitin, L-lactate dehydrogenases modified with complex N-glycans, cortisol dehydrogenases modified with hyaluronic acid, cortisol dehydrogenases modified with partially deacetylated chitin, cortisol dehydrogenases modified with complex N-glycans, L-malate dehydrogenases modified with hyaluronic acid, L-malate dehydrogenases modified with partially deacetylated chitin, and L-malate dehydrogenases modified with complex N-glycans, and fusion proteins thereof.

In another aspect of the present invention, the glycosylated protein, fabricated by the methods disclosed herein, is used in the assembly of an amperometric biosensor. The amperometric biosensor comprises a counter electrode, a reference electrode, one or more optional rejection layers, and a working electrode that comprises a sensing element, which comprises a support having a surface; and a layer on the surface, wherein the layer comprises an amino sidechain glycosylated enzyme, wherein the enzyme is predominantly in its active form. The counter and reference electrodes may be separate to form a three-electrode amperometric biosensor, or combined to form a two-electrode amperometric biosensor. The layer on the surface containing the amino sidechain glycosylated enzyme may optionally contain other proteins and crosslinking agents.

FIG. 21 is a schematic drawing of a prototypical working electrode in an amperometric biosensor. 101 and 103 are optional rejection layers, which may have the same or different compositions. 102 is the layer where the amino sidechain glycosylated enzyme and other optional proteins and crosslinking agents reside. 104 is the working electrode sensing element and supports 102 and 103. 104 is typically held at a bias of 0.4 to 0.9 V versus a Ag/AgCl reference electrode. 105 is the current generated at 104 by virtue of the peroxide generated by the enzyme in 102. One of ordinary skill in the art will recognize that the sensing element 106 would be the same regardless of whether the biosensor employs a two electrode configuration (wherein the reference and counter electrode are combined), or a three electrode configuration (wherein the reference and counter electrodes are separate entities).

In a preferred embodiment, the glycosylated protein is an enzyme independently selected from the group consisting of glucose oxidases, lactate oxidases, alcohol oxidases, glutamate oxidases, xanthine oxidases, sarcosine oxidases, cholesterol oxidases, oxalate oxidases, D-amino acid oxidases, choline oxidases, glutathione sulfhydryl oxidases, (S)-6-hydroxynicotine oxidases, (R)-6-hydroxynicotine oxidases, pyruvate oxidases, acyl coenzyme A oxidases, glycerolphosphate oxidases, GABA oxidases, histamine oxidases, diamine oxidases, nucleoside oxidases, L-lysine oxidases, L-aspartate oxidases, glycine oxidases, galactose oxidases, NADH oxidases, glucose dehydrogenases, alcohol dehydrogenases, cortisol dehydrogenases, lactate dehydrogenases, and fusion proteins thereof.

In another preferred embodiment, the glycosylated protein is glycosylated with a carbohydrate that is selected from the group consisting of chitin, partially deacylated chitin, hyaluronic acid, keratin, keratin sulfate, chondroitin, chondroitin sulfate, dermatan, dermatan sulfate, heparin, native N-glycan cores, high-mannose N-glycans, hybrid N-glycans, complex N-glycans, and derivatives thereof.

In another embodiment of the present invention, the glycosylated proteins may find use in human health monitoring applications. In another embodiment of the present invention, the glycosylated proteins may find use in non-human mammal health monitoring applications.

The following examples set forth preferred methods in accordance with the invention. It is understood, however, that these examples are provided by way of illustration and nothing therein should be taken as a limitation upon the overall scope of the invention.

Protein expression and purification: Proteins glucose oxidase (GOx), MBP-glucose oxidase (MBP-GOx), lactate oxidase (LOx), MBP-lactate oxidase (MBP-LOx), MBP-putrescine oxidase (MBP-PutOx), glycine oxdase (GlyOx), sarcosine oxidase (SOx), glutamate oxidase (GlutOx), alcohol oxidase (AOx), NctB oxidase (NicOx), cholesterol oxidase from brevibacterium (COx2), MBP-cholesterol oxidase from sp. Penicillium (MBP-COx1), alcohol dehydrogenase (ADH), cortisol dehydrogenase (CDH), glucose dehydrogenase (GDH), L-lactate dehydrogenase (LDH), malate dehydrogenase (MDH)] were either purchased from commercial vendors or prepared by standard recombinant over-expression techniques using published methods' in E. Coli.[37] or Pichia Pastoris[38-39], and purified by standard methods.[40]

Carbohydrates: N-acetylglucosamine (GlcNAc), N-acetylmannosamine (ManNAc), N-acetylgalactosamine (GalNAc), diacetylchitobiose (DACB), triacetylchitotriose (TACT), Lewis B tetrasaccharide (LewB4), native N-gylcan cores Man-3 and Man-5, and hyaluronic acid polymers of various lengths including those of less than 6K Mw (HA6), and those of less than 50K Mw (HA50) were obtained from commercial sources. N-propanylglucosamine, N-n-butanylglucosamine, N-isopropanylglucosamine, N-2,2,dimethylpropanylglucosamine, N-((2-oxoethoxy)-propanyl)glucosamine were synthesized using the method of Inouye et al.[41]

General oxazoline formation protocol: A carbohydrate with an N-acyl-2-amino moiety at the reducing end was dissolved in deionized $H_2O$. At least 7.5 molar equivalents of triethylamine or $Na_3PO_4$ were added until the pH was 11. Three molar equivalents of either DMC or CDMBI were added and the reaction incubated at 4° C. from 2 to 24 hours. The pH of the solution was then adjusted to pH 8-8.5 with 1 M bicine or to pH 6, 7, or 8 with 1M MES. After adjustment of pH, some oxazolines were flash frozen in liquid nitrogen and stored at −80° C. until use. CDMBI (2-chloro-1,3-dimethyl-1H-benzimidazol-3-ium chloride) was prepared according to the method of Noguchi et al.[21] DMC (chloro-1,3-dimethylimidazolinium chloride) was purchased from commercial sources.

General preparation of protein: Protein was prepared for conjugation by either dissolving lyophilized protein in PBS, pH 8.0 followed by desalting via a G-50 spin column equilibrated with PBS pH 8.0, or dissolved in PBS, pH 8.0, and used directly. The protein concentration was determined by triplicate Bradford assay.[42] Of the solution, the volume of solution containing from about 5 ug to 50 mg was aliquoted into a microfuge tube for use in the conjugation reaction.

General conjugation of neutralized oxazoline carbohydrate with a protein: The neutralized oxazolines and target proteins were prepared as above. The protein solution was dispensed into a microfuge tube followed by addition of about a 100 to 1000-fold molar excess of the carbohydrate oxazoline and allowed to react from 2 hours to 72 hours at 4° C. or room temperature. Up to 5 ug samples were withdrawn for SDS-PAGE gel mobility shift assay to determine reaction completeness. Novex 8% and/or 12% bis-tris SDS-PAGE gels were used with a MES-SDS running buffer. The remainder of the samples were then cryopreserved by addition of glycerol to 20% v/v, flash frozen in liquid nitrogen, and stored at −80° C.

SDS-PAGE gels were stained with PageBlue (Thermo Scientific) and destained in deionized water optionally supplemented with 1% acetic acid.[37] Destained gels were visualized on an optical trans-illuminator, and the relative gel mobility evaluated based on the lagging edge of each band. Conjugated constructs derived from highly charged carbohydrate oxazolines (i.e. hyaluronic acid, the glycosaminoglycans, partially deacetylated chitin)[27-29] may produce distortion in the band morphology, wherein the band morphology being manifest as distortion, streaking, smearing, lengthening, lightening of the stained band, formation of a chevron-shaped and/or U-shaped band, and/or extension of the band wherein the distal portions of the band display retarded mobility relative to the center of the band in the lane, and wherein the change in morphology is relative to the unconjugated protein sample band.[37, 43-45]

Enzymatic activity assay: Samples were thawed for assay and desalted into PBS (140 mM NaCl, 10 mM NaPO$_4$ pH 7.4) via Sephadex G-50 spin column. The concentration of each desalted protein sample was determined by triplicate Bradford assay using previously described methods.[42] Oxidase enzymes were assayed in triplicate by Amplex red peroxidase coupled assay @ RT under saturating substrate conditions using previously described methods.[46-47] Dehydrogenase enzymes were assayed in triplicate by direct spectrophotometric detection of the NADH product at room temperature under saturating substrate concentrations, using previously described methods.[48] Enzyme concentrations giving optical rates between 0.01 ΔA*min-1 and 0.2 ΔA*min-1 were employed for all enzymes. Mass specific activity (pmoles product*min-1*mg-1, U/mg) of each control sample and their conjugates were calculated using the experimentally determined slope of either the hydrogen peroxide standard curve (0.0308 A560*cm-1*μM-1) or the μM extinction coefficient of NADH (0.006220 A340*cm-1*μM-1), the optical rate of each assay (ΔA560*min-1), and the mass of enzyme of enzyme in mg in the assay. Data was plotted in Prism software (GraphPad).

Water bath activity study of glycan-protein conjugates: After assay, protein samples were incubated in a water bath @42° C. for 24-96 hours, incubated on ice for 2 minutes, then centrifuged for 10 s@10,000 rpm. Determination of the mass specific activity of these samples was then performed as described in previously. Specific activity values before and after thermal incubation were plotted with Prism software(GraphPad).

Fluorescence thermal shift assay (FTSA) of glycan-protein conjugates: The impact of carbohydrate conjugation on the thermal stability was evaluated by a SYPRO-Orange dye association fluorescence thermal shift assay.[49] Melts were performed on each control protein and each of its respective conjugates. After activity assay, protein samples were prepared for fluorescence thermal shift assay by dilution to 0.1-5.0 μM in a 2 mL final volume with PBS supplemented with 2.5× SYPRO-Orange dye (Invitrogen). Fluorescence emission intensity was observed vs temperature in a Cary Eclipse fluorescence spectrophotometer equipped with a multi cell peltier (484 nm ex, 620 nm em, 1 sec integration time, 10 nm em/ex slit width, 1° C./minute temperature ramp rate, 0.5 C data interval, medium detector sensitivity). Data was collected from 20° C. to 85° C. or until the fluorescence intensity began to decline from its maximum. The fluorescence intensity values were normalized relative to the initial and maximum observed values and the apparent Tm determined by fitting the resulting data to a two state Boltzmann sigmoid by nonlinear regression analysis using Prism software(GraphPad).

Figure 1:
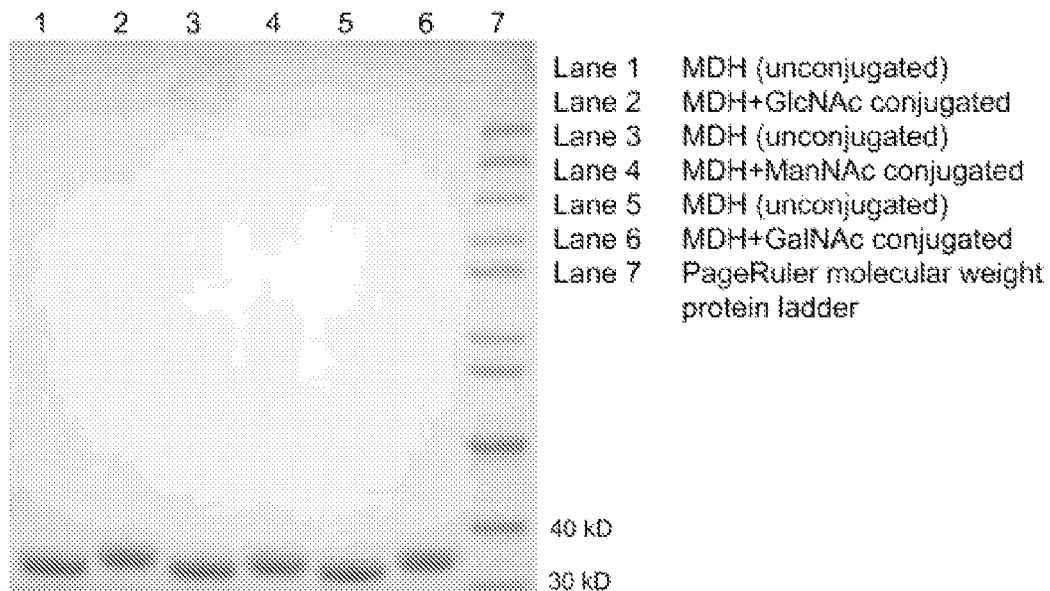
FIG. 1 is a representative SDS-PAGE gel (8% gel, 1 ug of sample per lane) demonstrating the conjugation of malate dehydrogenase (MDH, lanes 1, 3 and 5) with the oxazolines of N-acetylglucosamine (GlcNAc, lane 2), N-acetylmannosamine (ManNAc, lane 4), and N-acetylgalactosamine (GalNAc, lane 6), wherein the protein to carbohydrate ratio in the conjugation reaction was about 1:1000 and the conjugation reaction was allowed to proceed for about 24 hours at room temperature.

The representative SDS-PAGE gel image in FIG. 1 demonstrates, by virtue of the observed band shifts between the native MDH enzyme and the glycosylated MDH enzyme, that coupling a nucleophilic amino sidechain occurs and is independent of the stereochemistry within the oxazoline ring (Examples 1, 2, and 3).

Figure 2:
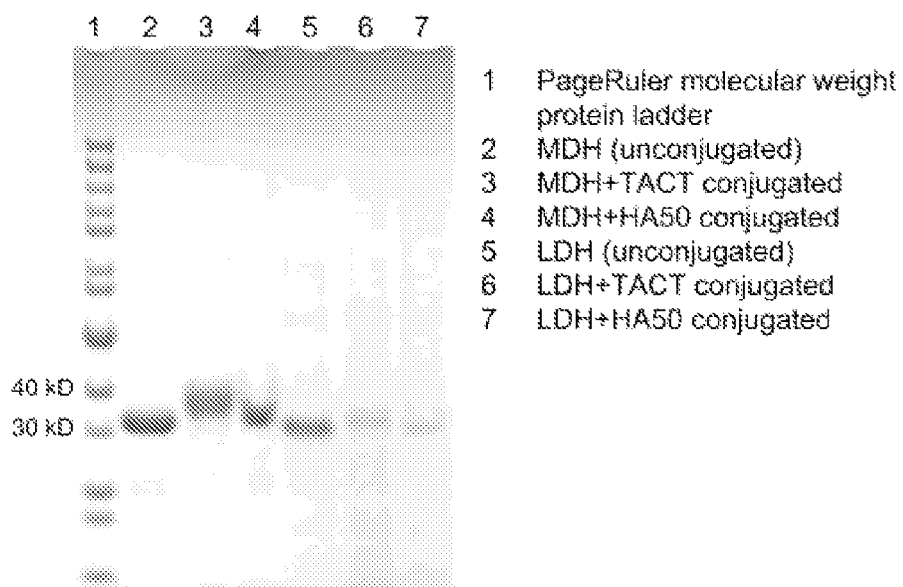
FIG. 2 is a representative SDS-PAGE gel (8% gel, 2 ug of sample per lane) demonstrating the conjugation of malate dehydrogenase (MDH, lane 2) and L-lactate dehydrogenase (LDH, lane 5) with the oxazolines of triacetylchitotriose (TACT, lanes 3 and 6, respectively) and hyaluronic acid of nominal molecular weight of about 50 kD (HA50, lanes 4 and 7, respectively), wherein the protein to carbohydrate ratio in the conjugation reaction was about 1:100 and the conjugation reaction was allowed to proceed for about 24 hours at room temperature.

The representative SDS-PAGE gel image in FIG. 2 demonstrates, by virtue of the observed band shifts between the native MDH and LDH enzymes and the glycosylated forms thereof, that the coupling of both small and large linear oligosaccharides occurs and is independent of the size of the linear oligosaccharide (Examples 4, 7, 26, and 28).

Figure 3:
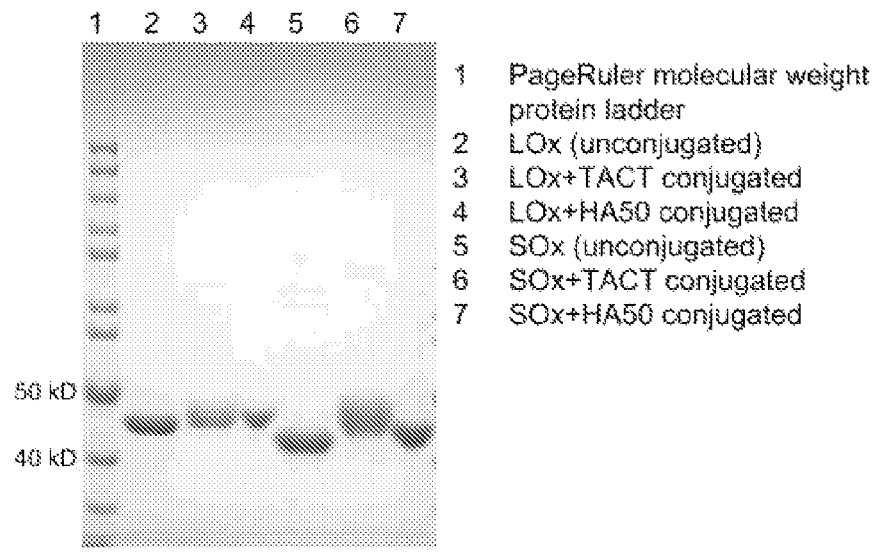
FIG. 3 is a representative SDS-PAGE gel (8% gel, 2 ug of sample per lane) demonstrating the conjugation of L-lactate oxidase (LOx, lane 2) and sarcosine oxidase (SOx, lane 5) with the oxazolines of triacetylchitotriose (TACT, lanes 3 and 6, respectively) and hyaluronic acid of nominal molecular weight of about 50 kD (HA50, lanes 4 and 7, respectively), wherein the protein to carbohydrate ratio in the conjugation reaction was about 1:100 and the conjugation reaction was allowed to proceed for about 24 hours at room temperature.

The representative SDS-PAGE gel image in FIG. 3 demonstrates, by virtue of the observed band shifts between the native LOx and SOx enzymes and the glycosylated forms thereof, that the coupling of both small and large linear oligosaccharides occurs and is independent of the size of the linear oligosaccharide (Examples 58, 60, 72, and 74).

Figure 4:
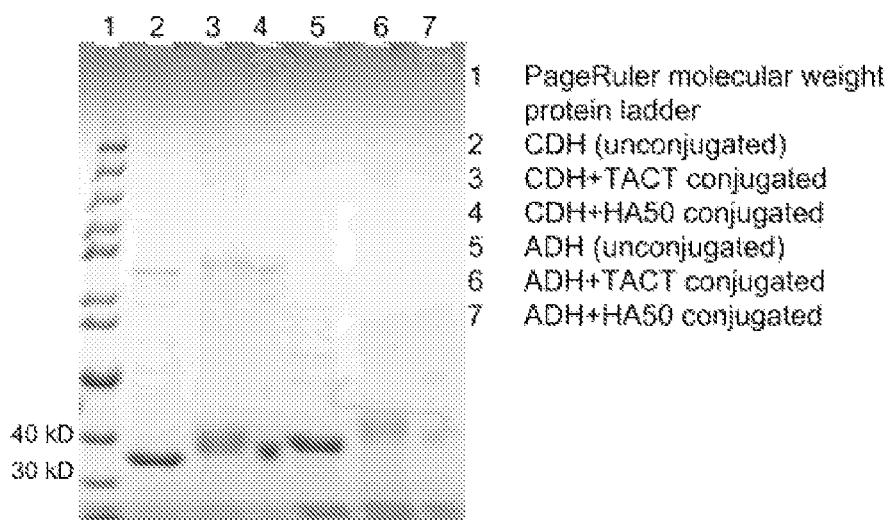
FIG. 4 is a representative SDS-PAGE gel (8% gel, 2 ug of sample per lane) demonstrating the conjugation of cortisol dehydrogenase (CDH, lane 2) and alcohol dehydrogenase (ADH, lane 5) with the oxazolines of triacetylchitotriose (TACT, lanes 3 and 6, respectively) and hyaluronic acid of nominal molecular weight of about 50 kD (HA50, lanes 4 and 7, respectively), wherein the protein to carbohydrate ratio in the conjugation reaction was about 1:100 and the conjugation reaction was allowed to proceed for about 24 hours at room temperature.

The representative SDS-PAGE gel image in FIG. 4 demonstrates, by virtue of the observed band shifts between the native CDH and ADH enzymes and the glycosylated forms thereof, that the coupling of both small and large linear oligosaccharides occurs and is independent of the size of the linear oligosaccharide (Examples 14, 16, 18, and 20).

Figure 5:
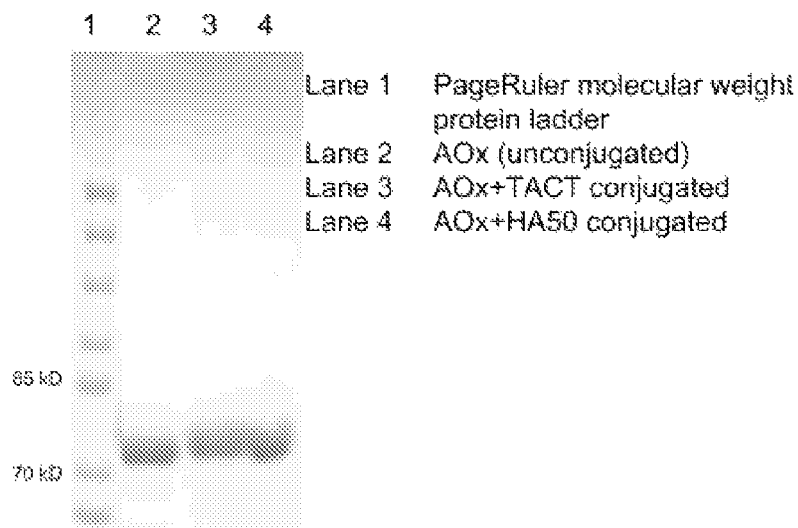
FIG. 5 is a representative SDS-PAGE gel (8% gel, 2 ug of sample per lane) demonstrating the conjugation of alcohol oxidase (AOx, lane 2) with the oxazolines of triacetylchitotriose (TACT, lane 3) and hyaluronic acid of nominal molecular weight of about 50 kD (HA50, lane 4), wherein the protein to carbohydrate ratio in the conjugation reaction was about 1:100 and the conjugation reaction was allowed to proceed for about 24 hours at room temperature.

The representative SDS-PAGE gel image in FIG. 5 demonstrates, by virtue of the observed band shifts between native AOx enzyme and the glycosylated forms thereof, that the coupling of both small and large linear oligosaccharides occurs and is independent of the size of the linear oligosaccharide (Examples 30 and 32).

Figure 6:
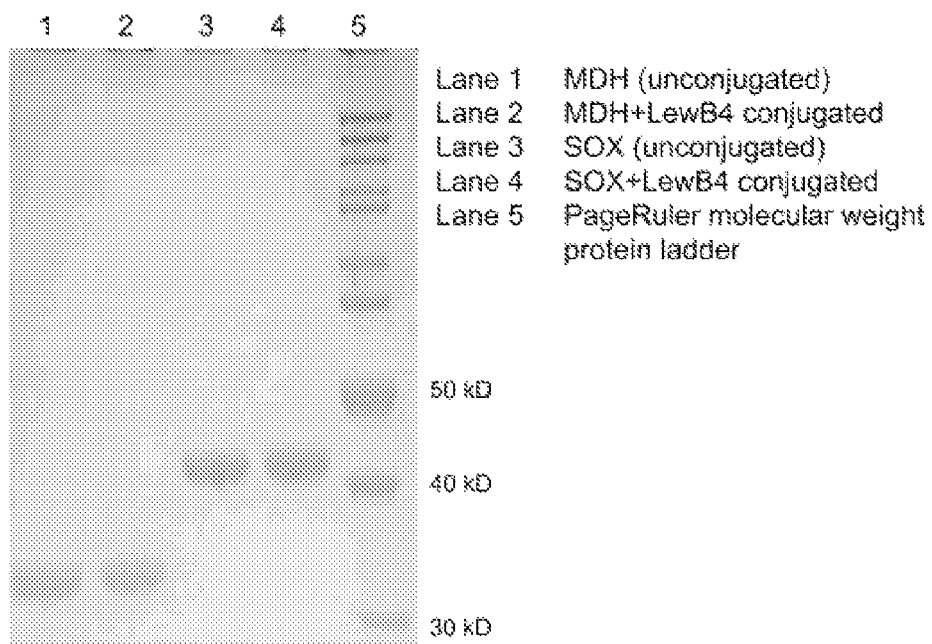
FIG. 6 is a representative SDS-PAGE gel (12% gel, 0.5 ug of sample per lane) demonstrating the conjugation of malate dehydrogenase (MDH, lane 1) and sarcosine oxidase (SOx, lane 3) with the oxazolines of Lewis B tetrasaccharide (LewB4, lanes 2 and 4, respectively), wherein the protein to carbohydrate ratio in the conjugation reaction was about 1:1000 and the conjugation reaction was allowed to proceed for about 72 hours at room temperature.

The representative SDS-PAGE gel image in FIG. 6 demonstrates, by virtue of the observed band shifts between the native MDH and SOx enzymes and those glycosylated with LewB4, that the coupling of a fucosyl complex N-glycan oligosaccharides occurs and is independent of enzyme type (Examples 5 and 61).

Figure 7:
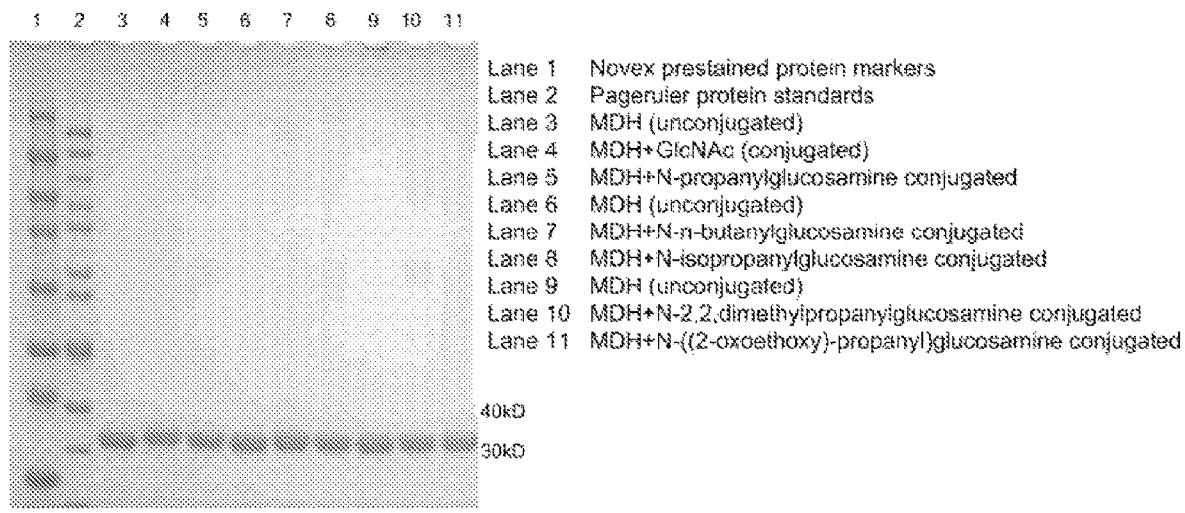
FIG. 7 is a representative SDS-PAGE gel (8% gel, 1 ug of sample per lane) demonstrating the conjugation of malate dehydrogenase (MDH, lanes 3, 6 and 9) with the oxazolines of N-acetylglucosamine (GlcNAc, lane 4), N-propanylglucosamine (lane 5), N-n-butanylglucosamine (lane 7), N-isopropanylglucosamine (lane 8), N-2,2,dimethylpropanylglucosamine (lane 10), N-((2-oxoethoxy)-propanyl)glucosamine (lane 11), wherein the protein to carbohydrate ratio in the conjugation reaction was about 1:1000 and the conjugation reaction was allowed to proceed for about 24 hours at room temperature.

The representative SDS-PAGE gel image in FIG. 7 demonstrates, by virtue of the observed band shifts between the native MDH enzyme and the glycosylated MDH enzyme, that coupling a nucleophilic amino sidechain occurs and is independent of the R moiety on the oxazoline ring (Examples 8, 9, 10, 11, and 12).

Figure 8:
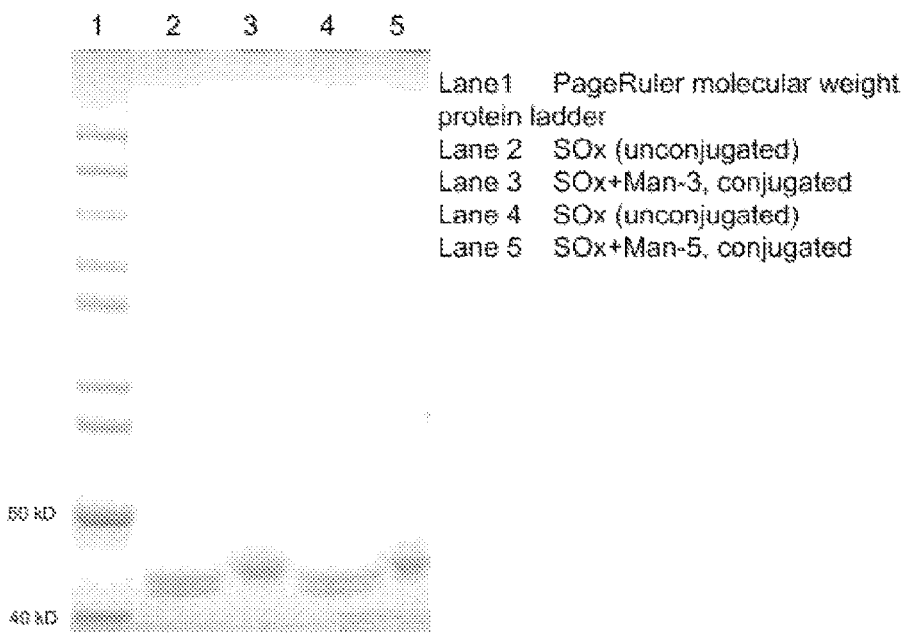
FIG. 8 is a representative SDS-PAGE gel (8% gel, 0.5 ug of sample per lane) demonstrating the conjugation of sarcosine oxidase (SOx, lanes 2 and 4) with the oxazolines of native N-glycan core Man-3 (lane 3) and with high mannose N-glycan core Man-5 (lane 5), respectively, and wherein the protein to carbohydrate ratio in the conjugation reaction was about 1:1000 and the conjugation reaction was allowed to proceed for about 24 hours at room temperature.

The representative SDS-PAGE gel image in FIG. 8 demonstrates, by virtue of the observed band shifts between the native SOx enzyme and that glycosylated with Man-3 and Man-5, that the coupling of N-glycan cores and high-mannose N-glycans oligosaccharides occurs and is independent of glycan type (Examples 62 and 63).

Figure 9:
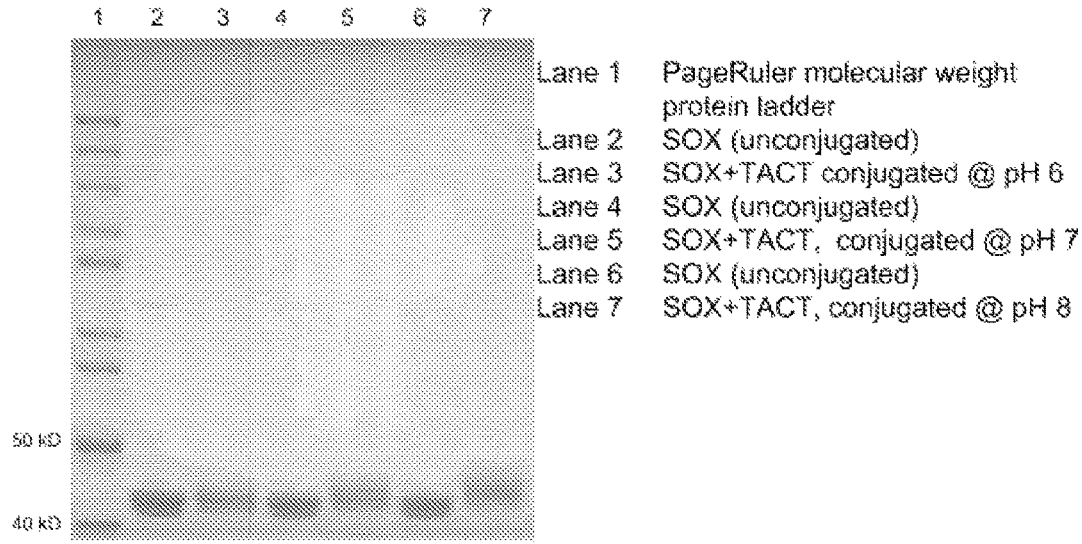
FIG. 9 is a representative SDS-PAGE gel (8% gel, 1 ug of sample per lane) demonstrating the conjugation of sarcosine oxidase (SOx, lanes 2, 4 and 6) with the oxazolines of triacetylchitotriose (TACT, lanes 3, 5, and 7) at pH 6, 7 and 8, respectively, wherein the protein to carbohydrate ratio in the conjugation reaction was about 1:1000 and the conjugation reaction was allowed to proceed for about 24 hours at room temperature.

The representative SDS-PAGE gel image in FIG. 9 demonstrates, by virtue of the observed band shifts between the native SOx enzymes and the TACT glycosylated form, that the coupling occurs over a range of pH values, including those that are slightly acidic (Examples 58, 77, and 78).

Figure 10:
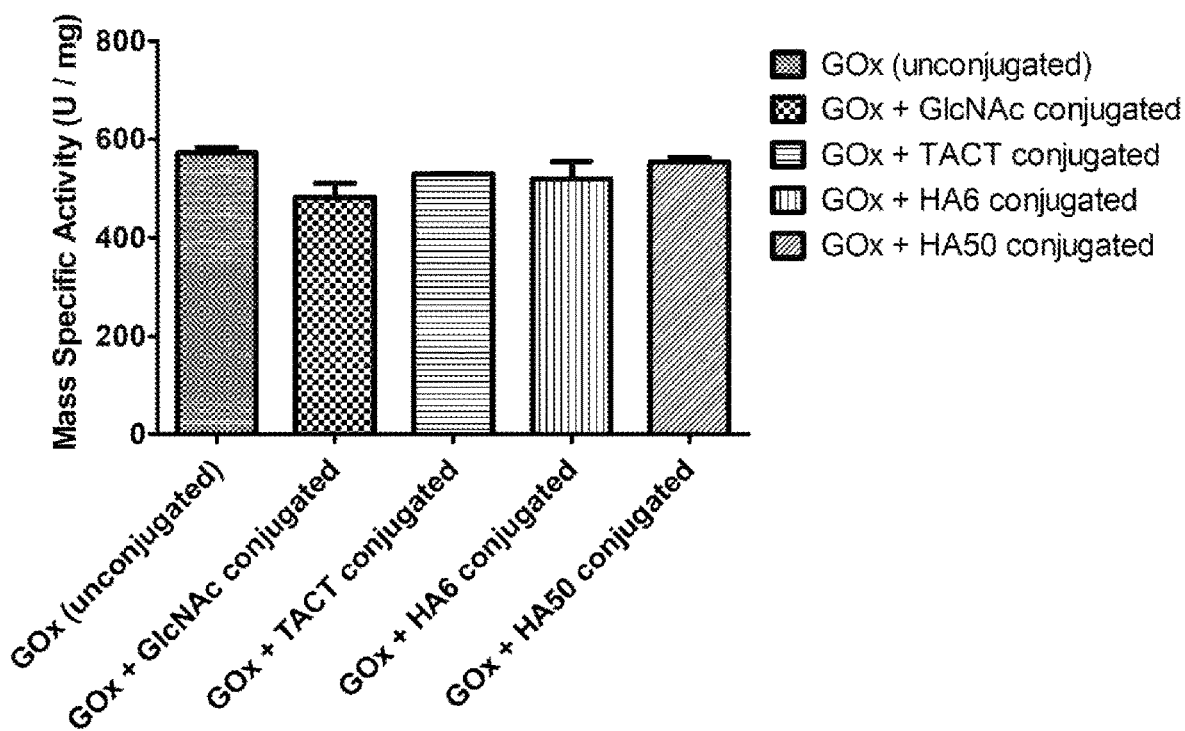
FIG. 10 is a representative triplicate mass specific activity determination of wild-type native glucose oxidase (GOx, column 1), GOx conjugated with GlcNAc (column 2), GOx conjugated with TACT (column 3), GOx conjugated with HA6 (column 4), and GOx conjugated with HA50 (column 5)

The representative triplicate mass specific activity determinations in FIG. 10 demonstrate, by virtue of the observed activity, that the native GOx enzyme substantially retains activity after glycosylation with a range of different carbohydrates (monosaccharide, trisaccharide, and linear oligosaccharides), thereby demonstrating that glycosylation does not substantially alter either structure or function (Examples 64, 65, 66, and 67). These data further demonstrate that GOx can be hyper-glycosylated, as the native enzyme naturally possesses one or more N-glycan units in the traditional sense.

Figure 11:
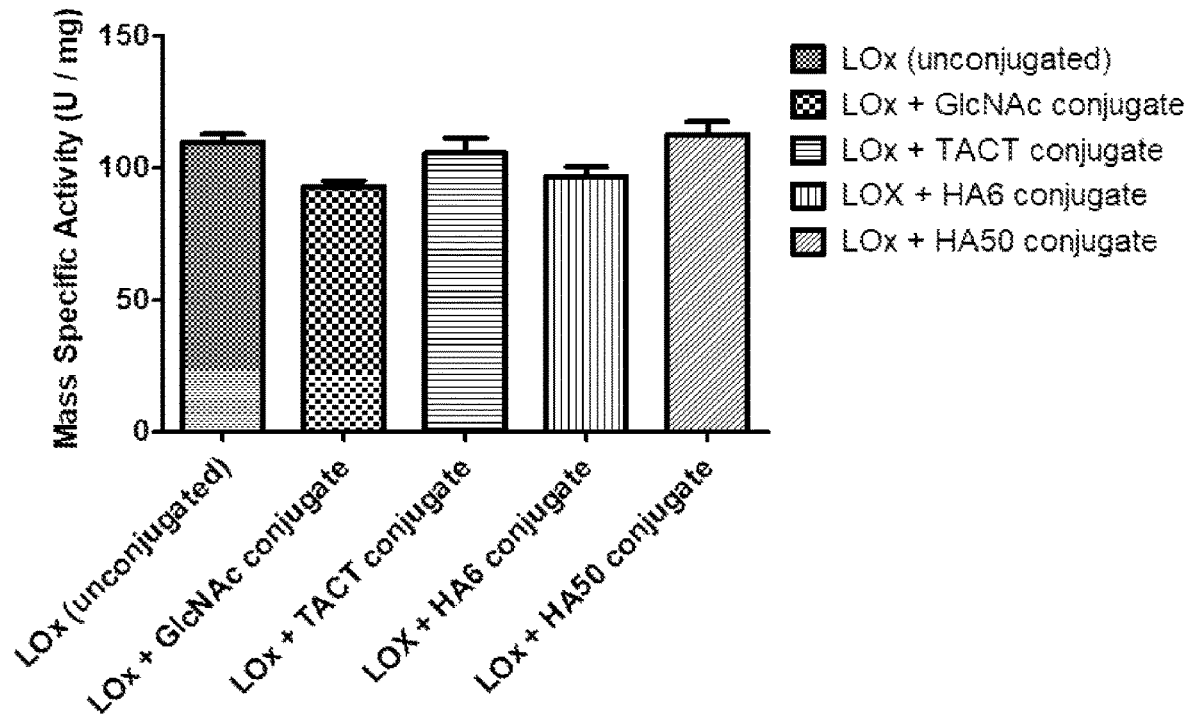
FIG. 11 is a representative triplicate mass specific activity determination of wild-type native L-lactate oxidase (LOx, column 1), LOx conjugated with GlcNAc (column 2), LOx conjugated with TACT (column 3), LOx conjugated with HA6 (column 4), and LOx conjugated with HA50 (column 5)

The representative triplicate mass specific activity determinations in FIG. 11 demonstrate, by virtue of the observed activity, that the native LOx enzyme substantially retains activity after glycosylation with a range of different carbohydrates (monosaccharide, trisaccharide, and linear oligosaccharides), thereby demonstrating that glycosylation does not substantially alter either structure or function (Examples 70, 72, 73, and 74).

Figure 12:
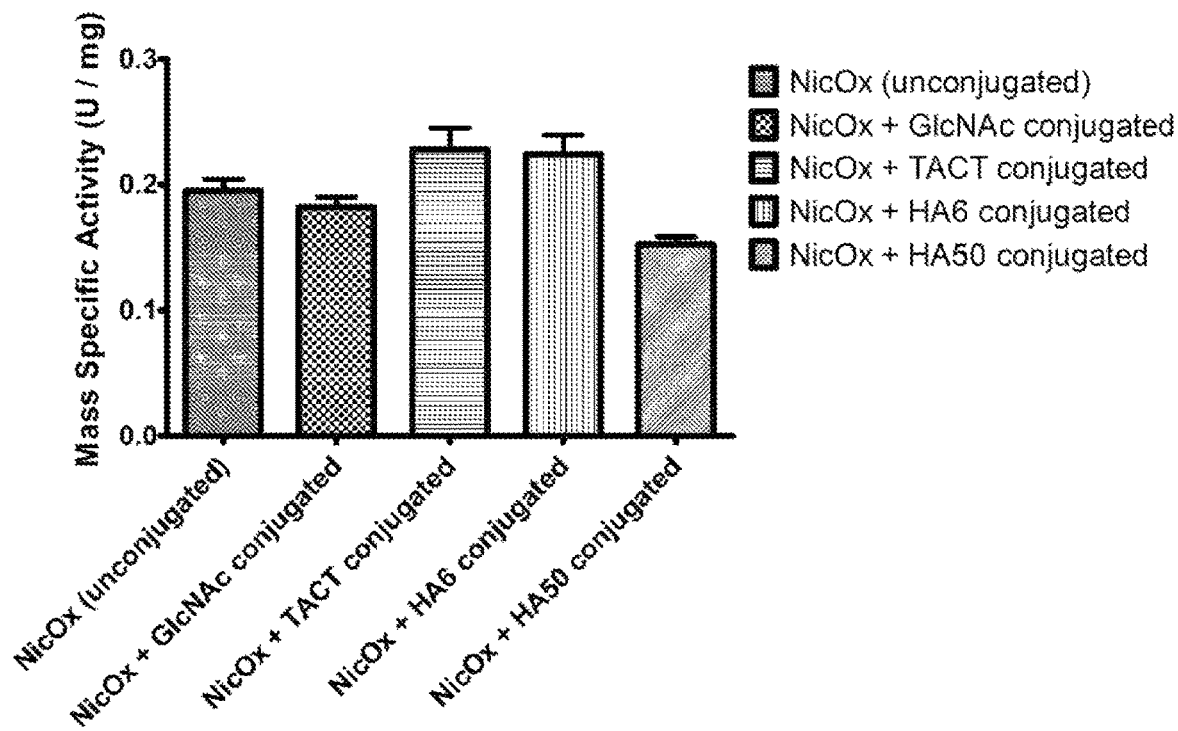
FIG. 12 is a representative triplicate mass specific activity determination of wild-type native NctB oxidase (NicOx, column 1), NicOx conjugated with GlcNAc (column 2), NicOx conjugated with TACT (column 3), NicOx conjugated with HA6 (column 4), and NicOx conjugated with HA50 (column 5)

The representative triplicate mass specific activity determinations in FIG. 12 demonstrate, by virtue of the observed activity, that the native NicOx enzyme substantially retains activity after glycosylation with a range of different carbohydrates (monosaccharide, trisaccharide, and linear oligosaccharides), thereby demonstrating that glycosylation does not substantially alter either structure or function (Examples 49, 50, 51, and 52).

Figure 13:
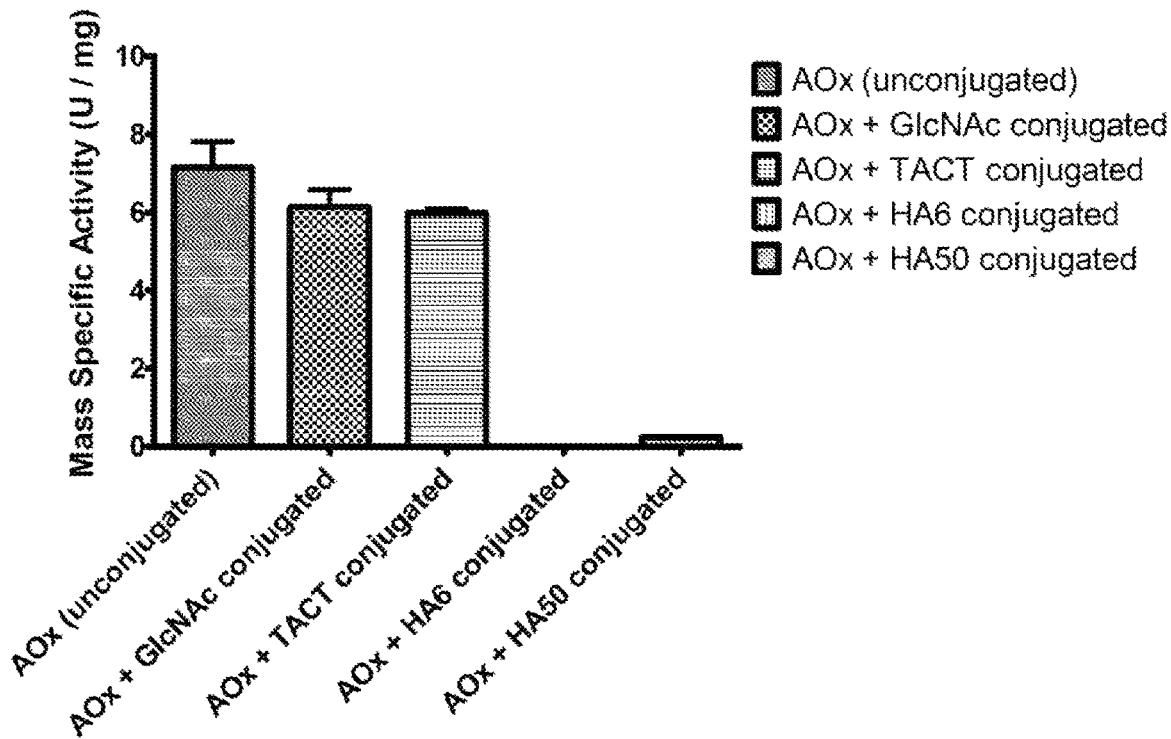
FIG. 13 is a representative triplicate mass specific activity determination of wild-type native alcohol oxidase (AOx, column 1), AOx conjugated with GlcNAc (column 2), AOx conjugated with TACT (column 3), AOx conjugated with HA6 (column 4), and AOx conjugated with HA50 (column 5)

The representative triplicate mass specific activity determinations in FIG. 13 demonstrate, by virtue of the observed activity, that the native AOx enzyme substantially retains activity after glycosylation with a range of different carbohydrates (monosaccharide and trisaccharide), thereby demonstrating that in many cases glycosylation does not substantially alter either structure or function (Examples 29, 30, 31, and 32).

Figure 14:
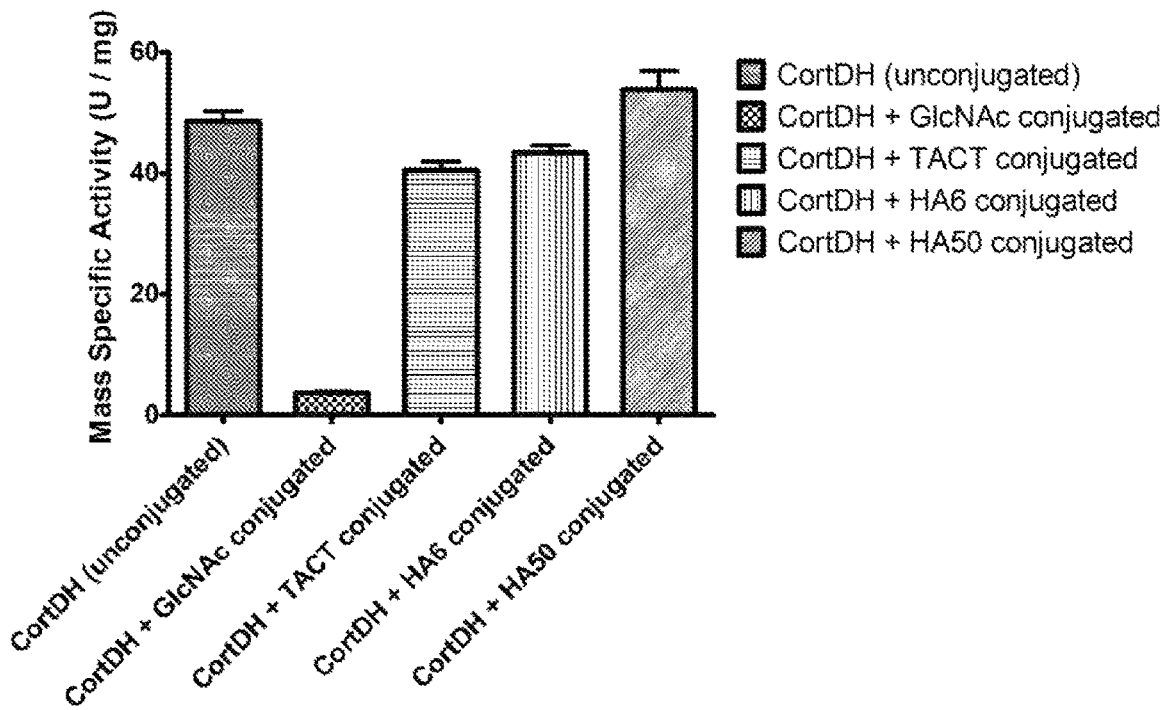
FIG. 14 is a representative triplicate mass specific activity determination of wild-type native cortisol dehydrogenase (CortDH, column 1), CortDH conjugated with GlcNAc (column 2), CortDH conjugated with TACT (column 3), CortDH conjugated with HA6 (column 4), and CortDH conjugated with HA50 (column 5)

The representative triplicate mass specific activity determinations in FIG. 14 demonstrate, by virtue of the observed activity, that the native CortDH enzyme substantially retains activity after glycosylation with a range of different carbohydrates (monosaccharide, trisaccharide, and linear oligosaccharides), thereby demonstrating that glycosylation does not substantially alter either structure or function (Examples 79, 80, 81, and 82).

Figure 15:
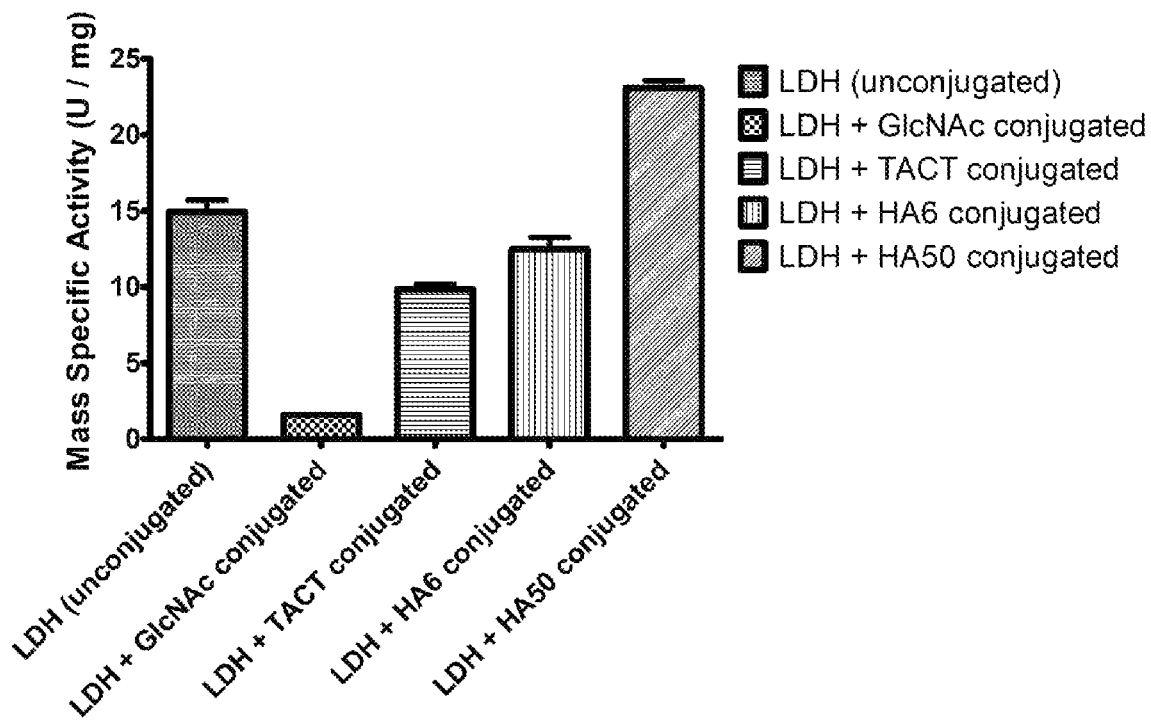
FIG. 15 is a representative triplicate mass specific activity determination of wild-type native L-lactate dehydrogenase (LDH, column 1), LDH conjugated with GlcNAc (column 2), LDH conjugated with TACT (column 3), LDH conjugated with HA6 (column 4), and LDH conjugated with HA50 (column 5)

The representative triplicate mass specific activity determinations in FIG. 15 demonstrate, by virtue of the observed activity, that the native LDH enzyme substantially retains activity after glycosylation with a range of different carbohydrates (monosaccharide, trisaccharide, and linear oligosaccharides), thereby demonstrating that glycosylation does not substantially alter either structure or function (Examples 25, 26, 27, and 28).

Figure 16:
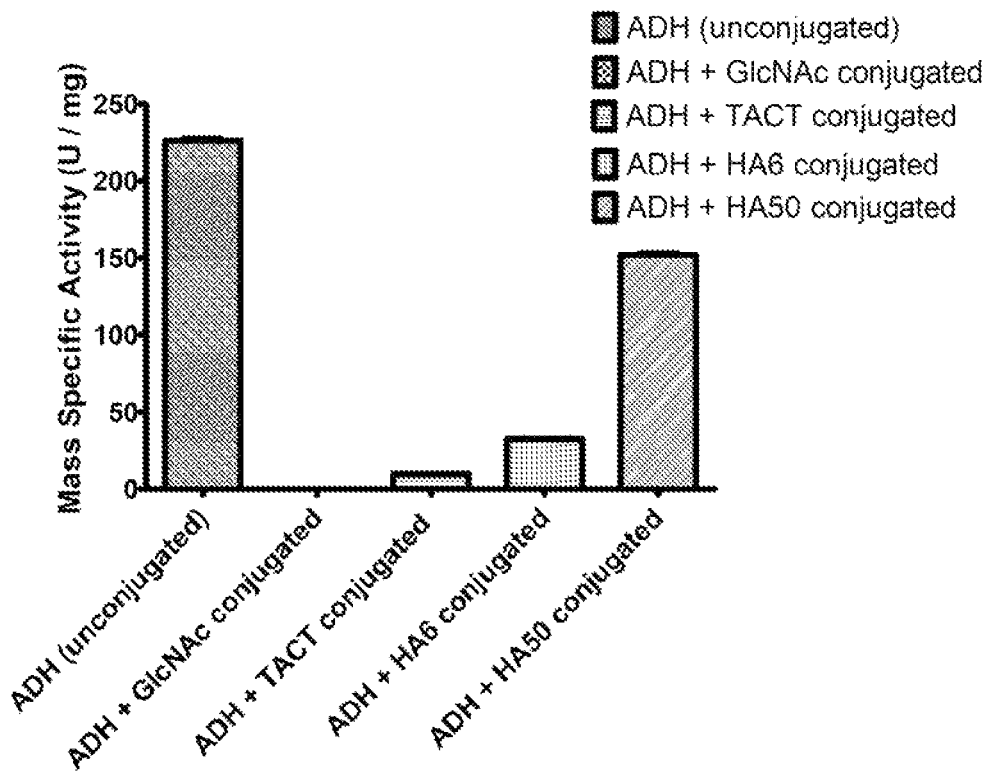
FIG. 16 is a representative triplicate mass specific activity determination of wild-type native alcohol dehydrogenase (ADH, column 1), ADH conjugated with GlcNAc (column 2), ADH conjugated with TACT (column 3), ADH conjugated with HA6 (column 4), and ADH conjugated with HA50 (column 5)

The representative triplicate mass specific activity determinations in FIG. 16 demonstrate, by virtue of the observed activity, that the native ADH enzyme substantially retains activity after glycosylation with a range of different carbohydrates (trisaccharide, and linear oligosaccharides), thereby demonstrating that glycosylation in most cases does not substantially alter either structure or function (Examples 13, 14, 15, and 16).

Figure 17:
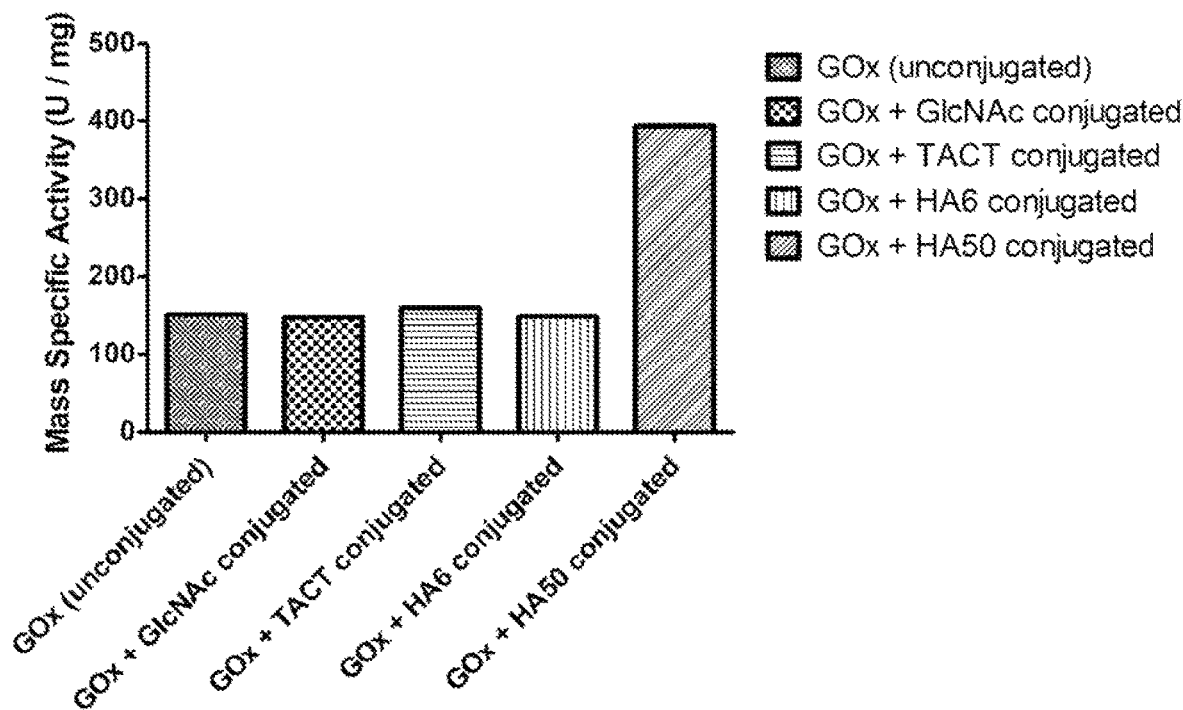
FIG. 17 is a representative mass specific activity determination of wild-type native glucose oxidase (GOx, column 1), GOx conjugated with GlcNAc (column 2), GOx conjugated with TACT (column 3), GOx conjugated with HA6

The representative triplicate mass specific activity determinations in FIG. 17 demonstrate, by virtue of the observed activity, that native GOx, when glycosylated using the current invention, substantially retains activity when heated to 42° C. for 96 hours (Examples 64, 65, 66, and 67). These data further demonstrate that GOx can be hyper-glycosylated, as the native enzyme naturally possesses one or more N-glycan units in the traditional sense, and that the different glycans used for hyper-glycosylation may substantially improve the stability of the native GOx enzyme.

The representative FTSA comparisons in FIG. 18 demonstrate, by virtue of the observed shift in fluorescence activity, that native GOx, when glycosylated using the current invention, shows an improvement in thermal stability (Examples 64, 65, and 66).

The representative FTSA comparisons in FIG. 19 demonstrate, by virtue of the observed shift in fluorescence activity, that native LOx, when glycosylated using the current invention, shows an improvement in thermal stability (Examples 70, 72, 73, and 74).

Example 1: In a manner similar to that described above, GlcNAc was converted to the corresponding carbohydrate oxazoline with CDMBI, which was subsequently reacted with MDH for about 16 hours at room temperature. SDS-PAGE electrophoresis of the resulting modified protein showed a discernible shift indicating that glycosylation of the native protein by the GlcNAc oxazoline occurred.

Example 2: In a manner similar to that described above. ManNAc was converted to the corresponding carbohydrate oxazoline with CDMBI, which was subsequently reacted with MDH for about 16 hours at room temperature. SDS-PAGE electrophoresis of the resulting modified protein showed a discernible shift indicating that glycosylation of the native protein by the ManNAc oxazoline occurred.

Example 3: In a manner similar to that described above. GalNAc was converted to the corresponding carbohydrate oxazoline with CDMBI, which was subsequently reacted with MDH for about 16 hours at room temperature. SDS-PAGE electrophoresis of the resulting modified protein showed a discernible shift indicating that glycosylation of the native protein by the GalNAc oxazoline occurred.

Example 4: In a manner similar to that described above, TACT was converted to the corresponding carbohydrate oxazoline with CDMBI, which was subsequently reacted with MDH for about 16 hours at room temperature. SDS-PAGE electrophoresis of the resulting modified protein showed a discernible shift indicating that glycosylation of the native protein by the TACT oxazoline occurred.

Example 5: In a manner similar to that described above, LewB4 was converted to the corresponding carbohydrate oxazoline with CDMBI, which was subsequently reacted with MDH for about 16 hours at room temperature. SDS-PAGE electrophoresis of the resulting modified protein showed a discernible shift indicating that glycosylation of the native protein by the LewB4 oxazoline occurred.

Example 6: In a manner similar to that described above, HA6 was converted to the corresponding carbohydrate oxazoline with CDMBI, which was subsequently reacted with MDH for about 16 hours at room temperature. SDS-PAGE electrophoresis of the resulting modified protein showed a discernible shift indicating that glycosylation of the native protein by the HA6 oxazoline occurred.

Example 7: In a manner similar to that described above. HA50 was converted to the corresponding carbohydrate oxazoline with CDMBI, which was subsequently reacted with MDH for about 16 hours at room temperature. SDS-PAGE electrophoresis of the resulting modified protein showed a discernible shift indicating that glycosylation of the native protein by the HA50 oxazoline occurred.

Example 8: In a manner similar to that described above. N-propanylglucosamine was converted to the corresponding carbohydrate oxazoline with CDMBI, which was subsequently reacted with MDH for about 16 hours at room temperature. SDS-PAGE electrophoresis of the resulting modified protein showed a discernible shift indicating that glycosylation of the native protein by the N-propanylglucosamine oxazoline occurred.

Example 9: In a manner similar to that described above, N-n-butanylglucosamine was converted to the corresponding carbohydrate oxazoline with CDMBI, which was subsequently reacted with MDH for about 16 hours at room temperature. SDS-PAGE electrophoresis of the resulting modified protein showed a discernible shift indicating that glycosylation of the native protein by the N-n-butanylglucosamine oxazoline occurred.

Example 10: In a manner similar to that described above. N-isopropanylglucosamine was converted to the corresponding carbohydrate oxazoline with CDMBI, which was subsequently reacted with MDH for about 16 hours at room temperature. SDS-PAGE electrophoresis of the resulting modified protein showed a discernible shift indicating that glycosylation of the native protein by the N-isopropanylglucosamine oxazoline occurred.

Example 11: In a manner similar to that described above. N-2,2,dimethylpropanylglucosamine was converted to the corresponding carbohydrate oxazoline with CDMBI, which was subsequently reacted with MDH for about 16 hours at room temperature. SDS-PAGE electrophoresis of the resulting modified protein showed a discernible shift indicating that glycosylation of the native protein by the N-2,2,dimethylpropanylglucosamine oxazoline occurred.

Example 12: In a manner similar to that described above, N-((2-oxoethoxy)-propanyl)glucosamine was converted to the corresponding carbohydrate oxazoline with CDMBI, which was subsequently reacted with MDH for about 16 hours at room temperature. SDS-PAGE electrophoresis of the resulting modified protein showed a discernible shift indicating that glycosylation of the native protein by the N-((2-oxoethoxy)-propanyl)glucosamine oxazoline occurred.

Example 13: In a manner similar to that described above, GlcNAc was converted to the corresponding carbohydrate oxazoline with CDMBI, which was subsequently reacted with ADH for about 16 hours at room temperature. SDS-PAGE electrophoresis of the resulting modified protein showed a discernible shift indicating that glycosylation of the native protein by the GlcNAc oxazoline occurred. The glycosylated ADH was desalted and assayed for enzymatic activity as described above.

Example 14: In a manner similar to that described above, TACT was converted to the corresponding carbohydrate oxazoline with CDMBI, which was subsequently reacted with ADH for about 16 hours at room temperature. SDS-PAGE electrophoresis of the resulting modified protein showed a discernible shift indicating that glycosylation of the native protein by the TACT oxazoline occurred. The glycosylated ADH was desalted and assayed for enzymatic activity as described above.

Example 15: In a manner similar to that described above. HA6 was converted to the corresponding carbohydrate oxazoline with CDMBI, which was subsequently reacted with ADH for about 16 hours at room temperature. SDS-PAGE electrophoresis of the resulting modified protein showed a discernible shift indicating that glycosylation of the native protein by the HA6 oxazoline occurred. The glycosylated ADH was desalted and assayed for enzymatic activity as described above.

Example 16: In a manner similar to that described above, HA50 was converted to the corresponding carbohydrate oxazoline with CDMBI, which was subsequently reacted with ADH for about 16 hours at room temperature. SDS-PAGE electrophoresis of the resulting modified protein showed a discernible shift indicating that glycosylation of the native protein by the HA50 oxazoline occurred. The glycosylated ADH was desalted and assayed for enzymatic activity as described above.

Example 17: In a manner similar to that described above. GlcNAc was converted to the corresponding carbohydrate oxazoline with CDMBI, which was subsequently reacted with CDH for about 16 hours at room temperature. SDS-PAGE electrophoresis of the resulting modified protein showed a discernible shift indicating that glycosylation of the native protein by the GlcNAc oxazoline occurred. The glycosylated ADH was desalted and assayed for enzymatic activity as described above.

Example 18: In a manner similar to that described above. TACT was converted to the corresponding carbohydrate oxazoline with CDMBI, which was subsequently reacted with CDH for about 16 hours at room temperature. SDS-PAGE electrophoresis of the resulting modified protein showed a discernible shift indicating that glycosylation of the native protein by the TACT oxazoline occurred. The glycosylated ADH was desalted and assayed for enzymatic activity as described above.

Example 19: In a manner similar to that described above, HA6 was converted to the corresponding carbohydrate oxazoline with CDMBI, which was subsequently reacted with CDH for about 16 hours at room temperature. SDS-PAGE electrophoresis of the resulting modified protein showed a discernible shift indicating that glycosylation of the native protein by the HA6 oxazoline occurred. The glycosylated ADH was desalted and assayed for enzymatic activity as described above.

Example 20: In a manner similar to that described above. HA50 was converted to the corresponding carbohydrate oxazoline with CDMBI, which was subsequently reacted with CDH for about 16 hours at room temperature. SDS-PAGE electrophoresis of the resulting modified protein showed a discernible shift indicating that glycosylation of the native protein by the HA50 oxazoline occurred. The glycosylated ADH was desalted and assayed for enzymatic activity as described above.

Example 21: In a manner similar to that described above, GlcNAc was converted to the corresponding carbohydrate oxazoline with CDMBI, which was subsequently reacted with GDH for about 16 hours at room temperature. SDS-PAGE electrophoresis of the resulting modified protein showed a discernible shift indicating that glycosylation of the native protein by the GlcNAc oxazoline occurred.

Example 22: In a manner similar to that described above. TACT was converted to the corresponding carbohydrate oxazoline with CDMBI, which was subsequently reacted with GDH for about 16 hours at room temperature. SDS-PAGE electrophoresis of the resulting modified protein showed a discernible shift indicating that glycosylation of the native protein by the TACT oxazoline occurred.

Example 23: In a manner similar to that described above. HA6 was converted to the corresponding carbohydrate oxazoline with CDMBI, which was subsequently reacted with GDH for about 16 hours at room temperature. SDS-PAGE electrophoresis of the resulting modified protein showed a discernible shift indicating that glycosylation of the native protein by the HA6 oxazoline occurred.

Example 24: In a manner similar to that described above. HA50 was converted to the corresponding carbohydrate oxazoline with CDMBI, which was subsequently reacted with GDH for about 16 hours at room temperature. SDS-PAGE electrophoresis of the resulting modified protein showed a discernible shift indicating that glycosylation of the native protein by the HA50 oxazoline occurred.

Example 25: In a manner similar to that described above, GlcNAc was converted to the corresponding carbohydrate oxazoline with CDMBI, which was subsequently reacted with LDH for about 16 hours at room temperature. SDS-PAGE electrophoresis of the resulting modified protein showed a discernible shift indicating that glycosylation of the native protein by the GlcNAc oxazoline occurred. The glycosylated LDH was desalted and assayed for enzymatic activity as described above.

Example 26: In a manner similar to that described above, TACT was converted to the corresponding carbohydrate oxazoline with CDMBI, which was subsequently reacted with LDH for about 16 hours at room temperature. SDS-PAGE electrophoresis of the resulting modified protein showed a discernible shift indicating that glycosylation of the native protein by the TACT oxazoline occurred. The glycosylated LDH was desalted and assayed for enzymatic activity as described above.

Example 27: In a manner similar to that described above, HA6 was converted to the corresponding carbohydrate oxazoline with CDMBI, which was subsequently reacted with LDH for about 16 hours at room temperature. SDS-PAGE electrophoresis of the resulting modified protein showed a discernible shift indicating that glycosylation of the native protein by the HA6 oxazoline occurred. The glycosylated LDH was desalted and assayed for enzymatic activity as described above.

Example 28: In a manner similar to that described above. HA50 was converted to the corresponding carbohydrate oxazoline with CDMBI, which was subsequently reacted with LDH for about 16 hours at room temperature. SDS-PAGE electrophoresis of the resulting modified protein showed a discernible shift indicating that glycosylation of the native protein by the HA50 oxazoline occurred. The glycosylated LDH was desalted and assayed for enzymatic activity as described above.

Example 29: In a manner similar to that described above, GlcNAc was converted to the corresponding carbohydrate oxazoline with CDMBI, which was subsequently reacted with AOx for about 16 hours at room temperature. SDS-PAGE electrophoresis of the resulting modified protein showed a discernible shift indicating that glycosylation of the native protein by the GlcNAc oxazoline occurred. The glycosylated AOx was desalted and assayed for enzymatic activity as described above.

Example 30: In a manner similar to that described above, TACT was converted to the corresponding carbohydrate oxazoline with CDMBI, which was subsequently reacted with AOx for about 16 hours at room temperature. SDS-PAGE electrophoresis of the resulting modified protein showed a discernible shift indicating that glycosylation of the native protein by the TACT oxazoline occurred. The glycosylated AOx was desalted and assayed for enzymatic activity as described above.

Example 31: In a manner similar to that described above. HA6 was converted to the corresponding carbohydrate oxazoline with CDMBI, which was subsequently reacted with AOx for about 16 hours at room temperature. SDS-PAGE electrophoresis of the resulting modified protein showed a discernible shift indicating that glycosylation of the native protein by the HA6 oxazoline occurred. The glycosylated AOx was desalted and assayed for enzymatic activity as described above.

Example 32: In a manner similar to that described above, HA50 was converted to the corresponding carbohydrate oxazoline with CDMBI, which was subsequently reacted with AOx for about 16 hours at room temperature. SDS-PAGE electrophoresis of the resulting modified protein showed a discernible shift indicating that glycosylation of the native protein by the HA50 oxazoline occurred. The glycosylated AOx was desalted and assayed for enzymatic activity as described above.

Example 33: In a manner similar to that described above. GlcNAc was converted to the corresponding carbohydrate oxazoline with CDMBI, which was subsequently reacted with MBP-COx1 for about 16 hours at room temperature. SDS-PAGE electrophoresis of the resulting modified protein showed a discernible shift indicating that glycosylation of the native protein by the GlcNAc oxazoline occurred. The glycosylated MBP-COx1 was desalted and assayed for enzymatic activity as described above.

Example 34: In a manner similar to that described above. TACT was converted to the corresponding carbohydrate oxazoline with CDMBI, which was subsequently reacted with MBP-COx1 for about 16 hours at room temperature. SDS-PAGE electrophoresis of the resulting modified protein showed a discernible shift indicating that glycosylation of the native protein by the TACT oxazoline occurred. The glycosylated MBP-COx1 was desalted and assayed for enzymatic activity as described above.

Example 35: In a manner similar to that described above, HA6 was converted to the corresponding carbohydrate oxazoline with CDMBI, which was subsequently reacted with MBP-COx1 for about 16 hours at room temperature. SDS-PAGE electrophoresis of the resulting modified protein showed a discernible shift indicating that glycosylation of the native protein by the HA6 oxazoline occurred. The glycosylated MBP-COx1 was desalted and assayed for enzymatic activity as described above.

Example 36: In a manner similar to that described above. HA50 was converted to the corresponding carbohydrate oxazoline with CDMBI, which was subsequently reacted with MBP-COx1 for about 16 hours at room temperature. SDS-PAGE electrophoresis of the resulting modified protein showed a discernible shift indicating that glycosylation of the native protein by the HA50 oxazoline occurred. The glycosylated MBP-COx1 was desalted and assayed for enzymatic activity as described above.

Example 37: In a manner similar to that described above, GlcNAc was converted to the corresponding carbohydrate oxazoline with CDMBI, which was subsequently reacted with COx2 for about 16 hours at room temperature. SDS-PAGE electrophoresis of the resulting modified protein showed a discernible shift indicating that glycosylation of the native protein by the GlcNAc oxazoline occurred. The glycosylated COx2 was desalted and assayed for enzymatic activity as described above.

Example 38: In a manner similar to that described above, TACT was converted to the corresponding carbohydrate oxazoline with CDMBI, which was subsequently reacted with COx2 for about 16 hours at room temperature. SDS-PAGE electrophoresis of the resulting modified protein showed a discernible shift indicating that glycosylation of the native protein by the TACT oxazoline occurred. The glycosylated COx2 was desalted and assayed for enzymatic activity as described above.

Example 39: In a manner similar to that described above, HA6 was converted to the corresponding carbohydrate oxazoline with CDMBI, which was subsequently reacted with COx2 for about 16 hours at room temperature. SDS-PAGE electrophoresis of the resulting modified protein showed a discernible shift indicating that glycosylation of the native protein by the HA6 oxazoline occurred. The glycosylated COx2 was desalted and assayed for enzymatic activity as described above.

Example 40: In a manner similar to that described above, HA50 was converted to the corresponding carbohydrate oxazoline with CDMBI, which was subsequently reacted with COx2 for about 16 hours at room temperature. SDS-PAGE electrophoresis of the resulting modified protein showed a discernible shift indicating that glycosylation of the native protein by the HA50 oxazoline occurred. The glycosylated COx2 was desalted and assayed for enzymatic activity as described above.

Example 41: In a manner similar to that described above. GlcNAc was converted to the corresponding carbohydrate oxazoline with CDMBI, which was subsequently reacted with GlutOx for about 16 hours at room temperature. SDS-PAGE electrophoresis of the resulting modified protein showed a discernible shift indicating that glycosylation of the native protein by the GlcNAc oxazoline occurred. The glycosylated GlutOx was desalted and assayed for enzymatic activity as described above.

Example 42: In a manner similar to that described above. TACT was converted to the corresponding carbohydrate oxazoline with CDMBI, which was subsequently reacted with GlutOx for about 16 hours at room temperature. SDS-PAGE electrophoresis of the resulting modified protein showed a discernible shift indicating that glycosylation of the native protein by the TACT oxazoline occurred. The glycosylated GlutOx was desalted and assayed for enzymatic activity as described above.

Example 43: In a manner similar to that described above. HA6 was converted to the corresponding carbohydrate oxazoline with CDMBI, which was subsequently reacted with GlutOx for about 16 hours at room temperature. SDS-PAGE electrophoresis of the resulting modified protein showed a discernible shift indicating that glycosylation of the native protein by the HA6 oxazoline occurred. The glycosylated GlutOx was desalted and assayed for enzymatic activity as described above.

Example 44: In a manner similar to that described above, HA50 was converted to the corresponding carbohydrate oxazoline with CDMBI, which was subsequently reacted with GlutOx for about 16 hours at room temperature. SDS-PAGE electrophoresis of the resulting modified protein showed a discernible shift indicating that glycosylation of the native protein by the HA50 oxazoline occurred. The glycosylated GlutOx was desalted and assayed for enzymatic activity as described above.

Example 45: In a manner similar to that described above, GlcNAc was converted to the corresponding carbohydrate oxazoline with CDMBI, which was subsequently reacted with GlyOx for about 16 hours at room temperature. SDS-PAGE electrophoresis of the resulting modified protein showed a discernible shift indicating that glycosylation of the native protein by the GlcNAc oxazoline occurred. The glycosylated GlyOx was desalted and assayed for enzymatic activity as described above.

Example 46: In a manner similar to that described above, TACT was converted to the corresponding carbohydrate oxazoline with CDMBI, which was subsequently reacted with GlyOx for about 16 hours at room temperature. SDS-PAGE electrophoresis of the resulting modified protein showed a discernible shift indicating that glycosylation of the native protein by the TACT oxazoline occurred. The glycosylated GlyOx was desalted and assayed for enzymatic activity as described above.

Example 47: In a manner similar to that described above. HA6 was converted to the corresponding carbohydrate oxazoline with CDMBI, which was subsequently reacted with GlyOx for about 16 hours at room temperature. SDS-PAGE electrophoresis of the resulting modified protein showed a discernible shift indicating that glycosylation of the native protein by the HA6 oxazoline occurred. The glycosylated GlyOx was desalted and assayed for enzymatic activity as described above.

Example 48: In a manner similar to that described above, HA50 was converted to the corresponding carbohydrate oxazoline with CDMBI, which was subsequently reacted with GlyOx for about 16 hours at room temperature. SDS-PAGE electrophoresis of the resulting modified protein showed a discernible shift indicating that glycosylation of the native protein by the HA50 oxazoline occurred. The glycosylated GlyOx was desalted and assayed for enzymatic activity as described above.

Example 49: In a manner similar to that described above, GlcNAc was converted to the corresponding carbohydrate oxazoline with CDMBI, which was subsequently reacted with NicOx for about 16 hours at room temperature. SDS-PAGE electrophoresis of the resulting modified protein showed a discernible shift indicating that glycosylation of the native protein by the GlcNAc oxazoline occurred. The glycosylated NicOx was desalted and assayed for enzymatic activity as described above.

Example 50: In a manner similar to that described above, TACT was converted to the corresponding carbohydrate oxazoline with CDMBI, which was subsequently reacted with NicOx for about 16 hours at room temperature. SDS-PAGE electrophoresis of the resulting modified protein showed a discernible shift indicating that glycosylation of the native protein by the TACT oxazoline occurred. The glycosylated NicOx was desalted and assayed for enzymatic activity as described above.

Example 51: In a manner similar to that described above, HA6 was converted to the corresponding carbohydrate oxazoline with CDMBI, which was subsequently reacted with NicOx for about 16 hours at room temperature. SDS-PAGE electrophoresis of the resulting modified protein showed a discernible shift indicating that glycosylation of the native protein by the HA6 oxazoline occurred. The glycosylated NicOx was desalted and assayed for enzymatic activity as described above.

Example 52: In a manner similar to that described above. HA50 was converted to the corresponding carbohydrate oxazoline with CDMBI, which was subsequently reacted with NicOx for about 16 hours at room temperature. SDS-PAGE electrophoresis of the resulting modified protein showed a discernible shift indicating that glycosylation of the native protein by the HA50 oxazoline occurred. The glycosylated NicOx was desalted and assayed for enzymatic activity as described above.

Example 53: In a manner similar to that described above, GlcNAc was converted to the corresponding carbohydrate oxazoline with CDMBI, which was subsequently reacted with MBP-PutOx for about 16 hours at room temperature. SDS-PAGE electrophoresis of the resulting modified protein showed a discernible shift indicating that glycosylation of the native protein by the GlcNAc oxazoline occurred. The glycosylated MBP-PutOx was desalted and assayed for enzymatic activity as described above.

Example 54: In a manner similar to that described above, TACT was converted to the corresponding carbohydrate oxazoline with CDMBI, which was subsequently reacted with MBP-PutOx for about 16 hours at room temperature. SDS-PAGE electrophoresis of the resulting modified protein showed a discernible shift indicating that glycosylation of the native protein by the TACT oxazoline occurred. The glycosylated MBP-PutOx was desalted and assayed for enzymatic activity as described above.

Example 55: In a manner similar to that described above, HA6 was converted to the corresponding carbohydrate oxazoline with CDMBI, which was subsequently reacted with MBP-PutOx for about 16 hours at room temperature. SDS-PAGE electrophoresis of the resulting modified protein showed a discernible shift indicating that glycosylation of the native protein by the HA6 oxazoline occurred. The glycosylated MBP-PutOx was desalted and assayed for enzymatic activity as described above.

Example 56: In a manner similar to that described above, HA50 was converted to the corresponding carbohydrate oxazoline with CDMBI, which was subsequently reacted with MBP-PutOx for about 16 hours at room temperature. SDS-PAGE electrophoresis of the resulting modified protein showed a discernible shift indicating that glycosylation of the native protein by the HA50 oxazoline occurred. The glycosylated MBP-PutOx was desalted and assayed for enzymatic activity as described above.

Example 57: In a manner similar to that described above. GlcNAc was converted to the corresponding carbohydrate oxazoline with CDMBI, which was subsequently reacted with SOx for about 16 hours at room temperature. SDS-PAGE electrophoresis of the resulting modified protein showed a discernible shift indicating that glycosylation of the native protein by the GlcNAc oxazoline occurred. The glycosylated SOx was desalted and assayed for enzymatic activity as described above.

Example 58: In a manner similar to that described above, TACT was converted to the corresponding carbohydrate oxazoline with CDMBI, which was subsequently reacted with SOx for about 16 hours at room temperature. SDS-PAGE electrophoresis of the resulting modified protein showed a discernible shift indicating that glycosylation of the native protein by the TACT oxazoline occurred. The glycosylated SOx was desalted and assayed for enzymatic activity as described above.

Example 59: In a manner similar to that described above, HA6 was converted to the corresponding carbohydrate oxazoline with CDMBI, which was subsequently reacted with SOx for about 16 hours at room temperature. SDS-PAGE electrophoresis of the resulting modified protein showed a discernible shift indicating that glycosylation of the native protein by the HA6 oxazoline occurred. The glycosylated SOx was desalted and assayed for enzymatic activity as described above.

Example 60: In a manner similar to that described above, HA50 was converted to the corresponding carbohydrate oxazoline with CDMBI, which was subsequently reacted with SOx for about 16 hours at room temperature. SDS-PAGE electrophoresis of the resulting modified protein showed a discernible shift indicating that glycosylation of the native protein by the HA50 oxazoline occurred. The glycosylated SOx was desalted and assayed for enzymatic activity as described above.

Example 61: In a manner similar to that described above. LewB4 was converted to the corresponding carbohydrate oxazoline with CDMBI, which was subsequently reacted with SOx for about 16 hours at room temperature. SDS-PAGE electrophoresis of the resulting modified protein showed a discernible shift indicating that glycosylation of the native protein by the LewB4 oxazoline occurred. The glycosylated SOx was desalted and assayed for enzymatic activity as described above.

Example 62: In a manner similar to that described above. Man-3 was converted to the corresponding carbohydrate oxazoline with CDMBI, which was subsequently reacted with SOx for about 48-72 hours at room temperature. SDS-PAGE electrophoresis of the resulting modified protein showed a discernible shift indicating that glycosylation of the native protein by the Man-3 oxazoline occurred. The glycosylated SOx was desalted and assayed for enzymatic activity as described above.

Example 63: In a manner similar to that described above, Man-5 was converted to the corresponding carbohydrate oxazoline with CDMBI, which was subsequently reacted with SOx for about 48-72 hours at room temperature. SDS-PAGE electrophoresis of the resulting modified protein showed a discernible shift indicating that glycosylation of the native protein by the Man-5 oxazoline occurred. The glycosylated SOx was desalted and assayed for enzymatic activity as described above.

Example 64: In a manner similar to that described above. GlcNAc was converted to the corresponding carbohydrate oxazoline with CDMBI, which was subsequently reacted with GOx for about 16 hours at room temperature. SDS-PAGE electrophoresis of the resulting modified protein showed a discernible shift indicating that glycosylation of the native protein by the GlcNAc oxazoline occurred. The glycosylated GOx was desalted and assayed for enzymatic activity as described above.

Example 65: In a manner similar to that described above, TACT was converted to the corresponding carbohydrate oxazoline with CDMBI, which was subsequently reacted with GOx for about 16 hours at room temperature. SDS-PAGE electrophoresis of the resulting modified protein showed a discernible shift indicating that glycosylation of the native protein by the TACT oxazoline occurred. The glycosylated GOx was desalted and assayed for enzymatic activity as described above.

Example 66: In a manner similar to that described above, HA6 was converted to the corresponding carbohydrate oxazoline with CDMBI, which was subsequently reacted with GOx for about 16 hours at room temperature. SDS-PAGE electrophoresis of the resulting modified protein showed a discernible shift indicating that glycosylation of the native protein by the HA6 oxazoline occurred. The glycosylated GOx was desalted and assayed for enzymatic activity as described above.

Example 67: In a manner similar to that described above. HA50 was converted to the corresponding carbohydrate oxazoline with CDMBI, which was subsequently reacted with GOx for about 16 hours at room temperature. SDS-PAGE electrophoresis of the resulting modified protein showed a discernible shift indicating that glycosylation of the native protein by the HA50 oxazoline occurred. The glycosylated GOx was desalted and assayed for enzymatic activity as described above.

Example 68: In a manner similar to that described above, GlcNAc was converted to the corresponding carbohydrate oxazoline with CDMBI, which was subsequently reacted with MBP-GOx for about 72 hours at room temperature. SDS-PAGE electrophoresis of the resulting modified protein showed a discernible shift indicating that glycosylation of the native protein by the GlcNAc oxazoline occurred. The glycosylated MBP-GOx was desalted and assayed for enzymatic activity as described above.

Example 69: In a manner similar to that described above, TACT was converted to the corresponding carbohydrate oxazoline with CDMBI, which was subsequently reacted with MBP-GOx for about 72 hours at room temperature. SDS-PAGE electrophoresis of the resulting modified protein showed a discernible shift indicating that glycosylation of the native protein by the TACT oxazoline occurred. The glycosylated MBP-GOx was desalted and assayed for enzymatic activity as described above.

Example 70: In a manner similar to that described above. GlcNAc was converted to the corresponding carbohydrate oxazoline with either DMC or CDMBI, which was subsequently reacted with LOx for about 16 hours at room temperature. SDS-PAGE electrophoresis of the resulting modified protein showed a discernible shift indicating that glycosylation of the native protein by the GlcNAc oxazoline occurred. The glycosylated LOx was desalted and assayed for enzymatic activity as described above.

Example 71: In a manner similar to that described above, DACB was converted to the corresponding carbohydrate oxazoline with CDMBI, which was subsequently reacted with LOx for about 16 hours at room temperature. SDS-PAGE electrophoresis of the resulting modified protein showed a discernible shift indicating that glycosylation of the native protein by the DACB oxazoline occurred. The glycosylated LOx was desalted and assayed for enzymatic activity as described above.

Example 72: In a manner similar to that described above. TACT was converted to the corresponding carbohydrate oxazoline with CDMBI, which was subsequently reacted with LOx for about 16 hours at room temperature. SDS- PAGE electrophoresis of the resulting modified protein showed a discernible shift indicating that glycosylation of the native protein by the TACT oxazoline occurred. The glycosylated LOx was desalted and assayed for enzymatic activity as described above.

Example 73: In a manner similar to that described above, HA6 was converted to the corresponding carbohydrate oxazoline with CDMBI, which was subsequently reacted with LOx for about 16 hours at room temperature. SDS-PAGE electrophoresis of the resulting modified protein showed a discernible shift indicating that glycosylation of the native protein by the HA6 oxazoline occurred. The glycosylated LOx was desalted and assayed for enzymatic activity as described above.

Example 74: In a manner similar to that described above, HA50 was converted to the corresponding carbohydrate oxazoline with CDMBI, which was subsequently reacted with LOx for about 16 hours at room temperature. SDS-PAGE electrophoresis of the resulting modified protein showed a discernible shift indicating that glycosylation of the native protein by the HA50 oxazoline occurred. The glycosylated LOx was desalted and assayed for enzymatic activity as described above.

Example 75: In a manner similar to that described above, GlcNAc was converted to the corresponding carbohydrate oxazoline with CDMBI, which was subsequently reacted with MBP-LOx for about 72 hours at room temperature. SDS-PAGE electrophoresis of the resulting modified protein showed a discernible shift indicating that glycosylation of the native protein by the GlcNAc oxazoline occurred. The glycosylated MBP-LOx was desalted and assayed for enzymatic activity as described above.

Example 76: In a manner similar to that described above, TACT was converted to the corresponding carbohydrate oxazoline with CDMBI, which was subsequently reacted with MBP-LOx for about 72 hours at room temperature. SDS-PAGE electrophoresis of the resulting modified protein showed a discernible shift indicating that glycosylation of the native protein by the TACT oxazoline occurred. The glycosylated MBP-LOx was desalted and assayed for enzymatic activity as described above.

Example 77: In a manner similar to that described above. TACT was converted to the corresponding carbohydrate oxazoline with CDMBI, which was subsequently reacted with SOx at a pH of 6 for about 16 hours at room temperature. SDS-PAGE electrophoresis of the resulting modified protein showed a discernible shift indicating that glycosylation of the native protein by the TACT oxazoline occurred.

Example 78: In a manner similar to that described above. TACT was converted to the corresponding carbohydrate oxazoline with CDMBI, which was subsequently reacted with SOx at a pH of 7 for about 16 hours at room temperature. SDS-PAGE electrophoresis of the resulting modified protein showed a discernible shift indicating that glycosylation of the native protein by the TACT oxazoline occurred.

Example 79: In a manner similar to that described above, GlcNAc was converted to the corresponding carbohydrate oxazoline with CDMBI, which was subsequently reacted with CortDH for about 16 hours at room temperature. SDS-PAGE electrophoresis of the resulting modified protein showed a discernible shift indicating that glycosylation of the native protein by the GlcNAc oxazoline occurred. The glycosylated CortDH was desalted and assayed for enzymatic activity as described above.

Example 80: In a manner similar to that described above. TACT was convened to the corresponding carbohydrate oxazoline with CDMBI, which was subsequently reacted with CortDH for about 16 hours at room temperature. SDS-PAGE electrophoresis of the resulting modified protein showed a discernible shift indicating that glycosylation of the native protein by the TACT oxazoline occurred. The glycosylated CortDH was desalted and assayed for enzymatic activity as described above.

Example 81: In a manner similar to that described above, HA6 was converted to the corresponding carbohydrate oxazoline with CDMBI, which was subsequently reacted with CortDH for about 16 hours at room temperature. SDS-PAGE electrophoresis of the resulting modified protein showed a discernible shift indicating that glycosylation of the native protein by the HA6 oxazoline occurred. The glycosylated CortDH was desalted and assayed for enzymatic activity as described above.

Example 82: In a manner similar to that described above, HA50 was converted to the corresponding carbohydrate oxazoline with CDMBI, which was subsequently reacted with CortDH for about 16 hours at room temperature. SDS-PAGE electrophoresis of the resulting modified protein showed a discernible shift indicating that glycosylation of the native protein by the HA50 oxazoline occurred. The glycosylated CortDH was desalted and assayed for enzymatic activity as described above.

Example 83: In the following hypothetical example and in a manner similar to that described above, partially deacetylated chitin is converted to the corresponding carbohydrate oxazoline with CDMBI, which is subsequently reacted with GOx for about 16 hours at room temperature. SDS-PAGE electrophoresis of the resulting modified protein shows a discernible shift indicating that glycosylation of the native protein by the partially deacetylated chitin oxazoline occurs. The glycosylated GOx is desalted and assayed for enzymatic activity as described above.

Example 84: In the following hypothetical example and in a manner similar to that described above, partially deacetylated chitin is converted to the corresponding carbohydrate oxazoline with CDMBI, which is subsequently reacted with MBP-GOx for about 16 hours at room temperature. SDS-PAGE electrophoresis of the resulting modified protein shows a discernible shift indicating that glycosylation of the native protein by the partially deacetylated chitin oxazoline occurs. The glycosylated MBP-GOx is desalted and assayed for enzymatic activity as described above.

Example 85: In the following hypothetical example and in a manner similar to that described above, partially deacetylated chitin is converted to the corresponding carbohydrate oxazoline with CDMBI, which is subsequently reacted with LOx for about 16 hours at room temperature. SDS-PAGE electrophoresis of the resulting modified protein shows a discernible shift indicating that glycosylation of the native protein by the partially deacetylated chitin oxazoline occurs. The glycosylated LOx is desalted and assayed for enzymatic activity as described above.

Example 86: In the following hypothetical example and in a manner similar to that described above, partially deacetylated chitin is converted to the corresponding carbohydrate oxazoline with CDMBI, which is subsequently reacted with MBP-LOx for about 16 hours at room temperature. SDS-PAGE electrophoresis of the resulting modified protein shows a discernible shift indicating that glycosylation of the native protein by the partially deacetylated chitin oxazoline occurs. The glycosylated MBP-LOx is desalted and assayed for enzymatic activity as described above.

Example 87: In the following hypothetical example and in a manner similar to that described above, partially deacetylated chitin is converted to the corresponding carbohydrate oxazoline with CDMBI, which is subsequently reacted with AOx for about 16 hours at room temperature. SDS-PAGE electrophoresis of the resulting modified protein shows a discernible shift indicating that glycosylation of the native protein by the partially deacetylated chitin oxazoline occurs. The glycosylated AOx is desalted and assayed for enzymatic activity as described above.

Example 88: In the following hypothetical example and in a manner similar to that described above, partially deacetylated chitin is converted to the corresponding carbohydrate oxazoline with CDMBI, which is subsequently reacted with MBP-AOx for about 16 hours at room temperature. SDS-PAGE electrophoresis of the resulting modified protein shows a discernible shift indicating that glycosylation of the native protein by the partially deacetylated chitin oxazoline occurs. The glycosylated MBP-AOx is desalted and assayed for enzymatic activity as described above.

Example 89: In the following hypothetical example and in a manner similar to that described above. HA50 is converted to the corresponding carbohydrate oxazoline with CDMBI, which is subsequently reacted with MBP-AOx for about 16 hours at room temperature. SDS-PAGE electrophoresis of the resulting modified protein shows a discernible shift indicating that glycosylation of the native protein by the HA50 oxazoline occurs. The glycosylated MBP-AOx is desalted and assayed for enzymatic activity as described above.

Example 90: In the following hypothetical example and in a manner similar to that described above, partially deacetylated chitin is converted to the corresponding carbohydrate oxazoline with CDMBI, which is subsequently reacted with GlutOx for about 16 hours at room temperature. SDS-PAGE electrophoresis of the resulting modified protein shows a discernible shift indicating that glycosylation of the native protein by the partially deacetylated chitin oxazoline occurs. The glycosylated GlutOx is desalted and assayed for enzymatic activity as described above.

Example 91: In the following hypothetical example and in a manner similar to that described above, partially deacetylated chitin is converted to the corresponding carbohydrate oxazoline with CDMBI, which is subsequently reacted with MBP-GlutOx for about 16 hours at room temperature. SDS-PAGE electrophoresis of the resulting modified protein shows a discernible shift indicating that glycosylation of the native protein by the partially deacetylated chitin oxazoline occurs. The glycosylated MBP-GlutOx is desalted and assayed for enzymatic activity as described above.

Example 92: In the following hypothetical example and in a manner similar to that described above, HA50 is converted to the corresponding carbohydrate oxazoline with CDMBI, which is subsequently reacted with MBP-GlutOx for about 16 hours at room temperature. SDS-PAGE electrophoresis of the resulting modified protein shows a discernible shift indicating that glycosylation of the native protein by the HA50 oxazoline occurs. The glycosylated MBP-GlutOx is desalted and assayed for enzymatic activity as described above.

Example 93: In the following hypothetical example and in a manner similar to that described above, partially deacetylated chitin is converted to the corresponding carbohydrate oxazoline with CDMBI, which is subsequently reacted with choline oxidase for about 16 hours at room temperature. SDS-PAGE electrophoresis of the resulting modified protein shows a discernible shift indicating that glycosylation of the native protein by the partially deacetylated chitin oxazoline occurs. The glycosylated choline oxidase is desalted and assayed for enzymatic activity as described above.

Example 94: In the following hypothetical example and in a manner similar to that described above, HA50 is converted to the corresponding carbohydrate oxazoline with CDMBI, which is subsequently reacted with choline oxidase for about 16 hours at room temperature. SDS-PAGE electrophoresis of the resulting modified protein shows a discernible shift indicating that glycosylation of the native protein by the HA50 oxazoline occurs. The glycosylated choline oxidase is desalted and assayed for enzymatic activity as described above.

Example 95: In the following hypothetical example and in a manner similar to that described above, partially deacetylated chitin is converted to the corresponding carbohydrate oxazoline with CDMBI, which is subsequently reacted with SOx for about 16 hours at room temperature. SDS-PAGE electrophoresis of the resulting modified protein shows a discernible shift indicating that glycosylation of the native protein by the partially deacetylated chitin oxazoline occurs. The glycosylated SOx is desalted and assayed for enzymatic activity as described above.

Example 96: In the following hypothetical example and in a manner similar to that described above, HA50 is converted to the corresponding carbohydrate oxazoline with CDMBI, which is subsequently reacted with MBP-COx2 for about 16 hours at room temperature. SDS-PAGE electrophoresis of the resulting modified protein shows a discernible shift indicating that glycosylation of the native protein by the HA50 oxazoline occurs. The glycosylated MBP-COx2 is desalted and assayed for enzymatic activity as described above.

Example 97: In the following hypothetical example and in a manner similar to that described above, partially deacetylated chitin is converted to the corresponding carbohydrate oxazoline with CDMBI, which is subsequently reacted with MBP-COx2 for about 16 hours at room temperature. SDS-PAGE electrophoresis of the resulting modified protein shows a discernible shift indicating that glycosylation of the native protein by the partially deacetylated chitin oxazoline occurs. The glycosylated MBP-COx2 is desalted and assayed for enzymatic activity as described above.

Example 98: In the following hypothetical example and in a manner similar to that described above, partially deacetylated chitin is converted to the corresponding carbohydrate oxazoline with CDMBI, which is subsequently reacted with xanthine oxidase for about 16 hours at room temperature. SDS-PAGE electrophoresis of the resulting modified protein shows a discernible shift indicating that glycosylation of the native protein by the partially deacetylated chitin oxazoline occurs. The glycosylated xanthine oxidase is desalted and assayed for enzymatic activity as described above.

Example 99: In the following hypothetical example and in a manner similar to that described above. HA50 is converted to the corresponding carbohydrate oxazoline with CDMBI, which is subsequently reacted with xanthine oxidase for about 16 hours at room temperature. SDS-PAGE electrophoresis of the resulting modified protein shows a discernible shift indicating that glycosylation of the native protein by the HA50 oxazoline occurs. The glycosylated xanthine oxidase is desalted and assayed for enzymatic activity as described above.

Example 100: In the following hypothetical example and in a manner similar to that described above, partially deacetylated chitin is convened to the corresponding carbohydrate oxazoline with CDMBI, which is subsequently reacted with MBP-xanthine oxidase for about 16 hours at room temperature. SDS-PAGE electrophoresis of the resulting modified protein shows a discernible shift indicating that glycosylation of the native protein by the partially deacetylated chitin oxazoline occurs. The glycosylated MBP-xanthine oxidase is desalted and assayed for enzymatic activity as described above.

Example 101: In the following hypothetical example and in a manner similar to that described above, HA50 is converted to the corresponding carbohydrate oxazoline with CDMBI, which is subsequently reacted with xanthine oxidase for about 16 hours at room temperature. SDS-PAGE electrophoresis of the resulting modified protein shows a discernible shift indicating that glycosylation of the native protein by the HA50 oxazoline occurs. The glycosylated MBP-xanthine oxidase is desalted and assayed for enzymatic activity as described above.

Example 102: In the following hypothetical example and in a manner similar to that described above. HA50 is converted to the corresponding carbohydrate oxazoline with CDMBI, which is subsequently reacted with COx1 for about 16 hours at room temperature. SDS-PAGE electrophoresis of the resulting modified protein shows a discernible shift indicating that glycosylation of the native protein by the HA50 oxazoline occurs. The glycosylated COx1 is desalted and assayed for enzymatic activity as described above.

Example 103: In the following hypothetical example and in a manner similar to that described above, partially deacetylated chitin is convened to the corresponding carbohydrate oxazoline with CDMBI, which is subsequently reacted with COx1 for about 16 hours at room temperature. SDS-PAGE electrophoresis of the resulting modified protein shows a discernible shift indicating that glycosylation of the native protein by the partially deacetylated chitin oxazoline occurs. The glycosylated COx1 is desalted and assayed for enzymatic activity as described above.

Example 104: In the following hypothetical example and in a manner similar to that described above, partially deacetylated chitin is converted to the corresponding carbohydrate oxazoline with CDMBI, which is subsequently reacted with MBP-COx1 for about 16 hours at room temperature. SDS-PAGE electrophoresis of the resulting modified protein shows a discernible shift indicating that glycosylation of the native protein by the partially deacetylated chitin oxazoline occurs. The glycosylated MBP-COx1 is desalted and assayed for enzymatic activity as described above.

Example 105: In the following hypothetical example and in a manner similar to that described above, partially deacetylated chitin is converted to the corresponding carbohydrate oxazoline with CDMBI, which is subsequently reacted with COx2 for about 16 hours at room temperature. SDS-PAGE electrophoresis of the resulting modified protein shows a discernible shift indicating that glycosylation of the native protein by the partially deacetylated chitin oxazoline occurs. The glycosylated COx2 is desalted and assayed for enzymatic activity as described above.

Example 106: In the following hypothetical example and in a manner similar to that described above, partially deacetylated chitin is converted to the corresponding carbohydrate oxazoline with CDMBI, which is subsequently reacted with ADH for about 16 hours at room temperature. SDS-PAGE electrophoresis of the resulting modified protein shows a discernible shift indicating that glycosylation of the native protein by the partially deacetylated chitin oxazoline occurs. The glycosylated ADH is desalted and assayed for enzymatic activity as described above.

Example 107: In the following hypothetical example and in a manner similar to that described above, partially deacetylated chitin is converted to the corresponding carbohydrate oxazoline with CDMBI, which is subsequently reacted with GDH for about 16 hours at room temperature. SDS-PAGE electrophoresis of the resulting modified protein shows a discernible shift indicating that glycosylation of the native protein by the partially deacetylated chitin oxazoline occurs. The glycosylated GDH is desalted and assayed for enzymatic activity as described above.

Example 108: In the following hypothetical example and in a manner similar to that described above, partially deacetylated chitin is converted to the corresponding carbohydrate oxazoline with CDMBI, which is subsequently reacted with LDH for about 16 hours at room temperature. SDS-PAGE electrophoresis of the resulting modified protein shows a discernible shift indicating that glycosylation of the native protein by the partially deacetylated chitin oxazoline occurs. The glycosylated LDH is desalted and assayed for enzymatic activity as described above.

Example 109: In the following hypothetical example and in a manner similar to that described above, partially deacetylated chitin is converted to the corresponding carbohydrate oxazoline with CDMBI, which is subsequently reacted with CortDH for about 16 hours at room temperature. SDS-PAGE electrophoresis of the resulting modified protein shows a discernible shift indicating that glycosylation of the native protein by the partially deacetylated chitin oxazoline occurs. The glycosylated CortDH is desalted and assayed for enzymatic activity as described above.

Example 110: In the following hypothetical example and in a manner similar to that described above, partially deacetylated chitin is converted to the corresponding carbohydrate oxazoline with CDMBI, which is subsequently reacted with MDH for about 16 hours at room temperature. SDS-PAGE electrophoresis of the resulting modified protein shows a discernible shift indicating that glycosylation of the native protein by the partially deacetylated chitin oxazoline occurs. The glycosylated MDH is desalted and assayed for enzymatic activity as described above.

Example 111: In the following hypothetical example and in a manner similar to that described above, G2FS2($\alpha$2,3) is converted to the corresponding carbohydrate oxazoline with CDMBI, which is subsequently reacted with MDH for about 16 hours at room temperature. SDS-PAGE electrophoresis of the resulting modified protein shows a discernible shift indicating that glycosylation of the native protein by G2FS2 ($\alpha$2,3) occurs. The glycosylated MDH is desalted and assayed for enzymatic activity as described above.

Example 112: In the following hypothetical example and in a manner similar to that described above, G2FS2($\alpha$2,6) is converted to the corresponding carbohydrate oxazoline with CDMBI, which is subsequently reacted with MDH for about 16 hours at room temperature. SDS-PAGE electrophoresis of the resulting modified protein shows a discernible shift indicating that glycosylation of the native protein by G2FS2 ($\alpha$2,6) occurs. The glycosylated MDH is desalted and assayed for enzymatic activity as described above.

Example 113: In the following hypothetical example and in a manner similar to that described above, G2FS2($\alpha$2,3) is converted to the corresponding carbohydrate oxazoline with CDMBI, which is subsequently reacted with LDH for about 16 hours at room temperature. SDS-PAGE electrophoresis of the resulting modified protein shows a discernible shift indicating that glycosylation of the native protein by G2FS2 ($\alpha$2,3) occurs. The glycosylated LDH is desalted and assayed for enzymatic activity as described above.

Example 114: In the following hypothetical example and in a manner similar to that described above, G2FS2($\alpha$2,6) is converted to the corresponding carbohydrate oxazoline with CDMBI, which is subsequently reacted with LDH for about 16 hours at room temperature. SDS-PAGE electrophoresis of the resulting modified protein shows a discernible shift indicating that glycosylation of the native protein by G2FS2 (α2,6) occurs. The glycosylated LDH is desalted and assayed for enzymatic activity as described above.

Example 115: In the following hypothetical example and in a manner similar to that described above. G2FS2(α2,3) is converted to the corresponding carbohydrate oxazoline with CDMBI, which is subsequently reacted with GDH for about 16 hours at room temperature. SDS-PAGE electrophoresis of the resulting modified protein shows a discernible shift indicating that glycosylation of the native protein by G2FS2 (α2,3) occurs. The glycosylated GDH is desalted and assayed for enzymatic activity as described above.

Example 116: In the following hypothetical example and in a manner similar to that described above. G2FS2(α2,6) is converted to the corresponding carbohydrate oxazoline with CDMBI, which is subsequently reacted with GDH for about 16 hours at room temperature. SDS-PAGE electrophoresis of the resulting modified protein shows a discernible shift indicating that glycosylation of the native protein by G2FS2 (α2,6) occurs. The glycosylated GDH is desalted and assayed for enzymatic activity as described above.

Example 117: In the following hypothetical example and in a manner similar to that described above, G2FS2(α2,3) is converted to the corresponding carbohydrate oxazoline with CDMBI, which is subsequently reacted with CortDH for about 16 hours at room temperature. SDS-PAGE electrophoresis of the resulting modified protein shows a discernible shift indicating that glycosylation of the native protein by G2FS2(α2,3) occurs. The glycosylated CortDH is desalted and assayed for enzymatic activity as described above.

Example 118: In the following hypothetical example and in a manner similar to that described above, G2FS2(α2,6) is converted to the corresponding carbohydrate oxazoline with CDMBI, which is subsequently reacted with CortDH for about 16 hours at room temperature. SDS-PAGE electrophoresis of the resulting modified protein shows a discernible shift indicating that glycosylation of the native protein by G2FS2(α2,6) occurs. The glycosylated CortDH is desalted and assayed for enzymatic activity as described above.

Example 119: In the following hypothetical example and in a manner similar to that described above, G2FS2(α2,3) is converted to the corresponding carbohydrate oxazoline with CDMBI, which is subsequently reacted with ADH for about 16 hours at room temperature. SDS-PAGE electrophoresis of the resulting modified protein shows a discernible shift indicating that glycosylation of the native protein by G2FS2 (α2,3) occurs. The glycosylated ADH is desalted and assayed for enzymatic activity as described above.

Example 120: In the following hypothetical example and in a manner similar to that described above, G2FS2(α2,6) is converted to the corresponding carbohydrate oxazoline with CDMBI, which is subsequently reacted with ADH for about 16 hours at room temperature. SDS-PAGE electrophoresis of the resulting modified protein shows a discernible shift indicating that glycosylation of the native protein by G2FS2 (α2,6) occurs. The glycosylated ADH is desalted and assayed for enzymatic activity as described above.

Example 121: In the following hypothetical example and in a manner similar to that described above. G2FS2(α2,3) is converted to the corresponding carbohydrate oxazoline with CDMBI, which is subsequently reacted with GOx for about 16 hours at room temperature. SDS-PAGE electrophoresis of the resulting modified protein shows a discernible shift indicating that glycosylation of the native protein by G2FS2 (α2,3) occurs. The glycosylated GOx is desalted and assayed for enzymatic activity as described above.

Example 122: In the following hypothetical example and in a manner similar to that described above, G2FS2(α2,6) is converted to the corresponding carbohydrate oxazoline with CDMBI, which is subsequently reacted with GOx for about 16 hours at room temperature. SDS-PAGE electrophoresis of the resulting modified protein shows a discernible shift indicating that glycosylation of the native protein by G2FS2 (α2,6) occurs. The glycosylated GOx is desalted and assayed for enzymatic activity as described above.

Example 123: In the following hypothetical example and in a manner similar to that described above. G2FS2(α2,3) is converted to the corresponding carbohydrate oxazoline with CDMBI, which is subsequently reacted with MBP-GOx for about 16 hours at room temperature. SDS-PAGE electrophoresis of the resulting modified protein shows a discernible shift indicating that glycosylation of the native protein by G2FS2(α2,3) occurs. The glycosylated MBP-GOx is desalted and assayed for enzymatic activity as described above.

Example 124: In the following hypothetical example and in a manner similar to that described above. G2FS2(α2,6) is converted to the corresponding carbohydrate oxazoline with CDMBI, which is subsequently reacted with MBP-GOx for about 16 hours at room temperature. SDS-PAGE electrophoresis of the resulting modified protein shows a discernible shift indicating that glycosylation of the native protein by G2FS2(α2,6) occurs. The glycosylated MBP-GOx is desalted and assayed for enzymatic activity as described above.

Example 125: In the following hypothetical example and in a manner similar to that described above, G2FS2(α2,3) is converted to the corresponding carbohydrate oxazoline with CDMBI, which is subsequently reacted with LOx for about 16 hours at room temperature. SDS-PAGE electrophoresis of the resulting modified protein shows a discernible shift indicating that glycosylation of the native protein by G2FS2 (α2,3) occurs. The glycosylated LOx is desalted and assayed for enzymatic activity as described above.

Example 126: In the following hypothetical example and in a manner similar to that described above. G2FS2(α2,6) is converted to the corresponding carbohydrate oxazoline with CDMBI, which is subsequently reacted with LOx for about 16 hours at room temperature. SDS-PAGE electrophoresis of the resulting modified protein shows a discernible shift indicating that glycosylation of the native protein by G2FS2 (α2,6) occurs. The glycosylated LOx is desalted and assayed for enzymatic activity as described above.

Example 127: In the following hypothetical example and in a manner similar to that described above, G2FS2(α2,3) is converted to the corresponding carbohydrate oxazoline with CDMBI, which is subsequently reacted with MBP-LOx for about 16 hours at room temperature. SDS-PAGE electrophoresis of the resulting modified protein shows a discernible shift indicating that glycosylation of the native protein by G2FS2(α2,3) occurs. The glycosylated MBP-LOx is desalted and assayed for enzymatic activity as described above.

Example 128: In the following hypothetical example and in a manner similar to that described above. G2FS2(α2,6) is converted to the corresponding carbohydrate oxazoline with CDMBI, which is subsequently reacted with MBP-LOx for about 16 hours at room temperature. SDS-PAGE electrophoresis of the resulting modified protein shows a discernible shift indicating that glycosylation of the native protein by G2FS2(α2,6) occurs. The glycosylated MBP-LOx is desalted and assayed for enzymatic activity as described above.

Example 129: In the following hypothetical example and in a manner similar to that described above. G2FS2(α2,3) is converted to the corresponding carbohydrate oxazoline with CDMBI, which is subsequently reacted with COx1 for about 16 hours at room temperature. SDS-PAGE electrophoresis of the resulting modified protein shows a discernible shift indicating that glycosylation of the native protein by G2FS2 (α2,3) occurs. The glycosylated COx1 is desalted and assayed for enzymatic activity as described above.

Example 130: In the following hypothetical example and in a manner similar to that described above, G2FS2(α2,6) is converted to the corresponding carbohydrate oxazoline with CDMBI, which is subsequently reacted with COx1 for about 16 hours at room temperature. SDS-PAGE electrophoresis of the resulting modified protein shows a discernible shift indicating that glycosylation of the native protein by G2FS2 (α2,6) occurs. The glycosylated COx1 is desalted and assayed for enzymatic activity as described above.

Example 131: In the following hypothetical example and in a manner similar to that described above. G2FS2(α2,3) is converted to the corresponding carbohydrate oxazoline with CDMBI, which is subsequently reacted with MBP-COx1 for about 16 hours at room temperature. SDS-PAGE electrophoresis of the resulting modified protein shows a discernible shift indicating that glycosylation of the native protein by G2FS2(α2,3) occurs. The glycosylated MBP-COx1 is desalted and assayed for enzymatic activity as described above.

Example 132: In the following hypothetical example and in a manner similar to that described above, G2FS2(α2,6) is converted to the corresponding carbohydrate oxazoline with CDMBI, which is subsequently reacted with MBP-COx1 for about 16 hours at room temperature. SDS-PAGE electrophoresis of the resulting modified protein shows a discernible shift indicating that glycosylation of the native protein by G2FS2(α2,6) occurs. The glycosylated MBP-COx1 is desalted and assayed for enzymatic activity as described above.

Example 133: In the following hypothetical example and in a manner similar to that described above. G2FS2(α2,3) is converted to the corresponding carbohydrate oxazoline with CDMBI, which is subsequently reacted with COx2 for about 16 hours at room temperature. SDS-PAGE electrophoresis of the resulting modified protein shows a discernible shift indicating that glycosylation of the native protein by G2FS2 (α2,3) occurs. The glycosylated COx2 is desalted and assayed for enzymatic activity as described above.

Example 134: In the following hypothetical example and in a manner similar to that described above. G2FS2(α2,6) is converted to the corresponding carbohydrate oxazoline with CDMBI, which is subsequently reacted with COx2 for about 16 hours at room temperature. SDS-PAGE electrophoresis of the resulting modified protein shows a discernible shift indicating that glycosylation of the native protein by G2FS2 (α2,6) occurs. The glycosylated COx2 is desalted and assayed for enzymatic activity as described above.

Example 135: In the following hypothetical example and in a manner similar to that described above, G2FS2(α2,3) is converted to the corresponding carbohydrate oxazoline with CDMBI, which is subsequently reacted with MBP-COx2 for about 16 hours at room temperature. SDS-PAGE electrophoresis of the resulting modified protein shows a discernible shift indicating that glycosylation of the native protein by G2FS2(α2,3) occurs. The glycosylated MBP-COx2 is desalted and assayed for enzymatic activity as described above.

Example 136: In the following hypothetical example and in a manner similar to that described above. G2FS2(α2,6) is converted to the corresponding carbohydrate oxazoline with CDMBI, which is subsequently reacted with MBP-COx2 for about 16 hours at room temperature. SDS-PAGE electrophoresis of the resulting modified protein shows a discernible shift indicating that glycosylation of the native protein by G2FS2(α2,6) occurs. The glycosylated MBP-COx2 is desalted and assayed for enzymatic activity as described above.

Example 137: In the following hypothetical example and in a manner similar to that described above, G2FS2(α2,3) is converted to the corresponding carbohydrate oxazoline with CDMBI, which is subsequently reacted with AOx for about 16 hours at room temperature. SDS-PAGE electrophoresis of the resulting modified protein shows a discernible shift indicating that glycosylation of the native protein by G2FS2 (α2,3) occurs. The glycosylated AOx is desalted and assayed for enzymatic activity as described above.

Example 138: In the following hypothetical example and in a manner similar to that described above. G2FS2(α2,6) is converted to the corresponding carbohydrate oxazoline with CDMBI, which is subsequently reacted with AOx for about 16 hours at room temperature. SDS-PAGE electrophoresis of the resulting modified protein shows a discernible shift indicating that glycosylation of the native protein by G2FS2 (α2,6) occurs. The glycosylated AOx is desalted and assayed for enzymatic activity as described above.

Example 139: In the following hypothetical example and in a manner similar to that described above. G2FS2(α2,3) is converted to the corresponding carbohydrate oxazoline with CDMBI, which is subsequently reacted with MBP-AOx for about 16 hours at room temperature. SDS-PAGE electrophoresis of the resulting modified protein shows a discernible shift indicating that glycosylation of the native protein by G2FS2(α2,3) occurs. The glycosylated MBP-AOx is desalted and assayed for enzymatic activity as described above.

Example 140: In the following hypothetical example and in a manner similar to that described above, G2FS2(α2,6) is converted to the corresponding carbohydrate oxazoline with CDMBI, which is subsequently reacted with MBP-AOx for about 16 hours at room temperature. SDS-PAGE electrophoresis of the resulting modified protein shows a discernible shift indicating that glycosylation of the native protein by G2FS2(α2,6) occurs. The glycosylated MBP-AOx is desalted and assayed for enzymatic activity as described above.

Example 141: In the following hypothetical example and in a manner similar to that described above. G2FS2(α2,3) is converted to the corresponding carbohydrate oxazoline with CDMBI, which is subsequently reacted with GlutOx for about 16 hours at room temperature. SDS-PAGE electrophoresis of the resulting modified protein shows a discernible shift indicating that glycosylation of the native protein by G2FS2(α2,3) occurs. The glycosylated GlutOx is desalted and assayed for enzymatic activity as described above.

Example 142: In the following hypothetical example and in a manner similar to that described above, G2FS2(α2,6) is converted to the corresponding carbohydrate oxazoline with CDMBI, which is subsequently reacted with GlutOx for about 16 hours at room temperature. SDS-PAGE electrophoresis of the resulting modified protein shows a discernible shift indicating that glycosylation of the native protein by G2FS2(α2,6) occurs. The glycosylated GlutOx is desalted and assayed for enzymatic activity as described above.

Example 143: In the following hypothetical example and in a manner similar to that described above, G2FS2(α2,3) is converted to the corresponding carbohydrate oxazoline with CDMBI, which is subsequently reacted with MBP-GlutOx for about 16 hours at room temperature. SDS-PAGE electrophoresis of the resulting modified protein shows a discernible shift indicating that glycosylation of the native protein by G2FS2(α2,3) occurs. The glycosylated MBP-GlutOx is desalted and assayed for enzymatic activity as described above.

Example 144: In the following hypothetical example and in a manner similar to that described above. G2FS2(α2,6) is converted to the corresponding carbohydrate oxazoline with CDMBI, which is subsequently reacted with MBP-GlutOx for about 16 hours at room temperature. SDS-PAGE electrophoresis of the resulting modified protein shows a discernible shift indicating that glycosylation of the native protein by G2FS2(α2,6) occurs. The glycosylated MBP-GlutOx is desalted and assayed for enzymatic activity as described above.

Example 145: In the following hypothetical example and in a manner similar to that described above, G2FS2(α2,3) is converted to the corresponding carbohydrate oxazoline with CDMBI, which is subsequently reacted with SOx for about 16 hours at room temperature. SDS-PAGE electrophoresis of the resulting modified protein shows a discernible shift indicating that glycosylation of the native protein by G2FS2(α2,3) occurs. The glycosylated SOx is desalted and assayed for enzymatic activity as described above.

Example 146: In the following hypothetical example and in a manner similar to that described above. G2FS2(α2,6) is converted to the corresponding carbohydrate oxazoline with CDMBI, which is subsequently reacted with SOx for about 16 hours at room temperature. SDS-PAGE electrophoresis of the resulting modified protein shows a discernible shift indicating that glycosylation of the native protein by G2FS2(α2,6) occurs. The glycosylated SOx is desalted and assayed for enzymatic activity as described above.

Example 147: In the following hypothetical example and in a manner similar to that described above, G2FS2(α2,3) is converted to the corresponding carbohydrate oxazoline with CDMBI, which is subsequently reacted with MBP-SOx for about 16 hours at room temperature. SDS-PAGE electrophoresis of the resulting modified protein shows a discernible shift indicating that glycosylation of the native protein by G2FS2(α2,3) occurs. The glycosylated MBP-SOx is desalted and assayed for enzymatic activity as described above.

Example 148: In the following hypothetical example and in a manner similar to that described above. G2FS2(α2,6) is converted to the corresponding carbohydrate oxazoline with CDMBI, which is subsequently reacted with MBP-SOx for about 16 hours at room temperature. SDS-PAGE electrophoresis of the resulting modified protein shows a discernible shift indicating that glycosylation of the native protein by G2FS2(α2,6) occurs. The glycosylated MBP-SOx is desalted and assayed for enzymatic activity as described above.

Example 149: In the following hypothetical example and in a manner similar to that described above, partially deacetylated chitin is converted to the corresponding carbohydrate oxazoline with CDMBI, which is subsequently reacted with MBP-SOx for about 16 hours at room temperature. SDS-PAGE electrophoresis of the resulting modified protein shows a discernible shift indicating that glycosylation of the native protein by the partially deacetylated chitin oxazoline occurs. The glycosylated MBP-SOx is desalted and assayed for enzymatic activity as described above.

Example 150: In the following hypothetical example and in a manner similar to that described above, HA50 is converted to the corresponding carbohydrate oxazoline with CDMBI, which is subsequently reacted with MBP-SOx for about 16 hours at room temperature. SDS-PAGE electrophoresis of the resulting modified protein shows a discernible shift indicating that glycosylation of the native protein by the HA50 oxazoline occurs. The glycosylated MBP-SOx is desalted and assayed for enzymatic activity as described above.

Example 151: In the following hypothetical example and in a manner similar to that described above. G2FS2(α2,3) is converted to the corresponding carbohydrate oxazoline with CDMBI, which is subsequently reacted with NicOx for about 16 hours at room temperature. SDS-PAGE electrophoresis of the resulting modified protein shows a discernible shift indicating that glycosylation of the native protein by G2FS2(α2,3) occurs. The glycosylated NicOx is desalted and assayed for enzymatic activity as described above.

Example 152: In the following hypothetical example and in a manner similar to that described above, G2FS2(α2,6) is converted to the corresponding carbohydrate oxazoline with CDMBI, which is subsequently reacted with NicOx for about 16 hours at room temperature. SDS-PAGE electrophoresis of the resulting modified protein shows a discernible shift indicating that glycosylation of the native protein by G2FS2(α2,6) occurs. The glycosylated NicOx is desalted and assayed for enzymatic activity as described above.

Example 153: In the following hypothetical example and in a manner similar to that described above. G2FS2(α2,3) is converted to the corresponding carbohydrate oxazoline with CDMBI, which is subsequently reacted with MBP-NicOx for about 16 hours at room temperature. SDS-PAGE electrophoresis of the resulting modified protein shows a discernible shift indicating that glycosylation of the native protein by G2FS2(α2,3) occurs. The glycosylated MBP-NicOx is desalted and assayed for enzymatic activity as described above.

Example 154: In the following hypothetical example and in a manner similar to that described above. G2FS2(α2,6) is converted to the corresponding carbohydrate oxazoline with CDMBI, which is subsequently reacted with MBP-NicOx for about 16 hours at room temperature. SDS-PAGE electrophoresis of the resulting modified protein shows a discernible shift indicating that glycosylation of the native protein by G2FS2(α2,6) occurs. The glycosylated MBP-NicOx is desalted and assayed for enzymatic activity as described above.

Example 155: In the following hypothetical example and in a manner similar to that described above, partially deacetylated chitin is converted to the corresponding carbohydrate oxazoline with CDMBI, which is subsequently reacted with NicOx for about 16 hours at room temperature. SDS-PAGE electrophoresis of the resulting modified protein shows a discernible shift indicating that glycosylation of the native protein by the partially deacetylated chitin oxazoline occurs. The glycosylated NicOx is desalted and assayed for enzymatic activity as described above.

Example 156: In the following hypothetical example and in a manner similar to that described above, partially deacetylated chitin is converted to the corresponding carbohydrate oxazoline with CDMBI, which is subsequently reacted with MBP-NicOx for about 16 hours at room temperature. SDS-PAGE electrophoresis of the resulting modified protein shows a discernible shift indicating that glycosylation of the native protein by the partially deacetylated chitin oxazoline occurs. The glycosylated MBP-NicOx is desalted and assayed for enzymatic activity as described above.

Example 157: In the following hypothetical example and in a manner similar to that described above, HA50 is converted to the corresponding carbohydrate oxazoline with CDMBI, which is subsequently reacted with MBP-NicOx for about 16 hours at room temperature. SDS-PAGE electrophoresis of the resulting modified protein shows a discernible shift indicating that glycosylation of the native protein by the HA50 oxazoline occurs. The glycosylated MBP-NicOx is desalted and assayed for enzymatic activity as described above.

Example 158: In the following hypothetical example and in a manner similar to that described above, G2FS2($\alpha$2,3) is converted to the corresponding carbohydrate oxazoline with CDMBI, which is subsequently reacted with xanthine oxidase for about 16 hours at room temperature. SDS-PAGE electrophoresis of the resulting modified protein shows a discernible shift indicating that glycosylation of the native protein by G2FS2($\alpha$2,3) occurs. The glycosylated xanthine oxidase is desalted and assayed for enzymatic activity as described above.

Example 159: In the following hypothetical example and in a manner similar to that described above, G2FS2($\alpha$2,6) is converted to the corresponding carbohydrate oxazoline with CDMBI, which is subsequently reacted with xanthine oxidase for about 16 hours at room temperature. SDS-PAGE electrophoresis of the resulting modified protein shows a discernible shift indicating that glycosylation of the native protein by G2FS2($\alpha$2,6) occurs. The glycosylated xanthine oxidase is desalted and assayed for enzymatic activity as described above.

Example 160: In the following hypothetical example and in a manner similar to that described above. G2FS2($\alpha$2,3) is converted to the corresponding carbohydrate oxazoline with CDMBI, which is subsequently reacted with MBP-xanthine oxidase for about 16 hours at room temperature. SDS-PAGE electrophoresis of the resulting modified protein shows a discernible shift indicating that glycosylation of the native protein by G2FS2($\alpha$2,3) occurs. The glycosylated MBP-xanthine oxidase is desalted and assayed for enzymatic activity as described above.

Example 161: In the following hypothetical example and in a manner similar to that described above. G2FS2($\alpha$2,6) is converted to the corresponding carbohydrate oxazoline with CDMBI, which is subsequently reacted with MBP-xanthine oxidase for about 16 hours at room temperature. SDS-PAGE electrophoresis of the resulting modified protein shows a discernible shift indicating that glycosylation of the native protein by G2FS2($\alpha$2,6) occurs. The glycosylated MBP-xanthine oxidase is desalted and assayed for enzymatic activity as described above.

Example 162: In the following hypothetical example and in a manner similar to that described above, partially deacetylated chitin is converted to the corresponding carbohydrate oxazoline with CDMBI, which is subsequently reacted with histamine oxidase for about 16 hours at room temperature. SDS-PAGE electrophoresis of the resulting modified protein shows a discernible shift indicating that glycosylation of the native protein by the partially deacetylated chitin oxazoline occurs. The glycosylated histamine oxidase is desalted and assayed for enzymatic activity as described above.

Example 163: In the following hypothetical example and in a manner similar to that described above, HA50 is converted to the corresponding carbohydrate oxazoline with CDMBI, which is subsequently reacted with histamine oxidase for about 16 hours at room temperature. SDS-PAGE electrophoresis of the resulting modified protein shows a discernible shift indicating that glycosylation of the native protein by the HA50 oxazoline occurs. The glycosylated histamine oxidase is desalted and assayed for enzymatic activity as described above.

Example 164: In the following hypothetical example and in a manner similar to that described above, G2FS2($\alpha$2,3) is converted to the corresponding carbohydrate oxazoline with CDMBI, which is subsequently reacted with histamine oxidase for about 16 hours at room temperature. SDS-PAGE electrophoresis of the resulting modified protein shows a discernible shift indicating that glycosylation of the native protein by G2FS2($\alpha$2,3) occurs. The glycosylated histamine oxidase is desalted and assayed for enzymatic activity as described above.

Example 165: In the following hypothetical example and in a manner similar to that described above, G2FS2($\alpha$2,6) is converted to the corresponding carbohydrate oxazoline with CDMBI, which is subsequently reacted with histamine oxidase for about 16 hours at room temperature. SDS-PAGE electrophoresis of the resulting modified protein shows a discernible shift indicating that glycosylation of the native protein by G2FS2($\alpha$2,6) occurs. The glycosylated histamine oxidase is desalted and assayed for enzymatic activity as described above.

Example 166: In the following hypothetical example and in a manner similar to that described above, partially deacetylated chitin is converted to the corresponding carbohydrate oxazoline with CDMBI, which is subsequently reacted with MBP-histamine oxidase for about 16 hours at room temperature. SDS-PAGE electrophoresis of the resulting modified protein shows a discernible shift indicating that glycosylation of the native protein by the partially deacetylated chitin oxazoline occurs. The glycosylated MBP-histamine oxidase is desalted and assayed for enzymatic activity as described above.

Example 167: In the following hypothetical example and in a manner similar to that described above. HA50 is converted to the corresponding carbohydrate oxazoline with CDMBI, which is subsequently reacted with MBP-histamine oxidase for about 16 hours at room temperature. SDS-PAGE electrophoresis of the resulting modified protein shows a discernible shift indicating that glycosylation of the native protein by the HA50 oxazoline occurs. The glycosylated MBP-histamine oxidase is desalted and assayed for enzymatic activity as described above.

Example 168: In the following hypothetical example and in a manner similar to that described above, G2FS2($\alpha$2,3) is converted to the corresponding carbohydrate oxazoline with CDMBI, which is subsequently reacted with MBP-histamine oxidase for about 16 hours at room temperature. SDS-PAGE electrophoresis of the resulting modified protein shows a discernible shift indicating that glycosylation of the native protein by G2FS2($\alpha$2,3) occurs. The glycosylated MBP-histamine oxidase is desalted and assayed for enzymatic activity as described above.

Example 169: In the following hypothetical example and in a manner similar to that described above, G2FS2($\alpha$2,6) is converted to the corresponding carbohydrate oxazoline with CDMBI, which is subsequently reacted with MBP-histamine oxidase for about 16 hours at room temperature. SDS-PAGE electrophoresis of the resulting modified protein shows a discernible shift indicating that glycosylation of the native protein by G2FS2(α2,6) occurs. The glycosylated MBP-histamine oxidase is desalted and assayed for enzymatic activity as described above.

Example 170: In the following hypothetical example and in a manner similar to that described above. G2FS2(α2,3) is converted to the corresponding carbohydrate oxazoline with CDMBI, which is subsequently reacted with NADH oxidase for about 16 hours at room temperature. SDS-PAGE electrophoresis of the resulting modified protein shows a discernible shift indicating that glycosylation of the native protein by G2FS2(α2,3) occurs. The glycosylated NADH oxidase is desalted and assayed for enzymatic activity as described above.

Example 171: In the following hypothetical example and in a manner similar to that described above. G2FS2(α2,6) is converted to the corresponding carbohydrate oxazoline with CDMBI, which is subsequently reacted with NADH oxidase for about 16 hours at room temperature. SDS-PAGE electrophoresis of the resulting modified protein shows a discernible shift indicating that glycosylation of the native protein by G2FS2(α2,6) occurs. The glycosylated NADH oxidase is desalted and assayed for enzymatic activity as described above.

Example 172: In the following hypothetical example and in a manner similar to that described above, partially deacetylated chitin is converted to the corresponding carbohydrate oxazoline with CDMBI, which is subsequently reacted with MBP-NADH oxidase for about 16 hours at room temperature. SDS-PAGE electrophoresis of the resulting modified protein shows a discernible shift indicating that glycosylation of the native protein by the partially deacetylated chitin oxazoline occurs. The glycosylated MBP-NADH oxidase is desalted and assayed for enzymatic activity as described above.

Example 173: In the following hypothetical example and in a manner similar to that described above. HA50 is converted to the corresponding carbohydrate oxazoline with CDMBI, which is subsequently reacted with MBP-histamine oxidase for about 16 hours at room temperature. SDS-PAGE electrophoresis of the resulting modified protein shows a discernible shift indicating that glycosylation of the native protein by the HA50 oxazoline occurs. The glycosylated MBP-NADH oxidase is desalted and assayed for enzymatic activity as described above.

Example 174: In the following hypothetical example and in a manner similar to that described above. G2FS2(α2,3) is converted to the corresponding carbohydrate oxazoline with CDMBI, which is subsequently reacted with MBP-histamine oxidase for about 16 hours at room temperature. SDS-PAGE electrophoresis of the resulting modified protein shows a discernible shift indicating that glycosylation of the native protein by G2FS2(α2,3) occurs. The glycosylated MBP-NADH oxidase is desalted and assayed for enzymatic activity as described above.

Example 175: In the following hypothetical example and in a manner similar to that described above, G2FS2(α2,6) is converted to the corresponding carbohydrate oxazoline with CDMBI, which is subsequently reacted with MBP-histamine oxidase for about 16 hours at room temperature. SDS-PAGE electrophoresis of the resulting modified protein shows a discernible shift indicating that glycosylation of the native protein by G2FS2(α2,6) occurs. The glycosylated MBP-NADH oxidase is desalted and assayed for enzymatic activity as described above.

ADDIN EN.REFLIST 1. Taylor, M. E.; Drickamer, K., *Introduction to glycobiology.* 3rd ed.; Oxford University Press: Oxford; New York, 2011; p xix, 283 p.
2. Sold, R. J.; Griebenow, K., Effects of glycosylation on the stability of protein pharmaceuticals. *Journal of pharmaceutical sciences* 2009, 98 (4), 1223-1245.
3. Varki, A., *Essentials of glycobiology.* Third edition. ed.; Cold Spring Harbor Laboratory Press: Cold Spring Harbor, N.Y., 2017; p xxix, 823 pages.
4. Dalziel, M.; Crispin, M.; Scanlan, C. N.; Zitzmann, N.; Dwek, R. A., Emerging principles for the therapeutic exploitation of glycosylation. *Science* (New York, N.Y.) 2014, 343 (6166), 1235681.
5. Wilson, R.; Turner, A. P. F., Glucose oxidase: an ideal enzyme. *Biosensors and Bioelectronics* 1992, 7(3), 165-185.
6. Bankar, S. B.; Bule, M. V.; Singhal, R. S.; Ananthanarayan, L., Glucose oxidase—An overview. *Biotechnology Advances* 2009, 27 (4), 489-501.
7. Rich, J. R.; Withers, S. G., Emerging methods for the production of homogeneous human glycoproteins. *Nature Chemical Biology* 2008, 5, 206.
8. Li, C.; Wang, L.-X., Chemoenzymatic Methods for the Synthesis of Glycoproteins. *Chemical Reviews* 2018, 118 (17), 8359-8413.
9. Schmaltz, R. M.; Hanson, S. R.; Wong, C.-H., Enzymes in the Synthesis of Glycoconjugates. *Chemical Reviews* 2011, 111 (7), 4259-4307.
10. Zeng, Y.; Wang, J.; Li, B.; Hauser, S.; Li, H.; Wang, L. X., Glycopeptide synthesis through endo-glycosidase-catalyzed oligosaccharide transfer of sugar oxazolines: probing substrate structural requirement. *Chemistry* (Weinheim an der Bergstrasse, Germany) 2006, 12 (12), 3355-64.
11. Wang, N.; Seko, A.; Daikoku, S.; Kanie, O.; Takeda, Y.; Ito, Y., Non-enzymatic reaction of glycosyl oxazoline with peptides. *Carbohydrate research* 2016, 436, 31-35.
12. Fujita, M.; Shoda, S.; Haneda, K.; Inazu, T.; Takegawa, K.; Yamamoto, K., A novel disaccharide substrate having 1,2-oxazoline moiety for detection of transglycosylating activity of endoglycosidases. *Biochimica et biophysica acta* 2001, 1528 (1), 9-14.
13. Dutta, D.; Mandal, C.; Mandal, C., Unusual glycosylation of proteins: Beyond the universal sequon and other amino acids. *Biochimica et biophysica acta. General subjects* 2017, 1861 (12), 3096-3108.
14. Le Pape, A.; Muh, J. P.; Bailey, A. J., Characterization of N-glycosylated type I collagen in streptozotocin-induced diabetes. *The Biochemical journal* 1981, 197 (2), 405-412.
15. Robins, S. P.; Bailey, A. J., Age-related changes in collagen: the identification of reducible lysine-carbohydrate condensation products. *Biochemical and biophysical research communications* 1972, 48 (1), 76-84.
16. Wang, Y.; Xu, A.; Knight, C.; Xu, L. Y.; Cooper, G. J. S., Hydroxylation and Glycosylation of the Four Conserved Lysine Residues in the Collagenous Domain of Adiponectin: POTENTIAL ROLE IN THE MODULATION OF ITS INSULIN-SENSITIZING ACTIVITY. *Journal of Biological Chemistry* 2002, 277 (22), 19521-19529.
17. Yamauchi, M.; Sricholpech, M., Lysine post-translational modifications of collagen. *Essays in biochemistry* 2012, 52, 113-133.

18. Krafczyk, R.; Macošek, J.; Jagtap, P. K. A.; Gast, D.; Wunder, S.; Mitra, P.; Jha, A. K.; Rohr, J.; Hoffmann-Röder, A.; Jung, K.; Hennig, J.; Lassak, J., Structural Basis for EarP-Mediated Arginine Glycosylation of Translation Elongation Factor EF-P. *mBio* 2017, 8 (5), e01412-17.
19. Maekawa, H.; Yamazumi, K.; Muramatsu, S.; Kaneko, M.; Hirata, H.; Takahashi, N.; de Bosch, N. B.; Carvajal, Z.; Ojeda, A.; Arocha-Pinango, C. L.; et al., An A alpha Ser-434 to N-glycosylated Asn substitution in a dysfibrinogen, fibrinogen Caracas II, characterized by impaired fibrin gel formation. *The Journal of biological chemistry* 1991, 266 (18), 11575-81.
20. Park, J. B.; Kim, Y. H.; Yoo, Y.; Kim, J.; Jun, S.-H.; Cho, J. W.; El Qaidi, S.; Walpole, S.; Monaco, S.; García-García, A. A.; Wu, M.; Hays, M. P.; Hurtado-Guerrero, R.; Angulo, J.; Hardwidge, P. R.; Shin, J.-S.; Cho, H.-S., Structural basis for arginine glycosylation of host substrates by bacterial effector proteins. *Nature Communications* 2018, 9 (1), 4283.
21. Noguchi, M.; Fujieda, T.; Huang, W. C.; Ishihara, M.; Kobayashi, A.; Shoda, S.-i., A Practical One-Step Synthesis of 1,2-Oxazoline Derivatives from Unprotected Sugars and Its Application to Chemoenzymatic β-N-Acetylglucosaminidation of Disialo-oligosaccharide. *Helvetica Chimica Acta* 2012, 95 (10), 1928-1936.
22. Noguchi, M.; Tanaka, T.; Gyakushi, H.; Kobayashi, A.; Shoda, S.-i., Efficient Synthesis of Sugar Oxazolines from Unprotected N-Acetyl-2-amino Sugars by Using Chloroformamidinium Reagent in Water. *The Journal of organic chemistry* 2009, 74 (5), 2210-2212.
23. Huang, W.; Yang, Q.; Umekawa, M.; Yamamoto, K.; Wang, L.-X., *Arthrobacter* endo-beta-N-acetylglucosaminidase shows transglycosylation activity on complex-type N-glycan oxazolines: one-pot conversion of ribonuclease B to sialylated ribonuclease C. *Chembiochem: a European journal of chemical biology* 2010, 11 (10), 1350-1355.
24. Ochiai, H.; Huang, W.; Wang, L.-X., Endo-beta-N-acetylglucosaminidase-catalyzed polymerization of beta-Glcp-(1→4)-GlcpNAc oxazoline: a revisit to enzymatic transglycosylation. *Carbohydrate research* 2009, 344 (5), 592-598.
25. Rising, T. W. D. F.; Heidecke, C. D.; Moir, J. W. B.; Ling, Z.; Fairbanks, A. J., Endohexosaminidase-Catalysed Glycosylation with Oxazoline Donors: Fine Tuning of Catalytic Efficiency and Reversibility. *Chemistry—A European Journal* 2008, 14 (21), 6444-6464.
26. Suda, M.; Sumiyoshi, W.; Kinoshita, T.; Ohno, S., Reaction of sugar oxazolines with primary amines. *Tetrahedron Letters* 2016, 57 (49), 5446-5448.
27. Yeung, B. K. S.; Chong, P. Y. C.; Petillo, P. A., Synthesis of glycosaminoglycans. *J. Carbohydr. Chem.* 2002, 21 (Copyright (C) 2011 American Chemical Society (ACS). All Rights Reserved.), 799-865.
28. Roth, M.; Papakonstantinou, E.; Karakiulakis, G., Chapter 9—Biological Function of Glycosaminoglycans. In *Carbohydrate Chemistry, Biology and Medical Applications*, Garg, H. G.; Cowman, M. K.; Hales, C. A., Eds. Elsevier: Oxford, 2008; pp 209-226.
29. Yamada, S.; Sugahara, K.; Özbek, S., Evolution of glycosaminoglycans. *Communicative & Integrative Biology* 2011, 4 (2), 150-158.
30. Cho, Y.-W.; Jang, J.; Park, C. R.; Ko, S.-W., Preparation and Solubility in Acid and Water of Partially Deacetylated Chitins. *Biomacromolecules* 2000, 1 (4), 609-614.
31. Cheung, R. C.; Ng, T. B.; Wong, J. H.; Chan, W. Y., Chitosan: An Update on Potential Biomedical and Pharmaceutical Applications. *Marine drugs* 2015, 13 (8), 5156-86.
32. Orviský, E.; Kéry, V.; Stančiková, M., Specific high performance liquid chromatographic determination of the molecular weight and concentration of hyaluronic acid in complex mixtures by labelled hyaluronate binding proteins. *Biomedical Chromatography* 1991, 5 (6), 251-255.
33. Motohashi, N.; Mori, I., Molecular weight determination of hyaluronic acid and its separation from mouse skin extract by high-performance gel permeation chromatography using a precision differential refractometer. *Journal of Chromatography A* 1984, 299, 508-512.
34. Yeung, B.; Marecak, D., Molecular weight determination of hyaluronic acid by gel filtration chromatography coupled to matrix-assisted laser desorption ionization mass spectrometry. *Journal of Chromatography A* 1999, 852 (2), 573-581.
35. Advances in carbohydrate analysis. JAI Press: London, England; Greenwich, Conn., 1991.
36. Eschenfeldt, W. H.; Lucy, S.; Millard, C. S.; Joachimiak, A.; Mark, I. D., A family of LIC vectors for high-throughput cloning and purification of proteins. *Methods in molecular biology* (Clifton, N.J.) 2009, 498, 105-15.
37. Ausubel, F. M., *Current protocols in molecular biology*. Greene Pub. Associates; J. Wiley, order fulfillment: Brooklyn, N.Y. Media, Pa., 2003; p 2 volumes (looseleaf).
38. Zonneveld, B. J.; van der Zanden, A. L., The red ade mutants of *Kluyveromyces lactis* and their classification by complementation with cloned ADE1 or ADE2 genes from *Saccharomyces cerevisiae*. *Yeast* 1995, 11 (9), 823-7.
39. Ahmad, M.; Hirz, M.; Pichler, H.; Schwab, H., Protein expression in *Pichia pastoris*: recent achievements and perspectives for heterologous protein production. *Applied Microbiology and Biotechnology* 2014, 98 (12), 5301-5317.
40. Qiagen, The QIAexpressionist™—A handbook for high-level expression and purification of 6×His-tagged proteins. 2003, (5th Edition), 1-126.
41. Inouye, Y.; Onodera, K.; Kitaoka, S.; Kirii, T., A Simplified Preparation of N-Acetyl-D-glucosamine. *Bulletin of the Institute for Chemical Research*, Kyoto University 1955, 33 (6), 270-271.
42. Bradford, M. M., A rapid and sensitive method for the quantitation of microgram quantities of protein utilizing the principle of protein-dye binding. *Analytical Biochemistry* 1976, 72 (1), 248-254.
43. Osset, M.; Pinol, M.; Fallon, M. J.; de Llorens, R.; Cuchillo, C. M., Interference of the carbohydrate moiety in coomassie brilliant blue R-250 protein staining. *Electrophoresis* 1989, 10 (4), 271-3.
44. Møller, H. J.; Poulsen, J. H., Staining of Glycoproteins/Proteoglycans on SDS-Gels. In *The Protein Protocols Handbook*, Walker, J. M., Ed. Humana Press: Totowa, N.J., 2009; pp 569-574.
45. See, Y. P.; Olley, P. M.; Jackowski, G., The effects of high salt concentrations in the samples on molecular weight determination in sodium dodecyl sulfate polyacrylamide gel electrophoresis. *Electrophoresis* 1985, 6 (8), 382-387.
46. Gorris, H. H.; Walt, D. R., Mechanistic aspects of horseradish peroxidase elucidated through single-molecule studies. *J Am Chem Soc* 2009, 131 (17), 6277-82.

47. Zhou, M.; Diwu, Z.; Panchuk-Voloshina, N.; Haugland, R. P., A Stable Nonfluorescent Derivative of Resorufin for the Fluorometric Determination of Trace Hydrogen Peroxide: Applications in Detecting the Activity of Phagocyte NADPH Oxidase and Other Oxidases. *Analytical Biochemistry* 1997, 253 (2), 162-168.

48. Kagi, J. H. R.; Vallee, B. L., The Role of Zinc in Alcohol Dehydrogenase: V. THE EFFECT OF METAL-BINDING AGENTS ON THE STRUCTURE OF THE YEAST ALCOHOL DEHYDROGENASE MOLECULE. *Journal of Biological Chemistry* 1960, 235 (11), 3188-3192.

49. Huynh, K.; Partch, C. L., Analysis of Protein Stability and Ligand Interactions by Thermal Shift Assay. In *Current Protocols in Protein Science*, John Wiley & Sons, Inc.: 2015; pp 28.9.1-28.9.14.

We claim:

1. A method of glycosylating a starting protein having an amino sidechain with a nucleophilic moiety, said amino side chain selected from the group consisting of lysine, histidine, and arginine, said nucleophilic moiety being N, comprising the step of reacting said protein with a carbohydrate having an oxazoline moiety on the reducing end thereof in a compatible aqueous medium to covalently bond said amino sidechain of the starting protein with said oxazoline moiety, thereby producing a glycosylated protein.

2. The method of claim 1, wherein said protein is an enzyme.

3. The method of claim 2, wherein said enzyme is selected from the group consisting of oxidase, oxidoreductase, and dehydrogenase enzymes.

4. The method of claim 3, said enzyme is selected from the group consisting of glucose oxidases, lactate oxidases, alcohol oxidases, glutamate oxidases, xanthine oxidases, sarcosine oxidases, cholesterol oxidases, oxalate oxidases, NADH oxidases, D-amino acid oxidases, choline oxidases, glutathione sulfhydryl oxidases, (S)-6-hydroxynicotine oxidases, (R)-6-hydroxynicotine oxidases, nicotine oxidases, pyruvate oxidases, acyl coenzyme A oxidases, glycerolphosphate oxidases, GABA oxidases, histamine oxidases, diamine oxidases, nucleoside oxidases, L-lysine oxidases, L-aspartate oxidases, glycine oxidases, galactose oxidases, glucose dehydrogenases, alcohol dehydrogenases, cortisol dehydrogenases, lactate dehydrogenases, and fusion proteins thereof.

5. The method of claim 1, wherein said aqueous media has a pH of between 5 and 9.

6. The method of claim 1, wherein said carbohydrate has a molecular weight of at least 200 Daltons.

7. The method of claim 6, wherein said carbohydrate has a molecular weight of at least 10000 Daltons.

8. The method of claim 7, wherein said carbohydrate has a molecular weight of at least 25000 Daltons.

9. The method of claim 1, wherein said carbohydrate is linear or branched.

10. The method of claim 1, wherein said carbohydrate is selected from the group consisting of chitin, partially deacylated chitin, hyaluronic acid, keratin, keratin sulfate, chondroitin, chondroitin sulfate, dermatan, dermatan sulfate, heparin, native N-glycan cores, high-mannose N-glycans, hybrid N-glycans, complex N-glycans, and derivatives thereof.

11. The method of claim 1, said glycosylated protein has one or both of the tautomeric forms

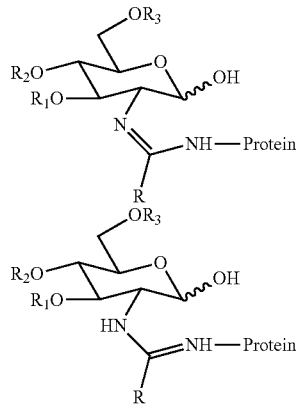

wherein each of $R_1$, $R_2$, and $R_3$ is individually and independently selected from the group consisting of H and saccharides, and wherein R is selected from the group consisting of C1-C6 alkyl, branched C3-C8 alkyl, —$(CH_2)_m$—CN, —$(CH_2)_m$OR6, —$(CH_2)_m$—$CO_2$H, —$(CH_2)_m$—$CO_2$R6, —$(CH_2)_m$—NR6(R7), —$(CH_2)_m$—S(O)$_n$—C1-C6 alkyl, —$(CH_2)_m$—C(O)NR6(R7), —$(CH_2)_m$—$CO_2$—C4-C6 heterocyclyl, —$(CH_2)_m$—C4-C6 heterocyclyl, —$(CH_2)_m$—$CO_2$—C4-C6 heteroaryl, or —$(CH_2)_m$—C4-C6-heteroaryl, wherein each alkyl may optionally contain an ether linkage and, wherein each alkyl is optionally substituted with one or two C1-C6 alkyl groups, each R6 and R7 is individually and independently H, C1-C6 alkyl, or branched C3-C8 alkyl, each m is individually and independently 1, 2, 3, 4, or 5, each n is individually and independently 0, 1, or 2.

12. The method of claim 1, including the steps of first reacting a carbohydrate having an N-acyl-2-amino group on the reducing end thereof with a dehydrating agent to form said oxazoline moiety on the reducing end of said carbohydrate, and then reacting said oxazoline carbohydrate with said starting protein.

13. The method of claim 1, wherein said glycosylated protein is selected from the group consisting of glucose oxidases modified with hyaluronic acid, glucose oxidases modified with chitin, glucose oxidases modified with partially deacetylated chitin, glucose oxidases modified with high-mannose N-glycans, glucose oxidases modified with keratin, glucose oxidases modified with keratin sulfate, glucose oxidases modified with chondroitin, glucose oxidases modified with chondroitin sulfate, glucose oxidases modified with dermatan, glucose oxidases modified with dermatan sulfate, glucose oxidases modified with heparin, glucose oxidases modified with hybrid N-glycans, glucose oxidases modified with complex N-glycans, lactate oxidases modified with hyaluronic acid, lactate oxidases modified with chitin, lactate oxidases modified with partially deacetylated chitin, lactate oxidases modified with high-mannose N-glycans, lactate oxidases modified with keratin, lactate oxidases modified with keratin sulfate, lactate oxidases modified with chondroitin, lactate oxidases modified with chondroitin sulfate, lactate oxidases modified with dermatan, lactate oxidases modified with dermatan sulfate, lactate oxidases modified with heparin, lactate oxidases modified with hybrid N-glycans, lactate oxidases modified with complex N-glycans, alcohol oxidases modified with hyaluronic acid, alcohol oxidases modified with chitin, alcohol oxidases modified with partially deacetylated chitin, alcohol oxidases modified with high-mannose N-glycans, alcohol oxidases modified with keratin, alcohol oxidases modified with keratin sulfate, alcohol oxidases modified with chondroitin, alcohol oxidases modified with chondroitin sulfate, alcohol oxidases modified with dermatan, alcohol oxidases modified with dermatan sulfate, alcohol oxidases modified with heparin, alcohol oxidases modified with hybrid N-glycans, alcohol oxidases modified with complex N-glycans, glutamate oxidases modified with hyaluronic acid, glutamate oxidases modified with chitin, glutamate oxidases modified with partially deacetylated chitin, glutamate oxidases modified with high-mannose N-glycans, glutamate oxidases modified with keratin, glutamate oxidases modified with keratin sulfate, glutamate oxidases modified with chondroitin, glutamate oxidases modified with chondroitin sulfate, glutamate oxidases modified with dermatan, glutamate oxidases modified with dermatan sulfate, glutamate oxidases modified with heparin, glutamate oxidases modified with hybrid N-glycans, glutamate oxidases modified with complex N-glycans, choline oxidases modified with hyaluronic acid, choline oxidases modified with chitin, choline oxidases modified with partially deacetylated chitin, choline oxidases modified with high-mannose N-glycans, choline oxidases modified with keratin, choline oxidases modified with keratin sulfate, choline oxidases modified with chondroitin, choline oxidases modified with chondroitin sulfate, choline oxidases modified with dermatan, choline oxidases modified with dermatan sulfate, choline oxidases modified with heparin, choline oxidases modified with hybrid N-glycans, choline oxidases modified with complex N-glycans, sarcosine oxidases modified with hyaluronic acid, sarcosine oxidases modified with chitin, sarcosine oxidases modified with partially deacetylated chitin, sarcosine oxidases modified with high-mannose N-glycans, sarcosine oxidases modified with keratin, sarcosine oxidases modified with keratin sulfate, sarcosine oxidases modified with chondroitin, sarcosine oxidases modified with chondroitin sulfate, sarcosine oxidases modified with dermatan, sarcosine oxidases modified with dermatan sulfate, sarcosine oxidases modified with heparin, sarcosine oxidases modified with hybrid N-glycans, sarcosine oxidases modified with complex N-glycans, xanthine oxidases modified with hyaluronic acid, xanthine oxidases modified with chitin, xanthine oxidases modified with partially deacetylated chitin, xanthine oxidases modified with high-mannose N-glycans, xanthine oxidases modified with keratin, xanthine oxidases modified with keratin sulfate, xanthine oxidases modified with chondroitin, xanthine oxidases modified with chondroitin sulfate, xanthine oxidases modified with dermatan, xanthine oxidases modified with dermatan sulfate, xanthine oxidases modified with heparin, xanthine oxidases modified with hybrid N-glycans, xanthine oxidases modified with complex N-glycans, oxalate oxidases modified with hyaluronic acid, oxalate oxidases modified with chitin, oxalate oxidases modified with partially deacetylated chitin, oxalate oxidases modified with high-mannose N-glycans, oxalate oxidases modified with keratin, oxalate oxidases modified with keratin sulfate, oxalate oxidases modified with chondroitin, oxalate oxidases modified with chondroitin sulfate, oxalate oxidases modified with dermatan, oxalate oxidases modified with dermatan sulfate, oxalate oxidases modified with heparin, oxalate oxidases modified with hybrid N-glycans, oxalate oxidases modified with complex N-glycans, cholesterol oxidases modified with hyaluronic acid, cholesterol oxidases modified with chitin, cholesterol oxidases modified with partially deacetylated chitin, cholesterol oxidases modified with high-mannose N-glycans, cholesterol oxidases modified with keratin, cholesterol oxidases modified with keratin sulfate, cholesterol oxidases modified with chondroitin, cholesterol oxidases modified with chondroitin sulfate, cholesterol oxidases modified with dermatan, cholesterol oxidases modified with dermatan sulfate, cholesterol oxidases modified with heparin, cholesterol oxidases modified with hybrid N-glycans, cholesterol oxidases modified with complex N-glycans, histamine oxidases modified with hyaluronic acid, histamine oxidases modified with chitin, histamine oxidases modified with partially deacetylated chitin, histamine oxidases modified with high-mannose N-glycans, histamine oxidases modified with keratin, histamine oxidases modified with keratin sulfate, histamine oxidases modified with chondroitin, histamine oxidases modified with chondroitin sulfate, histamine oxidases modified with dermatan, histamine oxidases modified with dermatan sulfate, histamine oxidases modified with heparin, histamine oxidases modified with hybrid N-glycans, histamine oxidases modified with complex N-glycans, glycine oxidases modified with hyaluronic acid, glycine oxidases modified with chitin, glycine oxidases modified with partially deacetylated chitin, glycine oxidases modified with high-mannose N-glycans, glycine oxidases modified with keratin, glycine oxidases modified with keratin sulfate, glycine oxidases modified with chondroitin, glycine oxidases modified with chondroitin sulfate, glycine oxidases modified with dermatan, glycine oxidases modified with dermatan sulfate, glycine oxidases modified with heparin, glycine oxidases modified with hybrid N-glycans, glycine oxidases modified with complex N-glycans, NADH oxidases modified with hyaluronic acid, NADH oxidases modified with chitin, NADH oxidases modified with partially deacetylated chitin, NADH oxidases modified with high-mannose N-glycans, NADH oxidases modified with keratin, NADH oxidases modified with keratin sulfate, NADH oxidases modified with chondroitin, NADH oxidases modified with chondroitin sulfate, NADH oxidases modified with dermatan, NADH oxidases modified with dermatan sulfate, NADH oxidases modified with heparin, NADH oxidases modified with hybrid N-glycans, NADH oxidases modified with complex N-glycans, galactose oxidases modified with hyaluronic acid, galactose oxidases modified with chitin, galactose oxidases modified with partially deacetylated chitin, galactose oxidases modified with high-mannose N-glycans, galactose oxidases modified with keratin, galactose oxidases modified with keratin sulfate, galactose oxidases modified with chondroitin, galactose oxidases modified with chondroitin sulfate, galactose oxidases modified with dermatan, galactose oxidases modified with dermatan sulfate, galactose oxidases modified with heparin, galactose oxidases modified with hybrid N-glycans, galactose oxidases modified with complex N-glycans, alcohol dehydrogenases modified with hyaluronic acid, alcohol dehydrogenases modified with chitin, alcohol dehydrogenases modified with partially deacetylated chitin, alcohol dehydrogenases modified with high-mannose N-glycans, alcohol dehydrogenases modified with keratin, alcohol dehydrogenases modified with keratin sulfate, alcohol dehydrogenases modified with chondroitin, alcohol dehydrogenases modified with chondroitin sulfate, alcohol dehydrogenases modified with dermatan, alcohol dehydrogenases modified with dermatan sulfate, alcohol dehydrogenases modified with heparin, alcohol dehydrogenases modified with hybrid N-glycans, alcohol dehydrogenases modified with complex N-glycans, glucose dehydrogenases modified with hyaluronic acid, glucose dehydrogenases modified with chitin, glucose dehydrogenases modified with partially deacetylated chitin, glucose dehydrogenases modified with high-mannose N-glycans, glucose dehydrogenases modified with keratin, glucose dehydrogenases modified with keratin sulfate, glucose dehydrogenases modified with chondroitin, glucose dehydrogenases modified with chondroitin sulfate, glucose dehydrogenases modified with dermatan, glucose dehydrogenases modified with dermatan sulfate, glucose dehydrogenases modified with heparin, glucose dehydrogenases modified with hybrid N-glycans, glucose dehydrogenases modified with complex N-glycans, L-lactate dehydrogenases modified with hyaluronic acid, L-lactate dehydrogenases modified with chitin, L-lactate dehydrogenases modified with partially deacetylated chitin, L-lactate dehydrogenases modified with high-mannose N-glycans, L-lactate dehydrogenases modified with keratin, L-lactate dehydrogenases modified with keratin sulfate, L-lactate dehydrogenases modified with chondroitin, L-lactate dehydrogenases modified with chondroitin sulfate, L-lactate dehydrogenases modified with dermatan, L-lactate dehydrogenases modified with dermatan sulfate, L-lactate dehydrogenases modified with heparin, L-lactate dehydrogenases modified with hybrid N-glycans, L-lactate dehydrogenases modified with complex N-glycans, cortisol dehydrogenases modified with hyaluronic acid, cortisol dehydrogenases modified with chitin, cortisol dehydrogenases modified with partially deacetylated chitin, cortisol dehydrogenases modified with high-mannose N-glycans, cortisol dehydrogenases modified with keratin, cortisol dehydrogenases modified with keratin sulfate, cortisol dehydrogenases modified with chondroitin, cortisol dehydrogenases modified with chondroitin sulfate, cortisol dehydrogenases modified with dermatan, cortisol dehydrogenases modified with dermatan sulfate, cortisol dehydrogenases modified with heparin, cortisol dehydrogenases modified with hybrid N-glycans, cortisol dehydrogenases modified with complex N-glycans, galactose dehydrogenases modified with hyaluronic acid, galactose dehydrogenases modified with chitin, galactose dehydrogenases modified with partially deacetylated chitin, galactose dehydrogenases modified with high-mannose N-glycans, galactose dehydrogenases modified with keratin, galactose dehydrogenases modified with keratin sulfate, galactose dehydrogenases modified with chondroitin, galactose dehydrogenases modified with chondroitin sulfate, galactose dehydrogenases modified with dermatan, galactose dehydrogenases modified with dermatan sulfate, galactose dehydrogenases modified with heparin, galactose dehydrogenases modified with hybrid N-glycans, galactose dehydrogenases modified with complex N-glycans, glycerol dehydrogenases modified with hyaluronic acid, glycerol dehydrogenases modified with chitin, glycerol dehydrogenases modified with partially deacetylated chitin, glycerol dehydrogenases modified with high-mannose N-glycans, glycerol dehydrogenases modified with keratin, glycerol dehydrogenases modified with keratin sulfate, glycerol dehydrogenases modified with chondroitin, glycerol dehydrogenases modified with chondroitin sulfate, glycerol dehydrogenases modified with dermatan, glycerol dehydrogenases modified with dermatan sulfate, glycerol dehydrogenases modified with heparin, glycerol dehydrogenases modified with hybrid N-glycans, glycerol dehydrogenases modified with complex N-glycans, glucose-6-phosphate dehydrogenases modified with hyaluronic acid, glucose-6-phosphate dehydrogenases modified with chitin, glucose-6-phosphate dehydrogenases modified with partially deacetylated chitin, glucose-6-phosphate dehydrogenases modified with high-mannose N-glycans, glucose-6-phosphate dehydrogenases modified with keratin, glucose-6-phosphate dehydrogenases modified with keratin sulfate, glucose-6-phosphate dehydrogenases modified with chondroitin, glucose-6-phosphate dehydrogenases modified with chondroitin sulfate, glucose-6-phosphate dehydrogenases modified with dermatan, glucose-6-phosphate dehydrogenases modified with dermatan sulfate, glucose-6-phosphate dehydrogenases modified with heparin, glucose-6-phosphate dehydrogenases modified with hybrid N-glycans, glucose-6-phosphate dehydrogenases modified with complex N-glycans, 3-hydroxybutyrate dehydrogenases modified with hyaluronic acid, 3-hydroxybutyrate dehydrogenases modified with chitin, 3-hydroxybutyrate dehydrogenases modified with partially deacetylated chitin, 3-hydroxybutyrate dehydrogenases modified with high-mannose N-glycans, 3-hydroxybutyrate dehydrogenases modified with keratin, 3-hydroxybutyrate dehydrogenases modified with keratin sulfate, 3-hydroxybutyrate dehydrogenases modified with chondroitin, 3-hydroxybutyrate dehydrogenases modified with chondroitin sulfate, 3-hydroxybutyrate dehydrogenases modified with dermatan, 3-hydroxybutyrate dehydrogenases modified with dermatan sulfate, 3-hydroxybutyrate dehydrogenases modified with heparin, 3-hydroxybutyrate dehydrogenases modified with hybrid N-glycans, 3-hydroxybutyrate dehydrogenases modified with complex N-glycans, L-malate dehydrogenases modified with hyaluronic acid, L-malate dehydrogenases modified with chitin, L-malate dehydrogenases modified with partially deacetylated chitin, L-malate dehydrogenases modified with high-mannose N-glycans, L-malate dehydrogenases modified with keratin, L-malate dehydrogenases modified with keratin sulfate, L-malate dehydrogenases modified with chondroitin, L-malate dehydrogenases modified with chondroitin sulfate, L-malate dehydrogenases modified with dermatan, L-malate dehydrogenases modified with dermatan sulfate, L-malate dehydrogenases modified with heparin, L-malate dehydrogenases modified with hybrid N-glycans, L-malate dehydrogenases modified with complex N-glycans, sorbitol dehydrogenases modified with hyaluronic acid, sorbitol dehydrogenases modified with chitin, sorbitol dehydrogenases modified with partially deacetylated chitin, sorbitol dehydrogenases modified with high-mannose N-glycans, sorbitol dehydrogenases modified with keratin, sorbitol dehydrogenases modified with keratin sulfate, sorbitol dehydrogenases modified with chondroitin, sorbitol dehydrogenases modified with chondroitin sulfate, sorbitol dehydrogenases modified with dermatan, sorbitol dehydrogenases modified with dermatan sulfate, sorbitol dehydrogenases modified with heparin, sorbitol dehydrogenases modified with hybrid N-glycans, and sorbitol dehydrogenases modified with complex N-glycans, and fusion proteins thereof.

14. The method of claim 13, wherein said glycosylated protein is selected from the group consisting of glucose oxidases modified with hyaluronic acid, glucose oxidases modified with partially deacetylated chitin, glucose oxidases modified with complex N-glycans, lactate oxidases modified with hyaluronic acid, lactate oxidases modified with partially deacetylated chitin, lactate oxidases modified with complex N-glycans, alcohol oxidases modified with hyaluronic acid, alcohol oxidases modified with partially deacetylated chitin, alcohol oxidases modified with complex N-glycans, glutamate oxidases modified with hyaluronic acid, glutamate oxidases modified with partially deacetylated chitin, glutamate oxidases modified with complex N-glycans, choline oxidases modified with hyaluronic acid, choline oxidases modified with partially deacetylated chitin, choline oxidases modified with complex N-glycans, sarcosine oxidases modified with hyaluronic acid, sarcosine oxidases modified with partially deacetylated chitin, sarcosine oxidases modified with complex N-glycans, xanthine oxidases modified with hyaluronic acid, xanthine oxidases modified with partially deacetylated chitin, xanthine oxidases modified with complex N-glycans, cholesterol oxidases modified with hyaluronic acid, cholesterol oxidases modified with partially deacetylated chitin, cholesterol oxidases modified with complex N-glycans, histamine oxidases modified with hyaluronic acid, histamine oxidases modified with partially deacetylated chitin, histamine oxidases modified with complex N-glycans, NADH oxidases modified with hyaluronic acid, NADH oxidases modified with partially deacetylated chitin, NADH oxidases modified with complex N-glycans, alcohol dehydrogenases modified with hyaluronic acid, alcohol dehydrogenases modified with partially deacetylated chitin, alcohol dehydrogenases modified with complex N-glycans, glucose dehydrogenases modified with hyaluronic acid, glucose dehydrogenases modified with partially deacetylated chitin, glucose dehydrogenases modified with complex N-glycans, L-lactate dehydrogenases modified with hyaluronic acid, L-lactate dehydrogenases modified with partially deacetylated chitin, L-lactate dehydrogenases modified with complex N-glycans, cortisol dehydrogenases modified with hyaluronic acid, cortisol dehydrogenases modified with partially deacetylated chitin, cortisol dehydrogenases modified with complex N-glycans, L-malate dehydrogenases modified with hyaluronic acid, L-malate dehydrogenases modified with partially deacetylated chitin, and L-malate dehydrogenases modified with complex N-glycans, and fusion proteins thereof.

15. The method of claim 1, wherein said glycosylated protein is a glucose oxidase, said glucose oxidase being hyper-glycosylated.

* * * * *